United States Patent
Seo et al.

(10) Patent No.: US 10,270,051 B2
(45) Date of Patent: *Apr. 23, 2019

(54) LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Satoshi Seo, Kanagawa (JP); Hiromi Seo, Kanagawa (JP); Tsunenori Suzuki, Kanagawa (JP); Hiromitsu Kido, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/989,611

(22) Filed: May 25, 2018

(65) Prior Publication Data
US 2018/0277784 A1    Sep. 27, 2018

Related U.S. Application Data

(63) Continuation of application No. 15/597,339, filed on May 17, 2017, now Pat. No. 9,985,234.

(30) Foreign Application Priority Data

May 20, 2016  (JP) ................... 2016-101789
Jun. 21, 2016  (JP) ................... 2016-122964

(51) Int. Cl.
| | |
|---|---|
| H01L 51/52 | (2006.01) |
| H01L 51/50 | (2006.01) |
| C07D 209/82 | (2006.01) |
| C09K 11/06 | (2006.01) |
| H01L 27/32 | (2006.01) |
| H01L 51/00 | (2006.01) |
| H01L 51/56 | (2006.01) |

(52) U.S. Cl.
CPC ........ *H01L 51/5016* (2013.01); *C07D 209/82* (2013.01); *C09K 11/06* (2013.01);
(Continued)

(58) Field of Classification Search
CPC . H01L 51/5016; H01L 51/5262; H01L 51/52; H01L 51/56; H01L 51/5068;
(Continued)

(56) References Cited

U.S. PATENT DOCUMENTS

| | | | |
|---|---|---|---|
| 7,332,858 B2 | 2/2008 | Nomura et al. | |
| 8,653,553 B2 * | 2/2014 | Yamazaki | H01L 33/504 257/79 |

(Continued)

FOREIGN PATENT DOCUMENTS

JP    2012-129509 A    7/2012

OTHER PUBLICATIONS

Yokoyama, D., "Molecular Orientation in Small-Molecule Organic Light-Emitting Diodes," Journal of Materials Chemistry, Dec. 28, 2011, vol. 21, No. 48, pp. 19187-19202.

(Continued)

*Primary Examiner* — Michael M Trinh
(74) *Attorney, Agent, or Firm* — Husch Blackwell LLP

(57) ABSTRACT

A light-emitting element is provided. The light-emitting element includes first and second electrodes and an EL layer therebetween. The EL layer includes a light-emitting layer containing first and second substances. The amount of the first substance is larger than that of the second substance. The second substance emits light. Average transition dipole moments of the second substance are divided into three components in x-, y-, and z-directions which are orthogonal to each other. Components parallel to the first or second electrode are assumed to be the components in the x- and y-directions, and a component perpendicular to the first or (Continued)

second electrode is assumed to be the component in the z-direction. The proportion of the component in the z-direction is represented by a, which is less than or equal to 0.2.

20 Claims, 41 Drawing Sheets

(52) U.S. Cl.
CPC ...... *H01L 27/3209* (2013.01); *H01L 27/3244* (2013.01); *H01L 27/3258* (2013.01); *H01L 51/0034* (2013.01); *H01L 51/0085* (2013.01); *H01L 51/504* (2013.01); *H01L 51/5012* (2013.01); *H01L 51/5068* (2013.01); *H01L 51/5084* (2013.01); *H01L 51/5092* (2013.01); *H01L 51/52* (2013.01); *H01L 51/5215* (2013.01); *H01L 51/5234* (2013.01); *H01L 51/5246* (2013.01); *H01L 51/5262* (2013.01); *H01L 51/5265* (2013.01); *H01L 51/56* (2013.01); *H01L 51/006* (2013.01); *H01L 51/0056* (2013.01); *H01L 51/0067* (2013.01); *H01L 51/0072* (2013.01); *H01L 51/0074* (2013.01); *H01L 2251/5384* (2013.01); *H01L 2251/55* (2013.01)

(58) Field of Classification Search
CPC ............. H01L 51/5084; H01L 51/5192; H01L 51/5206; H01L 51/5215; H01L 51/5221; H01L 51/5234; H01L 51/5246; H01L 51/0034; H01L 51/0084; C09K 11/06; C07D 209/82
See application file for complete search history.

(56) References Cited

U.S. PATENT DOCUMENTS

| | | | |
|---|---|---|---|
| 8,916,897 B2* | 12/2014 | Yamazaki | H01L 33/50 257/98 |
| 8,986,857 B2 | 3/2015 | Suzuki et al. | |
| 8,994,263 B2* | 3/2015 | Shitagaki | H01L 51/0072 313/504 |
| 9,130,184 B2* | 9/2015 | Seo | H01L 51/0085 |
| 9,276,222 B2 | 3/2016 | Inoue et al. | |
| 9,343,691 B2 | 5/2016 | Seo et al. | |
| 9,362,517 B2 | 6/2016 | Ohsawa et al. | |
| 9,365,921 B2 | 6/2016 | Yamazaki et al. | |
| 9,368,742 B2 | 6/2016 | Kawata et al. | |
| 9,412,956 B2 | 8/2016 | Ohsawa et al. | |
| 9,515,279 B2 | 12/2016 | Ishisone et al. | |
| 9,548,468 B2 | 1/2017 | Seo et al. | |
| 9,653,517 B2 | 5/2017 | Uesaka et al. | |
| 9,653,705 B2 | 5/2017 | Uesaka et al. | |
| 2002/0061418 A1 | 5/2002 | Imanishi | |
| 2005/0052123 A1 | 3/2005 | Suzuki et al. | |
| 2006/0278849 A1 | 12/2006 | Suzuki et al. | |
| 2010/0247747 A1 | 9/2010 | Yamazaki | |
| 2011/0050082 A1* | 3/2011 | Inoue | H01L 51/5268 313/483 |
| 2012/0126212 A1 | 5/2012 | Yamazaki et al. | |
| 2015/0333283 A1 | 11/2015 | Ishisone et al. | |
| 2016/0079314 A1 | 3/2016 | Seo et al. | |
| 2016/0097501 A1 | 4/2016 | Yoshitani et al. | |
| 2016/0118605 A1 | 4/2016 | Kawakami et al. | |
| 2016/0118615 A1 | 4/2016 | Seo et al. | |
| 2016/0126463 A1* | 5/2016 | Kadoma | H01L 51/0054 257/40 |
| 2016/0126500 A1 | 5/2016 | Uesaka et al. | |
| 2016/0190500 A1 | 6/2016 | Watabe et al. | |
| 2016/0248031 A1 | 8/2016 | Seo | |
| 2016/0248033 A1 | 8/2016 | Uesaka et al. | |
| 2016/0336519 A1 | 11/2016 | Seo et al. | |
| 2016/0359123 A1* | 12/2016 | Thompson | H01L 51/0085 |
| 2017/0062734 A1 | 3/2017 | Suzuki et al. | |
| 2017/0155072 A1 | 6/2017 | Hashimoto et al. | |
| 2017/0222156 A1 | 8/2017 | Kawakami et al. | |

OTHER PUBLICATIONS

Liehm, P. et al., "Comparing the Emissive Dipole Orientation of Two Similar Phosphorescent Green Emitter Molecules in Highly Efficient Organic Light-Emitting Diodes," Applied Physics Letters, Dec. 17, 2012, vol. 101, No. 25, pp. 253304-1-253304-4.

* cited by examiner

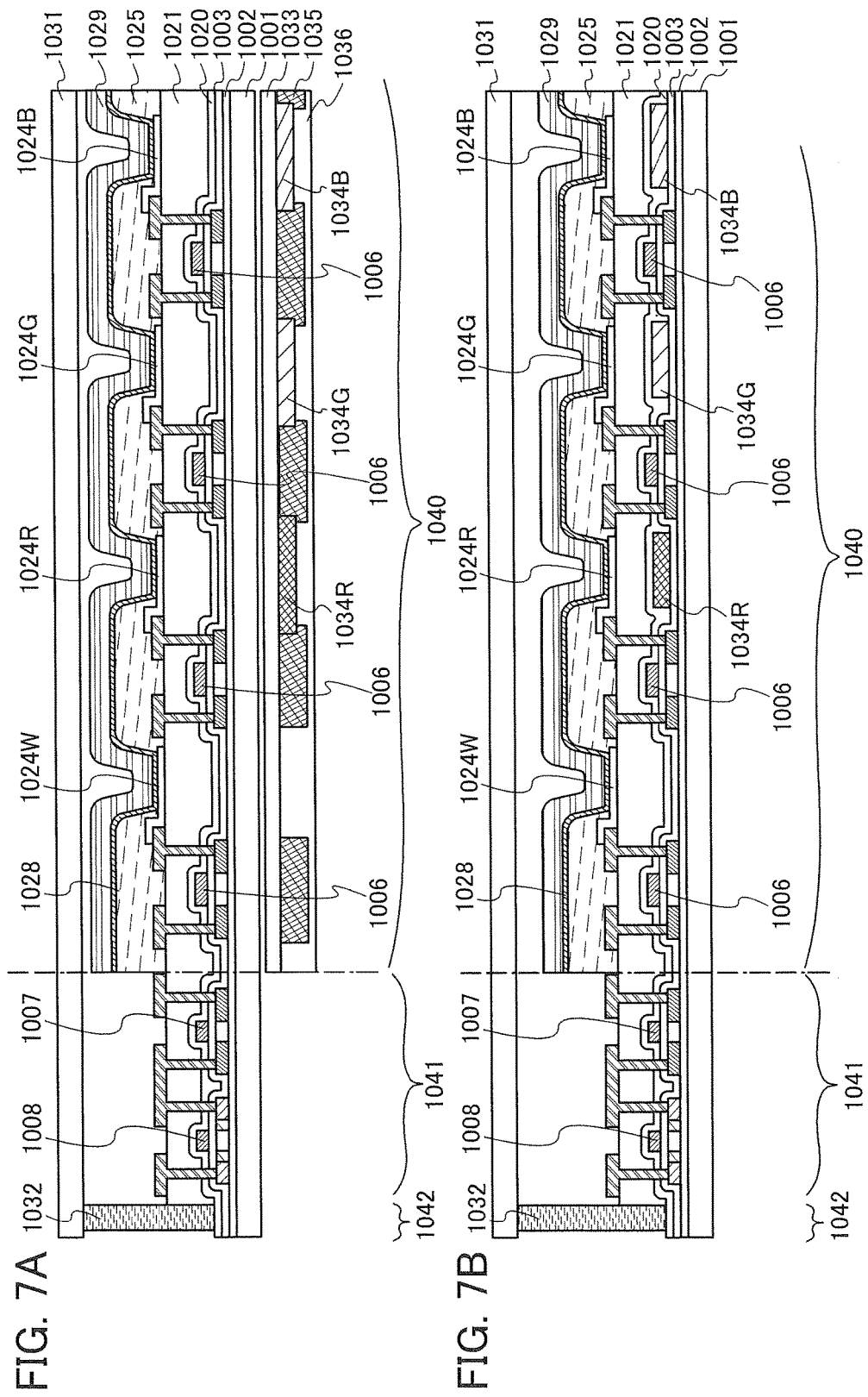

FIG. 11A
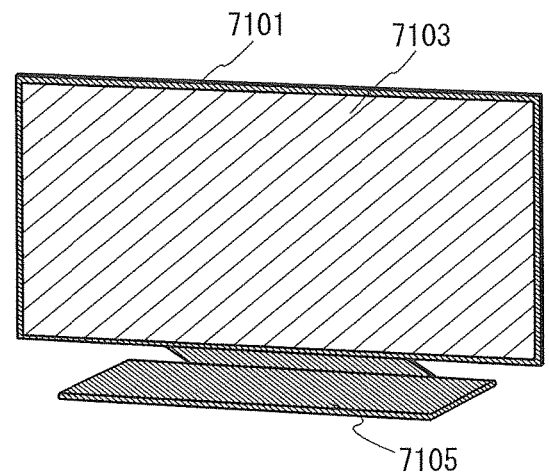
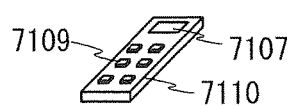
FIG. 11B1
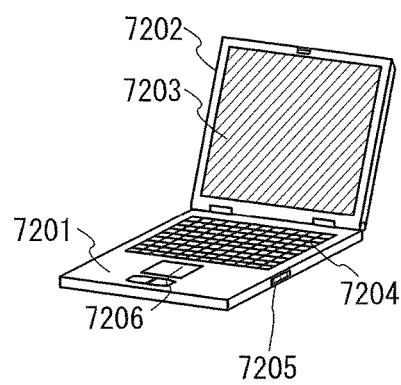
FIG. 11B2
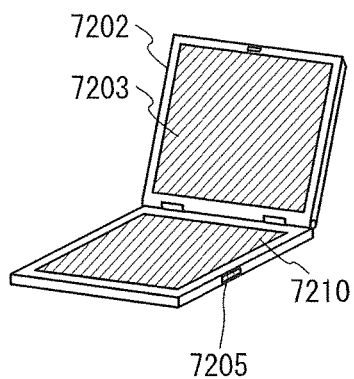
FIG. 11C
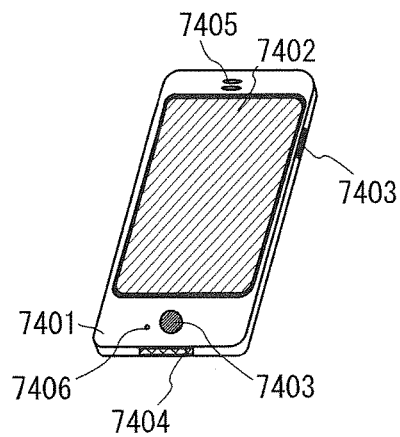
FIG. 11D
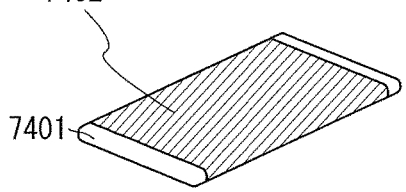

FIG. 19  Blue Fluorescence

FIG. 21  Blue Fluorescence

Blue Fluorescence

Blue Fluorescence

FIG. 24  Yellow Phosphorescence
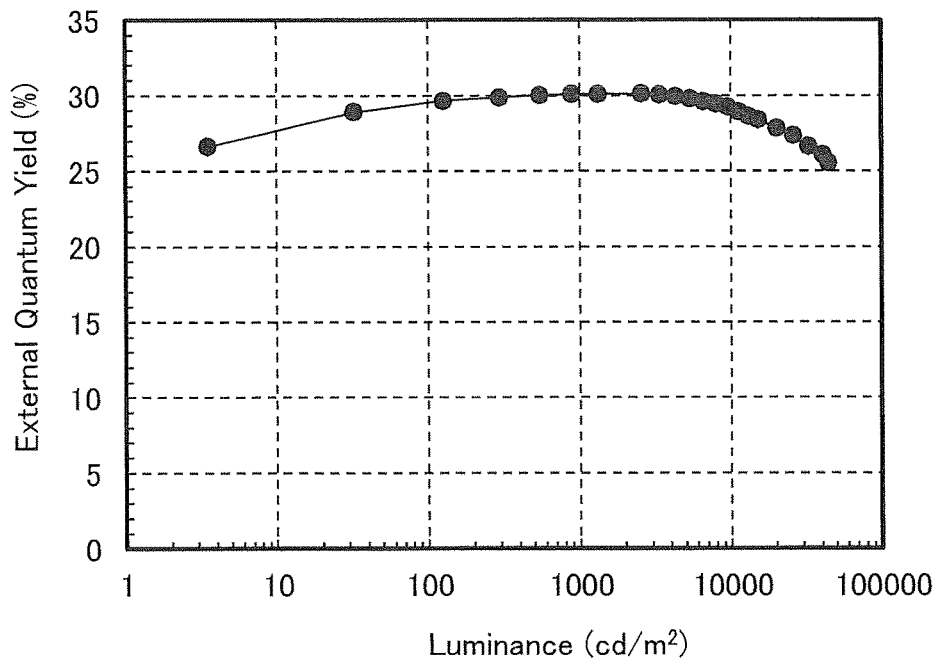
FIG. 25  Yellow Phosphorescence
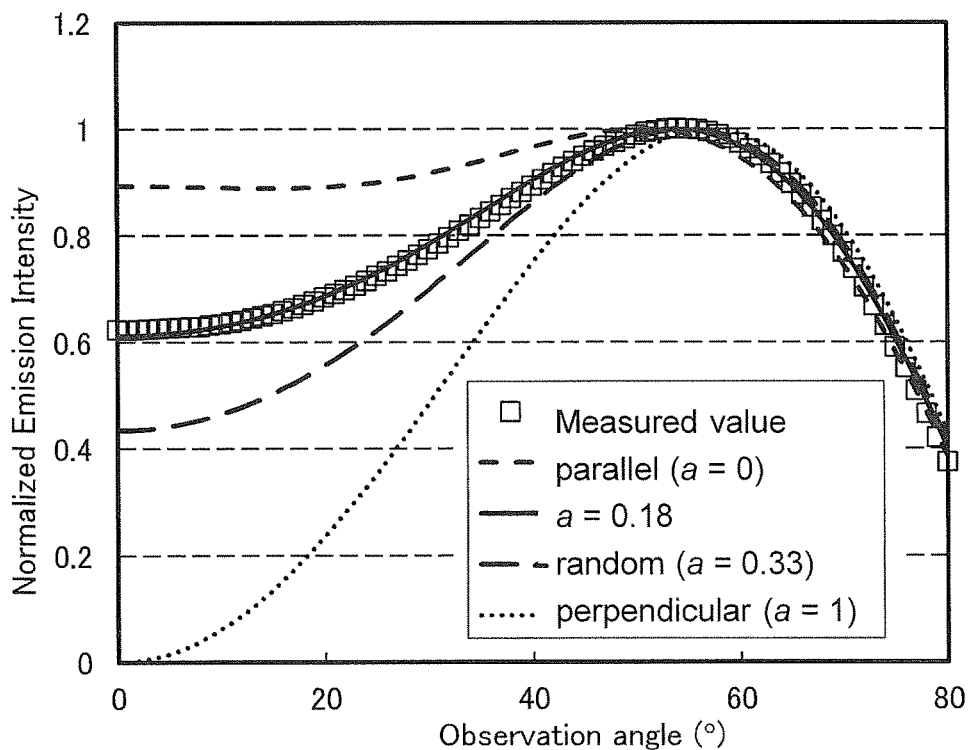

Yellow Phosphorescence

Yellow Phosphorescence

LIGHT-EMITTING ELEMENT, LIGHT-EMITTING DEVICE, ELECTRONIC DEVICE, AND LIGHTING DEVICE

This application is a continuation of U.S. application Ser. No. 15/597,339, filed on May 17, 2017 (now U.S. Pat. No. 9,985,234 issued May 29, 2018) which is incorporated herein by reference.

BACKGROUND OF THE INVENTION

1. Field of the Invention

One embodiment of the present invention relates to a light-emitting element, a display module, a lighting module, a display device, a light-emitting device, an electronic device, and a lighting device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a memory device, a method for driving any of them, and a method for manufacturing any of them.

2. Description of the Related Art

As lighting devices or display devices, display devices including light-emitting elements (organic EL elements) in which organic compounds or organometallic complexes are used as light-emitting substances have been developed because of their potential for thinness, lightness, high-speed response to input signals, low power consumption, and the like.

In an organic EL element, voltage application between electrodes between which a light-emitting layer is provided causes recombination of electrons and holes injected from the electrodes, which brings a light-emitting substance into an excited state, and the return from the excited state to the ground state is accompanied by light emission. Since the spectrum of light emitted from the light-emitting substance depends on the light-emitting substance, the use of different types of light-emitting substances makes it possible to obtain light-emitting elements which exhibit various colors.

Although displays or lighting devices including light-emitting elements are suitably used for a variety of electronic devices, their performance has plenty of room to improve. For example, the current efficiency of a light-emitting element is preferably as high as possible. However, the internal quantum efficiency of a light-emitting element for both fluorescence and phosphorescence is going to reach the theoretical limit; in particular, by utilizing a triplet excited state, some light-emitting elements that emit fluorescence have achieved an internal quantum efficiency of 25%, which is a theoretical limit, or higher.

In order to enhance the current efficiency of a light-emitting element whose internal quantum efficiency has been improved, the light extraction efficiency of the element needs to be improved.

Patent Document 1 discloses a light-emitting element whose light extraction efficiency is improved by depositing light-emitting substances such that their orientations are aligned with each other to control the direction of light emission.

REFERENCE

Patent Document

[Patent Document 1] Japanese Published Patent Application No. 2012-129509

Non-Patent Document

[Non-Patent Document 1] D. Yokoyama, Journal of Materials Chemistry, 2011, 21, 19187
[Non-Patent Document 2] P. Liehm et al., Applied Physics Letters, 101, 253304 (2012)

SUMMARY OF THE INVENTION

An object of one embodiment of the present invention is to provide a novel light-emitting element. Another object is to provide a novel light-emitting element with high emission efficiency.

An object of another embodiment of the present invention is to provide a display module, a lighting module, a light-emitting device, a display device, an electronic device, and a lighting device each having low power consumption.

It is only necessary that at least one of the above objects be achieved in one embodiment of the present invention. Note that the description of these objects does not disturb the existence of other objects. In one embodiment of the present invention, there is no need to achieve all the objects. Other objects will be apparent from and can be derived from the description of the specification, the drawings, the claims, and the like.

One embodiment of the present invention is a light-emitting element including a first electrode, a second electrode, and an EL layer between the first electrode and the second electrode. The EL layer includes a light-emitting layer. The light-emitting layer contains a first substance and a second substance. The amount of the first substance is larger than the amount of the second substance in the light-emitting layer. The second substance emits light. The value of a parameter a of the light-emitting element is less than or equal to 0.2; the parameter a is a ratio of light emission from a perpendicular component in a z-direction to the whole light emission when light emission from average transition dipoles of the second substance in the light-emitting layer is divided into light emission from three components of transition dipoles in an x-direction, a y-direction, and the z-direction which are orthogonal to each other (note that the x-direction and the y-direction are defined as directions parallel to the first electrode or the second electrode while the z-direction is defined as a direction perpendicular to the first electrode or the second electrode).

Another embodiment of the present invention is a light-emitting element having the above structure in which the second substance is a phosphorescent substance.

Another embodiment of the present invention is a light-emitting element having the above structure in which the second substance is an iridium complex.

Another embodiment of the present invention is a light-emitting element having the above structure in which the external quantum efficiency is higher than or equal to 25%.

Another embodiment of the present invention is a light-emitting element having the above structure in which the light-emitting layer further contains a third substance and the first substance and the third substance form an exciplex.

Another embodiment of the present invention is a light-emitting element having the above structure in which the second substance is a fluorescent substance.

Another embodiment of the present invention is a light-emitting element having the above structure in which the second substance is a substance having a condensed aromatic hydrocarbon skeleton.

Another embodiment of the present invention is a light-emitting element having the above structure in which the external quantum efficiency is higher than or equal to 7.5%.

Another embodiment of the present invention is a light-emitting element having the above structure in which the external quantum efficiency is higher than or equal to 10%.

Another embodiment of the present invention is a light-emitting element having the above structure in which light emission from the light-emitting element includes a delayed fluorescent component.

Another embodiment of the present invention is a light-emitting element having the above structure in which a is greater than or equal to 0 and less than or equal to 0.2.

Another embodiment of the present invention is a light-emitting device including the above-described light-emitting element and at least one of a transistor and a substrate.

Another embodiment of the present invention is an electronic device including the above-described light-emitting device and at least one of a sensor, an operation button, a speaker, and a microphone.

Another embodiment of the present invention is a lighting device including the above-described light-emitting device and a housing.

Note that a light-emitting device in this specification includes, in its category, an image display device including a light-emitting element. A light-emitting device may be included in a module in which a light-emitting element is provided with a connector such as an anisotropic conductive film or a tape carrier package (TCP), a module in which a printed wiring board is provided at the end of a TCP, and a module in which an integrated circuit (IC) is directly mounted on a light-emitting element by a chip on glass (COG) method. The light-emitting device may also be included in lighting equipment.

In one embodiment of the present invention, a novel light-emitting element can be provided. Also, a novel light-emitting element with high emission efficiency can be provided.

Another embodiment of the present invention can provide a display module, a lighting module, a light-emitting device, a display device, an electronic device, and a lighting device each having low power consumption.

It is only necessary that at least one of the above effects be achieved in one embodiment of the present invention. Note that the description of these effects does not disturb the existence of other effects. One embodiment of the present invention does not necessarily achieve all the effects listed above. Other effects will be apparent from and can be derived from the description of the specification, the drawings, the claims, and the like.

BRIEF DESCRIPTION OF THE DRAWINGS

FIGS. 7A and 7B are conceptual diagrams each illustrating an active matrix light-emitting device.

FIGS. 11A to 11D each illustrate an electronic device.

FIG. 24 shows the external quantum efficiency-luminance characteristics of Light-emitting Element 2.

FIG. 25 is a graph showing the measured and calculated integrated intensity of the EL emission spectrum depending on the angle ($\theta$) of the detector of Light-emitting Element 2-1.

DETAILED DESCRIPTION OF THE INVENTION

Figure 1:
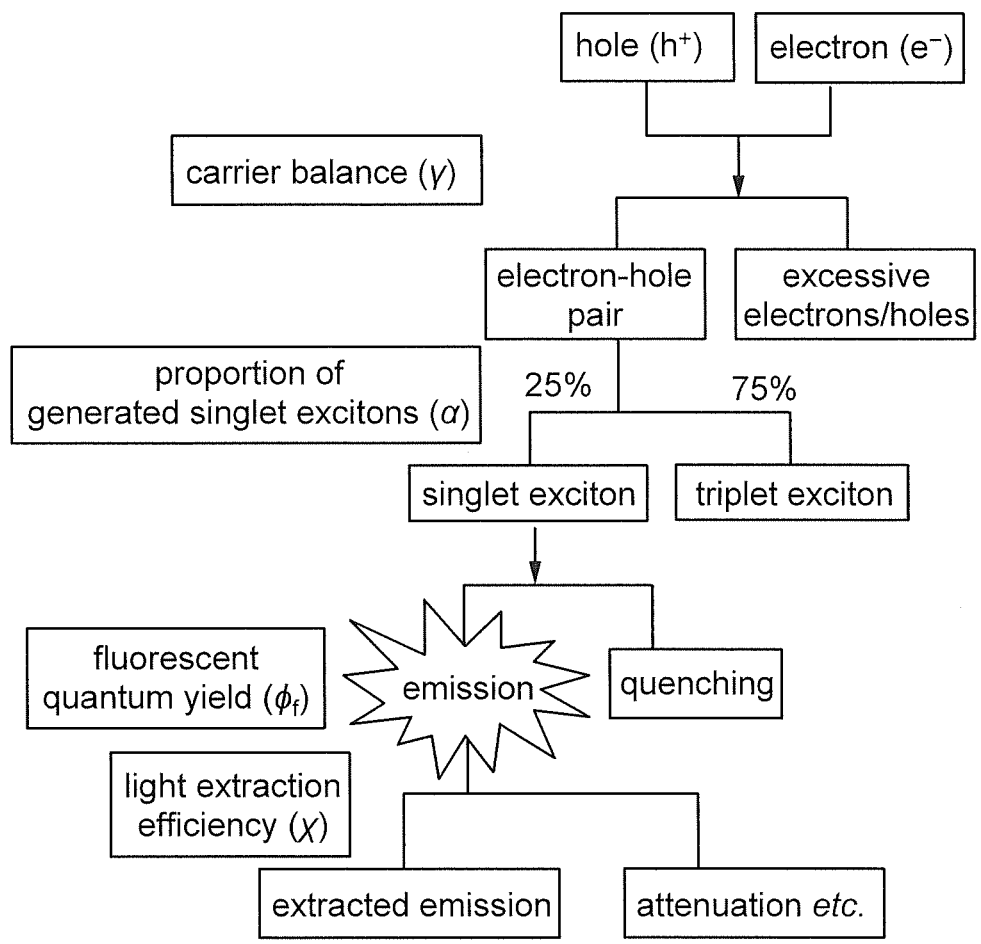
FIG. 1 is a flow chart showing how to calculate the external quantum efficiency of a fluorescent light-emitting element.

Embodiments of the present invention will be described in detail below with reference to the drawings. Note that one embodiment of the present invention is not limited to the following description, and it will be readily appreciated by those skilled in the art that the modes and details can be changed in various ways without departing from the spirit and the scope of the present invention. Thus, the present invention should not be construed as being limited to the description in the following embodiments.

The process from carrier recombination to light emission of an organic EL element that emits fluorescence is described with reference to FIG. 1. First, voltage is applied to the organic EL element, and holes and electrons are injected from an anode and a cathode, respectively, into an EL layer. The injected carriers (holes and electrons) are transported in the EL layer to a light-emitting layer and recombined in a certain area. The proportion of this recombination is called carrier balance (γ). An organic material is excited by energy due to the carrier recombination, and the generation ratio of singlet excitons to triplet excitons is 1:3. This ratio is referred to as the proportion of generated singlet excitons (α). Singlet excitons generated in a light-emitting material emit light in the fluorescent quantum yield ($\phi_f$) of the organic compound. Singlet excitons generated in other organic compounds give energy to the light-emitting material, and then the singlet excitons in the organic compound emit light in the fluorescent quantum yield ($\phi_f$). The proportion of light that is emitted in this manner and observed outside the light-emitting element is the light extraction efficiency (χ) of the organic EL element. The external quantum efficiency ($\mu_{ext}$) of a fluorescent light-emitting element is a product of the carrier balance (γ), the proportion of generated singlet excitons (α), the fluorescent quantum yield ($\phi_f$), and the light extraction efficiency (χ) and represented by Formula (1).

[Formula 1]

$$\text{External quantum efficiency}(\mu_{ext}) = \chi \cdot \phi_f \cdot \alpha \cdot \gamma \quad (1)$$

In the above formula, $\phi_f$ is a value depending on a light-emitting material, and thus, light-emitting materials have their respective values for $\phi_f$. In addition, γ can be assumed to be substantially 1 in an EL element having a stacked structure. Therefore, when the same material is used, terms which can be adjusted to improve the emission efficiency depending on the element structure correspond to the following two terms, i.e., the light extraction efficiency (χ) and the proportion of generated singlet excitons (α).

The proportion of generated singlet excitons (α) can be improved by a mechanism which can up-convert a triplet exciton to a singlet exciton, such as triplet-triplet annihilation (TTA).

The light extraction efficiency (χ) is generally 20% to 30% in an organic EL element over a glass substrate, although it depends on the structure or stacked layers of a light-emitting device. However, the above value is based on the assumption that light emission is isotropic; therefore, this value changes when light emission is anisotropic.

Light emission of a light-emitting material is generated in the direction perpendicular to the transition dipole moment of a molecule. Accordingly, the light extraction efficiency (χ) can be improved by controlling the orientation state of the molecule.

As a method for evaluating the orientation state of a molecule in an amorphous organic thin film, a method using spectroscopic ellipsometry is given. In this method, the refractive index (n) and the extinction coefficient (k) of an organic material are measured to roughly analyze the orientation state. It is practically reported that a long linear molecule or a planar molecule in a material used for a light-emitting element has an orientation parallel to the surface of a thin film (see Non-Patent Document 1).

However, a practical light-emitting element has a stacked structure of a plurality of organic thin films, and a small amount of a light-emitting material is dispersed in a host material. Therefore, the extinction coefficient (k) of a light-emitting material cannot be obtained accurately in a practical light-emitting element, and it is difficult to evaluate the orientation state of a molecule by the above method in the case where the concentration of a light-emitting material is lower than or equal to 10 wt % in a light-emitting layer.

In view of the above, the inventors of the present invention employed a method for estimating the orientation state of a molecule according to the emission state of a light-emitting element. The radiation angle dependence of the emission intensity (spatial emission pattern) of the light-emitting element depends on the direction of an average transition dipole of the light-emitting material. If this spatial distribution can be analyzed, the orientation state of the light-emitting element can be obtained. In this method, light emission of the light-emitting element is observed and analyzed; thus, as long as the light-emitting material emits light, it is possible to obtain the orientation state of the light-emitting material in the light-emitting layer even when the concentration of the material is low.

In practice, the measured angle dependence of the emission intensity and the angle dependence of the emission intensity calculated by assuming, with a device simulator, a parameter a (see Formula (2) below) which represents the orientation state of a light-emitting molecule are compared; in this manner, an appropriate value of the parameter a which represents the orientation state of a molecule can be estimated to obtain the orientation state of a light-emitting substance in a light-emitting element (see Non-Patent Document 2). The inventors of the present invention also focused their attention to the shape of the emission spectrum obtained by the device simulator, and compared the measured and calculated values of the shape of the emission spectrum and a change in the shape of the emission spectrum depending on the angle to predict appropriate values. As the emission intensity in the measurement and simulation, not the emission intensity at a particular wavelength but the integrated intensity of the emission spectrum is used. By these methods which the inventors of the present invention employed, the parameter a can be estimated highly accurately, unlike in the method disclosed in Non-Patent Document 2.

Figure 2:
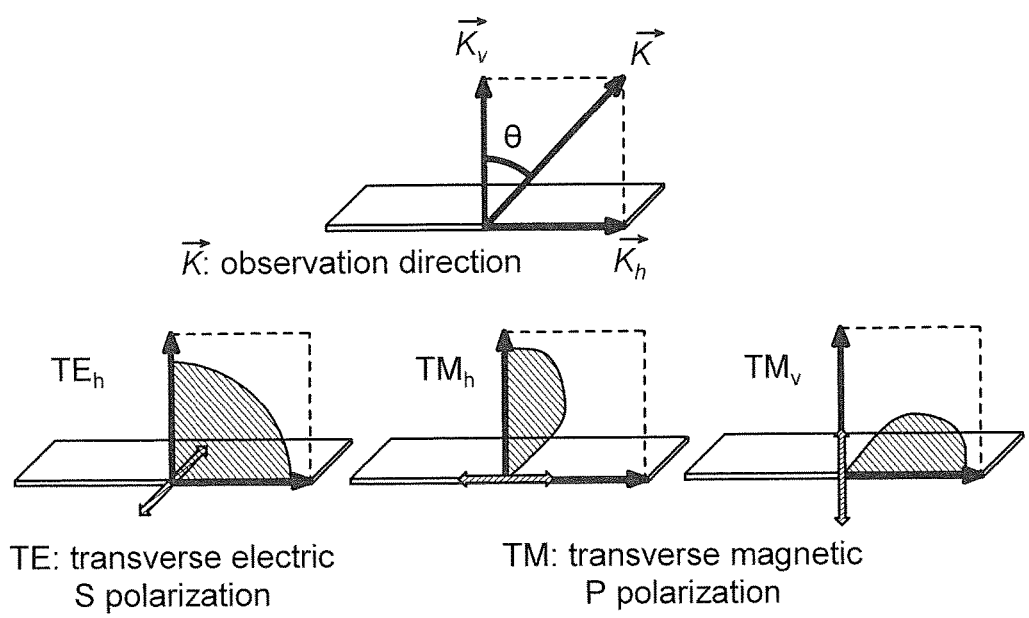
FIG. 2 shows a variation in emission intensity depending on the direction of a transition dipole and the observation angle.

Next, the parameter a which represents the orientation state of a molecule is described. FIG. 2 shows a relation between the observation direction of a measurement device in measuring the spatial distribution of the emission intensity and components of transition dipoles which are orthogonal to each other over a substrate. As shown in FIG. 2, light emission from average transition dipoles in a light-emitting material in a light-emitting layer (light emission practically observed from a light-emitting element) is decomposed into light emission from transition dipoles of a component in the x-axis direction (TEh component), a component in the y-axis direction (TMh component), and a component in the z-axis direction (TMv component). Note that these directions are orthogonal to each other. In other words, it is assumed that three kinds of orientation states of transition dipoles in the x-axis direction, the y-axis direction, and the z-axis direction exist at a certain ratio. In that case, an emission pattern of a light-emitting element is determined by adding light emission from these transition dipoles. As described later, the parameter a relates to the above ratio.

Light is emitted from the molecule in the direction perpendicular to the transition dipole moment (a direction in a perpendicular plane) as described above. Among the components divided into three directions, the TEh component and the TMh component (the x-axis direction and the y-axis direction) are transition dipoles parallel to the substrate surface and their emission directions are perpendicular to the substrate, so that light emission from the TEh component and the TMh component can be easily extracted. On the other hand, the TMv component (the z-axis direction) is a transition dipole perpendicular to the substrate surface and its emission direction is parallel to the substrate, so that light emission from the TMv component is not easily extracted.

In FIG. 2, a figure which extends from the center of an arrow that represents the orientation of the transition dipole of each component is a schematic figure which represents the emission intensity that is detected by the detector, when the direction of the detector is changed from front of the substrate ($\theta=0°$) to parallel to the substrate ($\theta=90°$). The vertical distance from the center is proportional to the intensity.

Since the detector is located in the direction in which light is emitted, the intensity of detected light of the TEh component (i.e., the vertical distance from the center of the arrow of the figure which extends from the center of the arrow in FIG. 2) is constant, even when the angle of the substrate is changed, and the figure which extends from the center of the arrow has a fan shape. On the other hand, the figures which extend from the centers of the arrows of the TMh component and the TMv component have distorted fan shapes, which indicates that the intensity of detected light is greatly changed depending on the angle $\theta$ of the detector to the substrate. As shown in FIG. 2, the TMh component has high intensity when $\theta$ is small (in a direction closer to the front direction of the substrate), whereas the TMv component has high intensity when $\theta$ is large (in a direction closer to the direction parallel to the substrate). In that case, the emission intensity measured by the measurement device (the emission intensity at a wavelength $\lambda$ and at an angle $\theta$: $I_\lambda(\theta,\lambda)$) can be represented by Formula (2).

[Formula 2]

$$I_\lambda(\theta,\lambda)=a\cdot I_{TMv}+(1-a)\cdot(I_{TMh}+I_{TEh}) \quad (2)$$

In the above formula, $I_{TMv}$, $I_{TMh}$, and $I_{TEh}$ represent spatial intensity distribution of light emitted from the transition dipoles arranged as shown in FIG. 2, and a represents the proportion of transition dipoles arranged perpendicular to the film surface (the TMv component). In addition, 1−a represents the proportion of transition dipoles arranged parallel to the film surface (the TMh and TEh components). That is, a can also be regarded as a parameter which represents the orientation of transition dipoles of light-emitting molecules.

In the above formula, when the transition dipoles are arranged only in the direction completely parallel to the substrate, the TMv component is eliminated and a is 0. In contrast, when the transition dipoles are arranged only in the direction perpendicular to the substrate, a is 1. When the directions of the transition dipoles are not the same, the ratio of the components of the transition dipoles is supposed to be isotropic, i.e., x-axis:y-axis:z-axis=1:1:1, so that the ratio of the component perpendicular to the substrate (the TMv component) to the components parallel to the substrate (the TMh and TEh components) is 1:2 and a is ⅓ (approximately 0.33).

As described above, $I_{TEh}$ is constant independent of the angle; however, $I_{TMh}$ and $I_{TMv}$ change depending on the angle ($\theta$) of the substrate to the measurement device. Thus, by measuring the emission intensity while changing $\theta$, a can be obtained from the change in $I_{TMh}$ and $I_{TMv}$ depending on $\theta$.

In that case, $I_{TEh}$ which does not change depending on the angle hinders the measurement. The amplitude direction of an electric field of emitted light is the same as the direction of the transition dipole moment, and $I_{TEh}$ is an S-wave and $I_{TMv}$ and $I_{TMh}$ are P-waves. Thus, by disposing a linear polarizer in the direction perpendicular to the substrate surface, measurement can be performed under the condition where the TEh component is excluded.

The TMh component and the TMv component are compared. The emission direction of the TMh component is mainly perpendicular to the substrate and the emission direction of the TMv component is mainly parallel to the substrate; in a light-emitting element in which light emission is obtained from a solid, a large part of light emission from the TMv component is totally reflected and cannot be extracted to the outside. On the other hand, light emission from the TMh component is more easily extracted to the outside than light emission from the TMv component. Furthermore, in a light-emitting element in which the thickness is optically optimized, light emission from the TMh component whose emission direction is mainly perpendicular to the substrate is intensified through interference, so that the emission intensity of the TMh component is increased (thus, the emission efficiency is maximized). That is, unless the parameter a representing the orientation is very close to 1, a difference between the emission intensity of the TMv component and that of the TMh component is very large in the light-emitting element in which the thickness is optically optimized. That is, in the light-emitting element in which the emission efficiency is maximized, most light emission which is observed depends on the TMh component. In the case where the difference between the emission intensity of the TMh component and that of the TMv component is large as described above, it is difficult to experimentally extract light emission from the component which has lower intensity (namely the TMv component) from the distribution of the emission intensity depending on the angle.

Thus, in this embodiment, the emission intensity in the front direction of the substrate is suppressed as much as possible by utilizing an interference effect (that is, light emission from the TMh component is reduced as much as possible by utilizing an interference effect), so that the ratio of the TMh component to the TMv component, i.e., the parameter a, can be easily obtained. For this purpose, an element in which the thickness is adjusted is prepared for measurement. Specifically, an element is fabricated and used for measurement, in which the luminance in the front direction of the substrate is lowered by setting the distance between a light-emitting region and a cathode to nλ/2. In general, the thickness is adjusted in such a manner that the thickness of an electron-transport layer to which an alkali metal is added is increased. However, since there is a limitation on the conductivity of the film, the drive voltage might be increased or the carrier balance might be poor. Accordingly, in order to adjust the thickness, it is preferable to use a composite material of a material having a hole-transport property and a material having an acceptor property with respect to the material having a hole-transport property. It is preferable to use the composite material for a hole-injection layer in an EL layer or a layer between an electron-injection layer and a cathode.

As the material having a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the substance having a hole-transport property which is used for the composite material is preferably a substance having a hole mobility of $10^{-6}$ cm$^2$/Vs or higher. Examples of organic compounds that can be used as the material having a hole-transport property in the composite material are specifically given below.

Examples of the material having a hole-transport property that can be used for the composite material include aromatic amine compounds such as N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B); carbazole derivatives such as 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene; and aromatic hydrocarbons such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples are pentacene, coronene, and the like. Aromatic hydrocarbon having a vinyl skeleton may also be used and examples thereof are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

In particular, as the material having a hole-transport property, a dibenzothiophene derivative or a dibenzofuran derivative such as 4-[4-(9-phenyl-9H-fluoren-9-yl)phenyl]-6-phenyldibenzothiophene (abbreviation: DBTFLP-IV), 1,3,5-tri(dibenzothiophen-4-yl)-benzene (abbreviation: DBT3P-II), 4,4'-(biphenyl-2,2'-diyl)-bis-dibenzothiophene (abbreviation: oDBTBP-II), 2,8-diphenyl-4-[4-(9-phenyl-9H-fluoren-9-yl)phenyl]dibenzothiophene (abbreviation: DBTFLP-III), 4-[3-(triphenylen-2-yl)phenyl]dibenzothiophene (abbreviation: mDBTPTp-II), 3,6-di-(dibenzothiophen-4-yl)-9-phenyl-9H-carbazole (abbreviation: DBT2PC-II), 4-[3-(9,10-diphenyl-2-anthryl)phenyl]dibenzothiophene (abbreviation: 2mDBTPPA-II), 4-[3-(9,10-diphenyl-2-anthryl)phenyl]dibenzofuran (abbreviation: 2mDBFPPA-II), or 4-[4-(9-phenylanthracen-10-yl)phenyl]dibenzothiophene (abbreviation: mDBTPA-II), or a hydrocarbon compound in which a substituent is bonded to a naphthalene skeleton, a phenanthrene skeleton, or a triphenylene skeleton and in which the molecular weight is 350 to 2000, such as 1-[3,5-di(naphthalen-1-yl)phenyl]naphthalene (abbreviation: N3P), 9-[3,5-di(phenanthren-9-yl)phenyl]phenanthrene (abbreviation: Pn3P), 1,2,3,4-tetraphenylnaphthalene (abbreviation: P4N), 2-[3,5-di-(naphthalen-2-yl)-phenyl]-naphthalene (abbreviation: (3N3P), or 9,9'-(biphenyl-3,3'-diyl)-diphenanthrene (abbreviation: mPnBP) can be used. A composite material including such a material exhibits no absorption ranging from a visible light region to a near-infrared region. The measurement results of a light-emitting element containing the composite material almost correspond to the calculation results, that is, a can be accurately obtained.

Other examples are high molecular compounds such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl)methacrylamide] (abbreviation: PTPDMA), and poly[N,N'-bis(4-butylphenyl)-N,N'-bis(phenyl)benzidine] (abbreviation: poly-TPD).

As examples of the substance having an acceptor property, 7,7,8,8-tetracyano-2,3,5,6-tetrafluoroquinodimethane (abbreviation: $F_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable since it is stable in the air and low in hygroscopic property and is thus easily treated.

The composite material has high conductivity and thus has an advantage in that the drive voltage is unlikely to be increased and the carrier balance can be kept even when the thickness of a film containing the composite material is large.

As described above, a light-emitting element with a partly special structure is used for the measurement. However, by forming a light-emitting layer having a structure similar to that of a general light-emitting element, the evaluation results of the orientation state can also be applied to the orientation state of a light-emitting element with an ordinary structure.

Such a light-emitting element is made to emit light and a linear polarizer is disposed in the direction perpendicular to the substrate; in this manner, the angle dependence of the emission intensity is measured. The emission intensity may be represented as an intensity at a certain wavelength but is preferably represented as a value obtained by integrating the emission spectrum intensity in one embodiment of the present invention, because a more accurate examination can be performed.

This experimental value is compared with a calculation result obtained by an organic device simulator (a semiconducting emissive thin film optics simulator, namely setfos, produced by Cybernet Systems Co., Ltd.), so that a of the light-emitting element can be obtained. In this calculation, the spectrum shape of a light-emitting material, the thickness of a stacked structure, the refractive index, the extinction efficiency, and the position and the width of a light-emitting region are input to calculate the emission intensity (spectrum) depending on the angle $\theta$, which corresponds to an input given parameter a.

Note that the position of the light-emitting region cannot be measured and is thus assumed. The position of the light-emitting region can be assumed empirically in consideration of a carrier-transport property or the like of the light-emitting layer. However, the following method is preferable to a method of fixing the position of the light-emitting region to one position in the thickness direction: first, a light-emitting position where the recombination probability is supposed to be the highest (e.g., the vicinity of the interface between a hole-transport layer and the light-emitting layer when, for example, an electron-transport property of the light-emitting layer is higher than a hole-transport property thereof) is fixed, and calculation is performed assuming that the light-emitting region spreads such that the recombination probability is decreased exponentially from the light-emitting position. Through this method, favorable calculation results of the spectrum shape close to the measured one can be obtained.

The inventors of the present invention found that a favorable light-emitting element with extremely high emission efficiency can be obtained by setting a calculated by the above method to less than or equal to 0.2, preferably greater than or equal to 0 and less than or equal to 0.2.

The light extraction efficiency in each orientation state is discussed. As compared with the case where the transition dipole moment has a random orientation (a=⅓≈0.33), transition dipoles of ⅓ of molecules which have been perpendicular to the substrate in a random orientation are parallel to the substrate in the case where the transition dipole moment has an orientation completely parallel to the substrate (a=0). Therefore, the proportion of the transition dipoles parallel to the substrate surface is 1.5 times the proportion in the random orientation.

As described above, most light emission observed in the optimized light-emitting element is derived from emission components of molecules in the horizontal orientation, and light emission from molecules in the perpendicular orientation (i.e., the TMv component) is relatively weak so as to be negligible. In other words, it is suggested that, in the case of the random orientation, light emission from ⅓ of molecules is not extracted substantially. On the other hand, in the case of a=0, the proportion of transition dipoles parallel to the substrate is 1.5 times the proportion in the random orientation as described above, so that the proportion of molecules contributing to observed light emission and the light extraction efficiency are also approximately 1.5 times those in the random orientation.

As described above, in the light-emitting element of one embodiment of the present invention, by setting a to less than or equal to 0.2, more light emission can be extracted to the outside than in the random orientation, so that a light-emitting element with high external quantum efficiency can be provided. In the case of a=0.2, the proportion of transition dipoles in the horizontal orientation is 1.2 times the proportion in the random orientation, so that the light extraction efficiency can also be 1.2 times the one in the random orientation.

Note that an electrode of the light-emitting element is provided parallel to the substrate, so that a transition dipole parallel to the substrate is parallel to a first electrode or a second electrode of the light-emitting element.

A fluorescent light-emitting element in which a light-emitting material is a fluorescent substance has been described as an example; however, the above description can also apply to a phosphorescent light-emitting element in which a light-emitting material is a phosphorescent substance. When a light-emitting material is a phosphorescent substance, a light-emitting element with extremely high emission efficiency can be obtained. A phosphorescent substance is preferably an iridium complex. In a phosphorescent light-emitting element including a light-emitting layer in which a is less than or equal to 0.2, the efficiency can be easily high, that is, the external quantum efficiency can be easily higher than or equal to 25%. When the phosphorescent quantum yield of the light-emitting material is very high (e.g., higher than or equal to 0.84, preferably higher than or equal to 0.9), it is possible to provide a light-emitting element which has extremely high efficiency, that is, an external quantum efficiency that exceeds the theoretical limit, higher than or equal to 30%. In order to efficiently transfer energy or to reduce the drive voltage, the following structure of a phosphorescent light-emitting element is preferable: a light-emitting layer contains a third substance in addition to a host material and a light-emitting material, and the host material and the third substance form an exciplex.

When a light-emitting material is a fluorescent material, the material is preferably a substance having a condensed aromatic hydrocarbon skeleton for the molecular orientation. A light-emitting element including a light-emitting layer in which a is less than or equal to 0.2 has a light extraction efficiency which is increased 1.2 times. When the fluorescent quantum yield of a light-emitting material of a fluorescent light-emitting element is very high (e.g., higher than or equal to 0.84, preferably higher than or equal to 0.9), it is possible to provide a light-emitting element which has high efficiency, that is, an external quantum efficiency that exceeds the theoretical limit, higher than or equal to 7.5%. A light-emitting element having a mechanism such as TTA in addition to the above structure can have very high efficiency, that is, an external quantum efficiency of 10% or higher. In such a light-emitting element also having TTA, a delayed fluorescent component is observed.

<<Light-Emitting Element>>

Figure 3A:
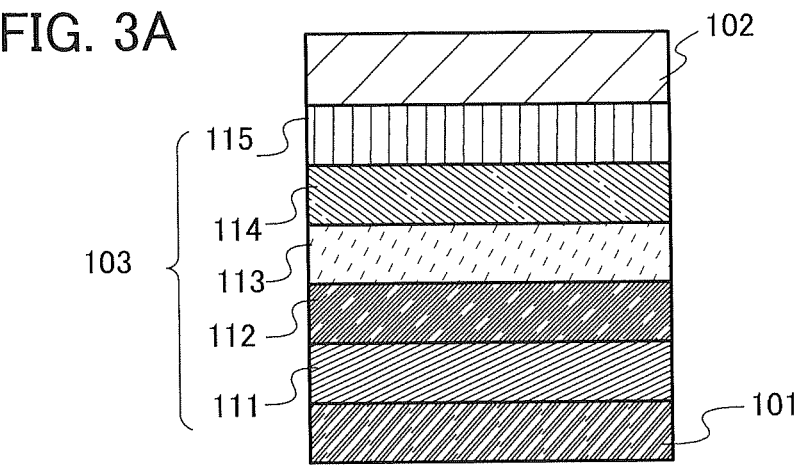
FIGS. 3A to 3C are each a conceptual diagram of a light-emitting element.

Next, an example of a light-emitting element of one embodiment of the present invention is described in detail below with reference to FIG. 3A.

In this embodiment, the light-emitting element includes a pair of electrodes (a first electrode 101 and a second electrode 102), and an EL layer 103 provided between the first electrode 101 and the second electrode 102. Note that the first electrode 101 functions as an anode and the second electrode 102 functions as a cathode.

To function as an anode, the first electrode 101 is preferably formed using any of metals, alloys, conductive compounds having a high work function (specifically, a work function of 4.0 eV or higher), mixtures thereof, and the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Films of these electrically conductive metal oxides are usually formed by a sputtering method but may also be formed by application of a sol-gel method or the like. For example, a film of indium oxide-zinc oxide is formed by a sputtering method using a target obtained by adding 1 wt % to 20 wt % of zinc oxide to indium oxide. A film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Other examples are gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), and the like. Graphene can also be used. Note that when a composite material described later is used for a layer which is in contact with the first electrode 101 in the EL layer 103, an electrode material can be selected regardless of its work function.

The EL layer 103 has a stacked structure and includes at least a light-emitting layer. Examples of layers included in the EL layer 103 other than the light-emitting layer are a hole-injection layer, a hole-transport layer, an electron-transport layer, an electron-injection layer, a carrier-blocking layer, and an intermediate layer. The light-emitting element can be formed by combining these layers as appropriate. In this embodiment, the EL layer 103 has a structure in which a hole-injection layer 111, a hole-transport layer 112, a light-emitting layer 113, an electron-transport layer 114, and an electron-injection layer 115 are stacked in this order over the first electrode 101. Specific examples of the materials forming the layers are given below.

The hole-injection layer 111 is a layer containing a substance having a high hole-injection property. The hole-injection layer 111 can be formed using molybdenum oxide, vanadium oxide, ruthenium oxide, tungsten oxide, manganese oxide, or the like. Alternatively, the hole-injection layer 111 can be formed using a phthalocyanine-based compound such as phthalocyanine (abbreviation: $H_2Pc$) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD), a high molecule such as poly(3,4-ethylenedioxythiophene)/poly (styrenesulfonic acid) (PEDOT/PSS), 7,7,8,8-tetracyano-2,3,5,6-tetrafluoroquinodimethane (abbreviation: $F_4$-TCNQ), chloranil, or the like.

Alternatively, a composite material in which a substance having a hole-transport property contains a substance having an acceptor property can be used for the hole-injection layer 111. This composite material is the same as the above-described composite material which is preferably used for adjusting the thickness of the light-emitting element; thus, its description is omitted. By using the composite material for the hole-injection layer, the material of the first electrode can be selected regardless of its work function.

By providing the hole-injection layer 111, a high hole-injection property can be achieved to allow the light-emitting element to be driven at low voltage.

The hole-transport layer 112 is a layer containing a substance having a hole-transport property. Examples of the substance having a hole-transport property include aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4"-tris(N,N'-diphenylamino) triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), and 4-phenyl-4'-(9-phenylfluoren-9-yl)triphenylamine (abbreviation: BPAFLP). The substances listed here have high hole-transport properties and are mainly ones that have a hole mobility of $10^{-6}$ $cm^2/Vs$ or higher. An organic compound given as an example of the substance having a hole-transport property in the composite material described above can also be used for the hole-transport layer 112. Note that the layer that contains a substance having a hole-transport property is not limited to a single layer, and may be a stack of two or more layers including any of the above substances.

The light-emitting layer 113 may be a layer that emits fluorescence, a layer that emits phosphorescence, or a layer that emits thermally activated delayed fluorescence (TADF). Furthermore, the light-emitting layer 113 may be a single layer or include a plurality of layers containing different light-emitting substances. In the case where the light-emitting layer including a plurality of layers is formed, a layer containing a phosphorescent substance and a layer containing a fluorescent substance may be stacked. In that case, an exciplex described later is preferably utilized in the layer containing a phosphorescent substance.

As a fluorescent substance, any of the following substances can be used, for example. Fluorescent substances other than those given below can also be used. Specific examples include N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-diphenyl-N,N'-bis[3-(9-phenyl-9H-fluoren-9-yl)phenyl]pyrene-1,6-diamine (abbreviation: 1,6mFLPAPrn), N,N'-bis(2,6-dimethylphenyl)-N,N'-bis[3-(9-phenyl-9H-fluoren-9-yl)phenyl]pyrene-1,6-diamine (abbreviation: 1,6oDMemFLPAPrn), N,N'-bis[4-(dibenzofuran-4-yl)phenyl]-N,N'-diphenyl-pyrene-1,6-diamine (abbreviation: 1,6FrBAPrn-II), N,N'-bis[3-(dibenzofuran-4-yl)phenyl]-N,N'-diphenyl-pyrene-1,6-diamine (abbreviation: 1,6mFrBAPrn-II), N,N'-(pyrene-1,6-diyl)bis[(N-phenylbenzo[b]naphtho[1,2-d]furan)-8-amine] (abbreviation: 1,6BnfAPrn-02), N,N'-(pyrene-1,6-diyl)bis[(6,N-diphenylbenzo[b]naphtho[1,2-d]furan)-8-amine] (abbreviation: 1,6BnfAPrn-03), 9,10-bis[N-phenyl-N-(9-phenylcarbazol-3-yl)amino]anthracene (abbreviation: PCA2A), and coumarin 545T. Condensed aromatic diamine compounds typified by pyrenediamine compounds, such as 1,6FLPAPrn and 1,6mMemFLPAPrn, are preferable because of their high hole-trapping properties, high emission efficiency, high reliability, and easiness in the molecular orientation.

Examples of a material which can be used as a phosphorescent substance in the light-emitting layer 113 are as follows: an organometallic iridium complex having an azole (in particular, a triazole or imidazole) skeleton, such as tris{2-[4-(2-adamantyl)-3-methyl-4H-1,2,4-triazol-5-yl-κN]phenyl-κC}iridium(III) (abbreviation: [Ir(Mptz-Adm2)$_3$]), tris{2-[4-(4-cyano-2,6-diisobutylphenyl)-5-(2-methylphenyl)-4H-1,2,4-triazol-3-yl-κN$^2$]phenyl-κC}iridium(III) (abbreviation: Ir(mpptz-diBuCNp)$_3$), tris{2-[4-(4-cyano-2,6-dimethylphenyl)-5-(2-methylphenyl)-4H-1,2,4-triazol-3-yl-κN$^2$]phenyl-κC}iridium(III) (abbreviation: Ir(mpptz-dmCNp)$_3$), or tris{2-[1-(4-cyano-2,6-diisobutylphenyl)-1H-imidazol-2-yl-κN$^3$]phenyl-κC}iridium(III) (abbreviation: Ir(pim-diBuCNp)$_3$), an organometallic iridium complex having a pyrimidine skeleton, such as (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis(4,6-diphenylpyrimidinato)iridium(III) (abbreviation: [Ir(dppm)$_2$(acac)]), (acetylacetonato)bis(4,5,6-triphenylpyrimidinato)iridium(III) (abbreviation: [Ir(tppm)$_2$(acac)]), bis{2-[6-(3,5-dimethylphenyl)-4-pyrimidinyl-κN3]-4,6-dimethylphenyl-κC}(2,6-dimethyl-3,5-heptanedionato-κ$^2$O,O')iridium(III) (abbreviation: [Ir(dmdppm)$_2$(dibm)]), or bis{2-[6-(3,5-dimethylphenyl)-4-pyrimidinyl-κN3]-4,6-dimethylphenyl-κC}(2,2',6,6'-tetramethyl-3,5-heptanedionato-κ$^2$O,O')iridium(III) (abbreviation: [Ir(dmdppm)$_2$(dpm)]), and an organometallic iridium complex having a pyrazine skeleton, such as bis(2,3,5-triphenylpyrazinato)(dipivaloylmethanato) iridium(III) (abbreviation: [Ir(tppr)$_2$(dpm)]), bis{4,6-dimethyl-2-[5-(2,6-dimethylphenyl)-3-(3,5-dimethylphenyl)-2-pyrazinyl-κN]phenyl-κC}(2,4-pentanedionato-κ$^2$O,O') iridium(III) (abbreviation: [Ir(dmdppr-dmp)$_2$(acac)]), bis{4,6-dimethyl-2-[5-(2,6-dimethylphenyl)-3-(3,5-dimethylphenyl)-2-pyrazinyl-κN]phenyl-κC}(2,8-dimethyl-4,6-nonanedionato-κ$^2$O,O')iridium(III) (abbreviation: [Ir(dmdppr-dmp)$_2$(divm)]), bis{4,6-dimethyl-2-[5-(2,6-dimethylphenyl)-3-(3,5-dimethylphenyl)-2-pyrazinyl-κN]phenyl-κC}(2,2',6,6'-tetramethyl-3,5-heptanedionato-κ$^2$O,O')iridium(III) (abbreviation: [Ir(dmdppr-dmp)$_2$(dpm)]), or bis{4,6-dimethyl-2-[5-(2,5-dimethylphenyl)-3-(3,5-dimethylphenyl)-2-pyrazinyl-κN]phenyl-κC}(2,2,6,6-tetramethyl-3,5-heptanedionato-k$^2$O,O')iridium(III) (abbreviation: [Ir(dmdppr-25dmp)$_2$(dpm)]). These organometallic iridium complexes are preferable because of their high emission efficiency, high reliability, and easiness in the molecular orientation.

As well as the above phosphorescent compounds, a variety of phosphorescent materials may be selected and used.

Examples of the TADF material include a heterocyclic compound having both a π-electron rich heteroaromatic ring and a t-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA). The heterocyclic compound is preferable because of having high electron-transport and hole-transport properties owing to a π-electron rich heteroaromatic ring and a π-electron deficient heteroaromatic ring. Note that a substance in which the π-electron rich heteroaromatic ring is directly bonded to the π-electron deficient heteroaromatic ring is particularly preferably used because the donor property of the t-electron rich heteroaromatic ring and the acceptor property of the π-electron deficient heteroaromatic ring are both increased, the energy difference between the S$_1$ level and the T$_1$ level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring.

As a host material of the light-emitting layer, various carrier-transport materials such as a material having an electron-transport property or a material having a hole-transport property can be used.

Examples of the material having an electron-transport property include a metal complex such as bis(10-hydroxybenzo[h]quinolinato)beryllium(II) (abbreviation: BeBq$_2$), bis(2-methyl-8-quinolinolato) (4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ); a heterocyclic compound having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl) phenyl]-9H-carbazole (abbreviation: CO11), 2,2',2"-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II); a heterocyclic compound having a diazine skeleton, such as 2-[3-(dibenzothiophen-4-yl)phenyl]dibenzo[fh]quinoxaline (abbreviation: 2mDBTPDBq-II), 2-[3'-(dibenzothiophen-4-yl)biphenyl-3-yl]dibenzo[fh]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyrimidine (abbreviation: 4,6mDBTP2Pm-II); and a heterocyclic compound having a pyridine skeleton, such as 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB). Among the above materials, a heterocyclic compound having a diazine skeleton and a heterocyclic compound having a pyridine skeleton have high reliability and are thus preferable. Specifically, a heterocyclic compound having a diazine (pyrimidine or pyrazine) skeleton has a high electron-transport property to contribute to a reduction in drive voltage.

Examples of materials having a hole-transport property include a compound having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF); a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV); and a compound having a furan skeleton, such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II). Among the above materials, a compound having an aromatic amine skeleton and a compound having a carbazole skeleton are preferable because these compounds are highly reliable and have high hole-transport properties to contribute to a reduction in drive voltage. Hole-transport materials can be selected from a variety of substances as well as from the hole-transport materials given above.

In the case of using a fluorescent substance as a light-emitting substance, materials having an anthracene skeleton, such as 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)-biphenyl-4'-yl}-anthracene (abbreviation: FLPPA), are preferably used. The use of a substance having an anthracene skeleton as a host material for a fluorescent substance makes it possible to obtain a light-emitting layer with high emission efficiency and high durability. In particular, CzPA, cgDBCzPA, 2mBnfPPA, and PCzPA are preferable because of their excellent characteristics.

Note that a host material may be a mixture of a plurality of kinds of substances, and in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

These mixed host materials may form an exciplex. When a combination of these materials is selected so as to form an exciplex that exhibits light emission whose wavelength overlaps with the wavelength of a lowest-energy-side absorption band of the fluorescent substance, the phosphorescent substance, or the TADF material, energy is transferred smoothly and light emission can be obtained efficiently. Such a structure is preferable in that the drive voltage can be reduced.

Since a which represents the orientation state of a light-emitting material is unlikely to be influenced by the kind or number of host materials, any material may be selected as a host material.

The light-emitting layer 113 having the above-described structure can be formed by co-evaporation using a vacuum evaporation method. In that case, an effective atmosphere for a chamber is as follows: the ratio of the partial pressure of carbon dioxide with respect to the total pressure in the chamber, which is measured by a quadrupole mass analyzer (Q-mass) disposed in the evaporation chamber, is higher than that in the air. In the air, the percentage of the partial pressure of carbon dioxide with respect to the total pressure (i.e., volume ratio) is approximately 0.03%. A light-emitting element having an orientation state in which a of a light-emitting material is less than or equal to 0.2 can be fabricated in such a manner that a light-emitting layer is formed in a vacuum chamber in a reduced pressure atmosphere in the state where the percentage of the partial pressure of carbon dioxide with respect to the total pressure is higher than 0.03%, preferably higher than or equal to 0.1%. Since carbon dioxide hinders a carrier-transport property, its percentage is preferably lower than or equal to 10%.

The electron-transport layer 114 contains a substance having an electron-transport property. As the substance having an electron-transport property, the materials having an electron-transport property or having an anthracene skeleton, which are described above as materials for the host material, can be used.

A layer for controlling the transport of electron carriers may be provided between the electron-transport layer and the light-emitting layer. This is a layer formed by addition of a small amount of a substance having a high electron-trapping property to a material having a high electron-transport property as described above, and the layer is capable of adjusting the carrier balance by suppressing the transport of electron carriers. Such a structure is very effective in preventing a problem (such as a reduction in element lifetime) caused when electrons pass through the light-emitting layer.

In addition, the electron-injection layer 115 may be provided in contact with the second electrode 102, between the electron-transport layer 114 and the second electrode 102. For the electron-injection layer 115, an alkali metal, an alkaline earth metal, or a compound thereof, such as lithium fluoride (LiF), cesium fluoride (CsF), or calcium fluoride (CaF$_2$), can be used. For example, a layer that is formed using a substance having an electron-transport property and contains an alkali metal, an alkaline earth metal, or a compound thereof can be used. An electride may also be used for the electron-injection layer 115. Examples of the electride include a substance in which electrons are added at high concentration to calcium oxide-aluminum oxide. Note that a layer that is formed using a substance having an electron-transport property and contains an alkali metal or an alkaline earth metal is preferably used for the electron-injection layer 115, in which case electrons are efficiently injected from the second electrode 102.

Figure 3B:
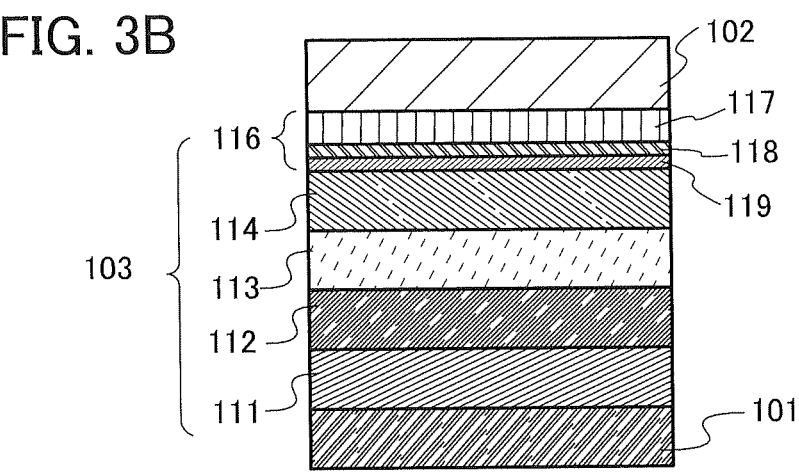

Instead of the electron-injection layer 115, a charge-generation layer 116 may be provided (FIG. 3B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing a hole-transport material. When a potential is applied to the p-type layer 117, electrons are injected into the electron-transport layer 114 and holes are injected into the second electrode 102 functioning as a cathode; thus, the light-emitting element operates.

Note that the charge-generation layer 116 preferably includes either an electron-relay layer 118 or an electron-injection buffer layer 119 or both in addition to the p-type layer 117.

The electron-relay layer 118 contains at least the substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the substance having an acceptor property in the p-type layer 117 and the LUMO level of a substance contained in a layer of the electron-transport layer 114 in contact with the charge-generation layer 116. As a specific value of the energy level, the LUMO level of the substance having an electron-transport property in the electron-relay layer 118 is preferably higher than or equal to −5.0 eV, more preferably higher than or equal to −5.0 eV and lower than or equal to −3.0 eV. Note that as the substance having an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (e.g., an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, or a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)).

For the second electrode 102, any of metals, alloys, electrically conductive compounds having a low work function (specifically, a work function of 3.8 eV or lower), and mixtures thereof, and the like can be used. Specific examples of such a cathode material include elements belonging to Groups 1 and 2 of the periodic table, such as alkali metals (e.g., lithium (Li) and cesium (Cs)), magnesium (Mg), calcium (Ca), and strontium (Sr), alloys thereof (e.g., MgAg and AlLi), rare earth metals such as europium (Eu) and ytterbium (Yb), and alloys thereof. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of its work function. Films of these conductive materials can be formed by a dry method such as a vacuum evaporation method or a sputtering method, an inkjet method, a spin coating method, or the like. In addition, the films of these conductive materials may be formed by a wet method using a sol-gel method, or by a wet method using paste of a metal material.

Any of various methods can be employed for forming the layers other than the light-emitting layer which are included in the EL layer 103 regardless of whether it is a dry method or a wet method. For example, a vacuum evaporation method, a gravure printing method, an offset printing method, a screen printing method, an inkjet method, a spin coating method, or the like may be used.

Here, a method for forming an EL layer 786 by a droplet discharge method is described with reference to FIGS. 4A to 4D. FIGS. 4A to 4D are cross-sectional views illustrating the method for forming the EL layer 786.

Figure 4A:
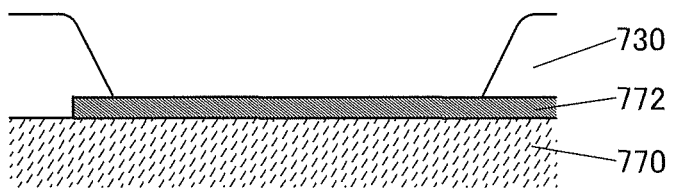
FIGS. 4A to 4D illustrate an example of a method for manufacturing a light-emitting element.
Figure 4B:
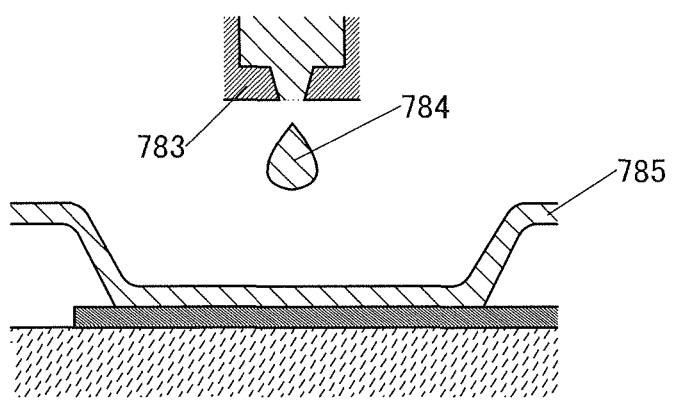

First, a conductive film 772 is formed over a planarization insulating film 770, and an insulating film 730 is formed to cover part of the conductive film 772 (see FIG. 4A).

Then, a droplet 784 is discharged to an exposed portion of the conductive film 772, which is an opening of the insulating film 730, from a droplet discharge apparatus 783, so that a layer 785 containing a composition is formed. The droplet 784 is a composition containing a solvent and is attached to the conductive film 772 (see FIG. 4B).

Note that the step of discharging the droplet 784 may be performed under reduced pressure.

Figure 4C:
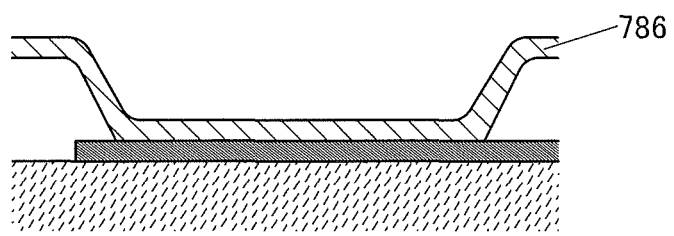

Next, the solvent is removed from the layer 785 containing a composition, and the resulting layer is solidified to form the EL layer 786 (see FIG. 4C).

The solvent may be removed by drying or heating.

Figure 4D:
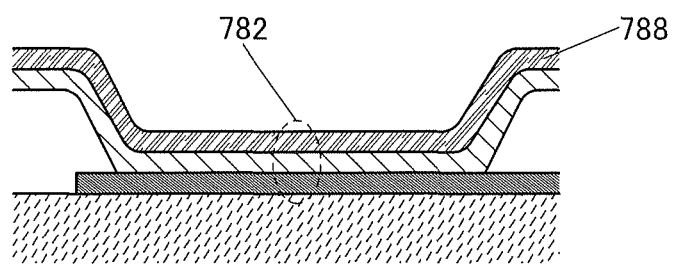

Next, a conductive film 788 is formed over the EL layer 786; thus, a light-emitting element 782 is completed (see FIG. 4D).

When the EL layer 786 is formed by a droplet discharge method as described above, the composition can be selectively discharged; accordingly, waste of material can be reduced. Furthermore, a lithography process or the like for shaping is not needed, and thus, the process can be simplified and cost reduction can be achieved.

The droplet discharge method described above is a general term for a means including a nozzle equipped with a composition discharge outlet or a means to discharge droplets, such as a head having one or a plurality of nozzles.

Figure 5:
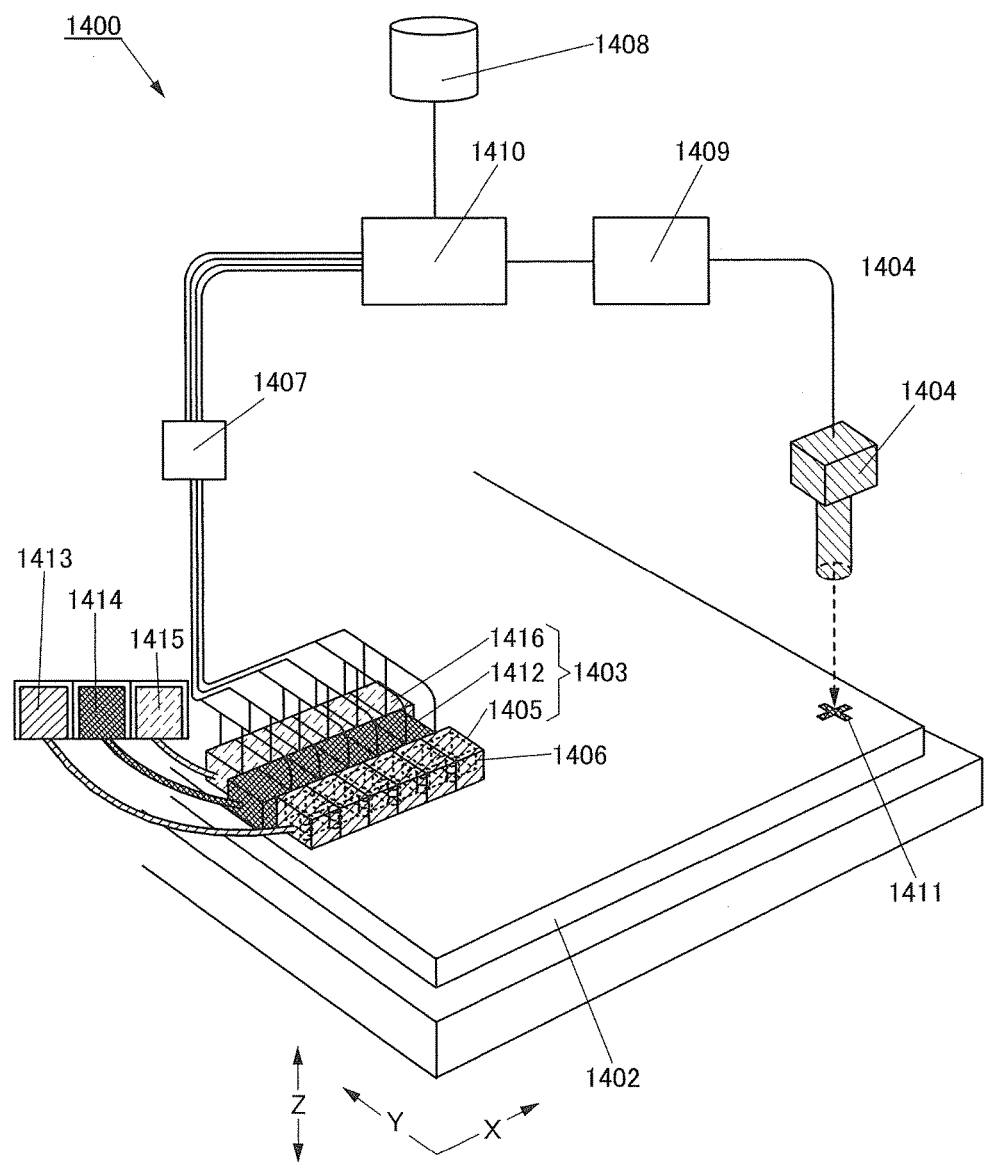
FIG. 5 illustrates an example of a manufacturing apparatus of a light-emitting element.

Next, a droplet discharge apparatus used for the droplet discharge method is described with reference to FIG. 5. FIG. 5 is a conceptual diagram illustrating a droplet discharge apparatus 1400.

The droplet discharge apparatus 1400 includes a droplet discharge means 1403. The droplet discharge means 1403 is equipped with a head 1405, a head 1412, and a head 1416.

The heads 1405 and 1412 are connected to a control means 1407, and this control means 1407 is controlled by a computer 1410; thus, a preprogrammed pattern can be drawn.

The drawing may be conducted at a timing, for example, based on a marker 1411 formed over a substrate 1402. Alternatively, the reference point may be determined on the basis of an outer edge of the substrate 1402. Here, the marker 1411 is detected by an imaging means 1404 and converted into a digital signal by an image processing means 1409. Then, the digital signal is recognized by the computer 1410, and then, a control signal is generated and transmitted to the control means 1407.

An image sensor or the like using a charge coupled device (CCD) or a complementary metal oxide semiconductor (CMOS) can be used as the imaging means 1404. Note that information about a pattern to be formed over the substrate 1402 is stored in a storage medium 1408, and a control signal is transmitted to the control means 1407 on the basis of the information, so that each of the heads 1405, 1412, and 1416 of the droplet discharge means 1403 can be individually controlled. A material to be discharged is supplied to the heads 1405, 1412, and 1416 from material supply sources 1413, 1414, and 1415, respectively, through pipes.

Inside each of the heads 1405, 1412, and 1416, a space as indicated by a dotted line 1406 to be filled with a liquid material and a nozzle which is a discharge outlet are provided. Although not illustrated, an inside structure of the head 1412 is similar to that of the head 1405. When the nozzle sizes of the heads 1405 and 1412 are different from each other, different materials with different widths can be discharged simultaneously. Each head can discharge and draw a plurality of light-emitting materials. In the case of drawing over a large area, the same material can be simultaneously discharged to be drawn from a plurality of nozzles in order to improve throughput. When a large substrate is used, the heads 1405, 1412, and 1416 can freely scan the substrate in the directions indicated by arrows X, Y, and Z in FIG. 5, and a region in which a pattern is drawn can be freely set. Thus, a plurality of the same patterns can be drawn over one substrate.

Furthermore, a step of discharging the composition may be performed under reduced pressure. Also, a substrate may be heated when the composition is discharged. After discharging the composition, either drying or baking or both is performed. Both the drying and baking are heat treatments but different in purpose, temperature, and time period. The steps of drying and baking are performed under normal pressure or under reduced pressure by laser irradiation, rapid thermal annealing, heating using a heating furnace, or the like. Note that the timing of the heat treatment and the number of times of the heat treatment are not particularly limited. The temperature for performing each of the steps of drying and baking in a favorable manner depends on the material of the substrate and the properties of the composition.

In the above-described manner, the EL layer 786 can be formed by the droplet discharge apparatus.

In the case where the EL layer 786 is formed by the droplet discharge apparatus, the following various organic solvents can be used to form a coating composition: benzene, toluene, xylene, mesitylene, tetrahydrofuran, dioxane, ethanol, methanol, n-propanol, isopropanol, n-butanol, t-butanol, acetonitrile, dimethylsulfoxide, dimethylformamide, chloroform, methylene chloride, carbon tetrachloride, ethyl acetate, hexane, cyclohexane, and the like. In particular, less polar benzene derivatives such as benzene, toluene, xylene, and mesitylene are preferable because a solution with a suitable concentration can be obtained and the material contained in ink can be prevented from deteriorating due to oxidation or the like. Furthermore, to achieve a uniform film or a film with a uniform thickness, a solvent with a boiling point of 100° C. or higher is preferably used, and more preferably, toluene, xylene, or mesitylene is used.

Note that the above-described structure can be combined with any of the structures in this embodiment.

In addition, the electrode may be formed by a wet method using a sol-gel method, or by a wet method using paste of a metal material. Furthermore, the electrode may be formed by a dry method such as a sputtering method or a vacuum evaporation method.

Light emission from the light-emitting element is extracted out through one or both of the first electrode 101 and the second electrode 102. Therefore, one or both of the first electrode 101 and the second electrode 102 are formed as a light-transmitting electrode.

The structure of the layers provided between the first electrode 101 and the second electrode 102 is not limited to the above-described structure. Preferably, a light-emitting region where holes and electrons recombine is positioned away from the first electrode 101 and the second electrode 102 so that quenching due to the proximity of the light-emitting region and a metal used for electrodes and carrier-injection layers can be prevented.

Furthermore, in order that the transfer of energy from an exciton generated in the light-emitting layer can be suppressed, preferably, the hole-transport layer and the electron-transport layer which are in contact with the light-emitting layer 113, particularly a carrier-transport layer in contact with a side closer to the recombination region in the light-emitting layer 113, are formed using a substance having a wider band gap than the light-emitting substance of the light-emitting layer or an emission center substance included in the light-emitting layer.

Next, an embodiment of a light-emitting element with a structure in which a plurality of light-emitting units are stacked (this type of light-emitting element is also referred to as a stacked or tandem light-emitting element) is described with reference to FIG. 3C. This light-emitting element includes a plurality of light-emitting units between an anode and a cathode. One light-emitting unit has a structure similar to that of the EL layer 103, which is illustrated in FIG. 3A or 3B. In other words, the light-emitting element illustrated in FIG. 3A or 3B includes a single light-emitting unit, and the light-emitting element illustrated in FIG. 3C includes a plurality of light-emitting units.

Figure 3C:
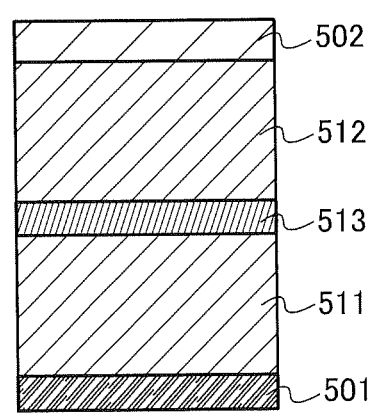

In FIG. 3C, a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond, respectively, to the first electrode 101 and the second electrode 102 illustrated in FIG. 3A, and the materials given in the description for FIG. 3A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the first electrode 501 and the second electrode 502. That is, in FIG. 3C, the charge-generation layer 513 injects electrons into the first light-emitting unit 511 and holes into the second light-emitting unit 512 when a voltage is applied so that the potential of the first electrode becomes higher than the potential of the second electrode.

The charge-generation layer 513 preferably has a structure similar to the structure of the charge-generation layer 116 described with reference to FIG. 3B. The composite material of an organic compound and a metal oxide has a high carrier-injection property and a high carrier-transport property; thus, low-voltage driving and low-current driving can be achieved. Note that when a surface of a light-emitting unit on the anode side is in contact with the charge-generation layer 513, the charge-generation layer 513 can also function as a hole-injection layer in the light-emitting unit and a hole-injection layer is not necessarily formed in the light-emitting unit.

In the case where the electron-injection buffer layer 119 is provided, the electron-injection buffer layer functions as the electron-injection layer in the light-emitting unit on the anode side and the light-emitting unit does not further need an electron-injection layer.

The light-emitting element including two light-emitting units is described with reference to FIG. 3C; however, the present invention can be similarly applied to a light-emitting element in which three or more light-emitting units are stacked. With a plurality of light-emitting units partitioned by the charge-generation layer 513 between a pair of electrodes as in the light-emitting element according to this embodiment, it is possible to provide an element which can emit light with high luminance with the current density kept low and has a long lifetime. Moreover, a light-emitting device of low power consumption, which can be driven at low voltage, can be achieved.

When light-emitting units have different emission colors, light emission of a desired color can be obtained as a whole light-emitting element. For example, it is easy to enable a light-emitting element having two light-emitting units to emit white light as the whole element when the emission colors of the first light-emitting unit are red and green and the emission color of the second light-emitting unit is blue.

<<Micro Optical Resonator (Microcavity) Structure>>

A light-emitting element with a microcavity structure is formed with the use of a reflective electrode and a semi-transmissive and semi-reflective electrode as the pair of electrodes. The reflective electrode and the semi-transmissive and semi-reflective electrode correspond to the first electrode and the second electrode described above. The light-emitting element with a microcavity structure includes at least an EL layer between the reflective electrode and the semi-transmissive and semi-reflective electrode. The EL layer includes at least a light-emitting layer functioning as a light-emitting region.

Light emitted from the light-emitting layer included in the EL layer is reflected and resonated by the reflective electrode and the semi-transmissive and semi-reflective electrode. Note that the reflective electrode has a visible light reflectivity of 40% to 100%, preferably 70% to 100% and a resistivity of $1\times10^{-2}$ $\Omega$cm or lower. In addition, the semi-transmissive and semi-reflective electrode has a visible light reflectivity of 20% to 80%, preferably 40% to 70%, and a resistivity of $1\times10^{-2}$ $\Omega$cm or lower.

In the light-emitting element, by changing the thicknesses of the transparent conductive film, the composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is emitted from the light-emitting layer and reflected back by the reflective electrode (first reflected light) considerably interferes with light that directly enters the semi-transmissive and semi-reflective electrode from the light-emitting layer (first incident light). For this reason, the optical path length between the reflective electrode and the light-emitting layer is preferably adjusted to $(2n-1)\lambda/4$ (n is a natural number of 1 or larger and $\lambda$ is a wavelength of a color to be amplified). In that case, the phases of the first reflected light and the first incident light can be aligned with each other and the light emitted from the light-emitting layer can be further amplified.

Note that in the above structure, the EL layer may be formed of a plurality of light-emitting layers or may be a single light-emitting layer. The tandem light-emitting element described above may be combined with the EL layer; for example, a light-emitting element may have a structure in which a plurality of EL layers is provided, a charge-generation layer is provided between the EL layers, and each EL layer is formed of a plurality of light-emitting layers or a single light-emitting layer.

<<Light-Emitting Device>>

Figure 6A:
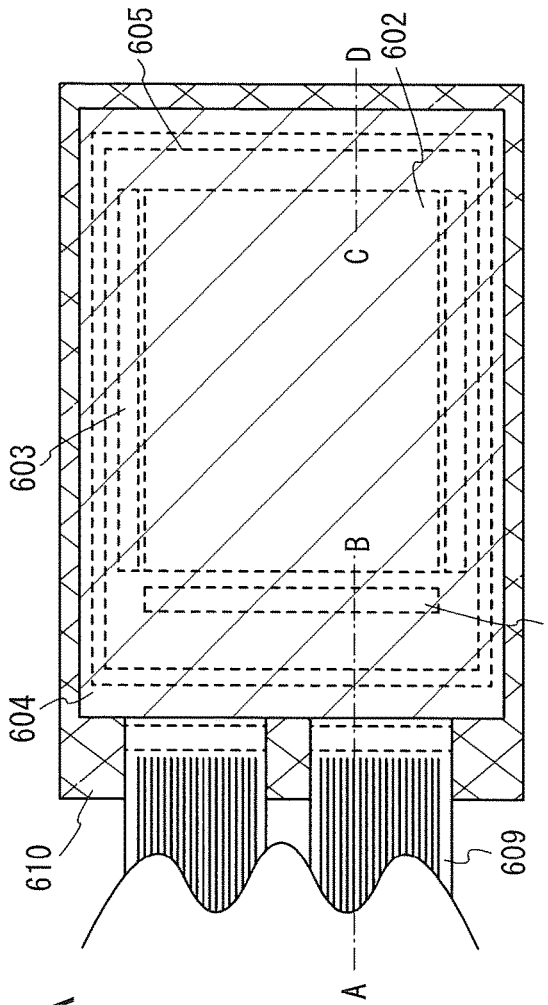
FIGS. 6A and 6B are conceptual diagrams of an active matrix light-emitting device.
Figure 6B:
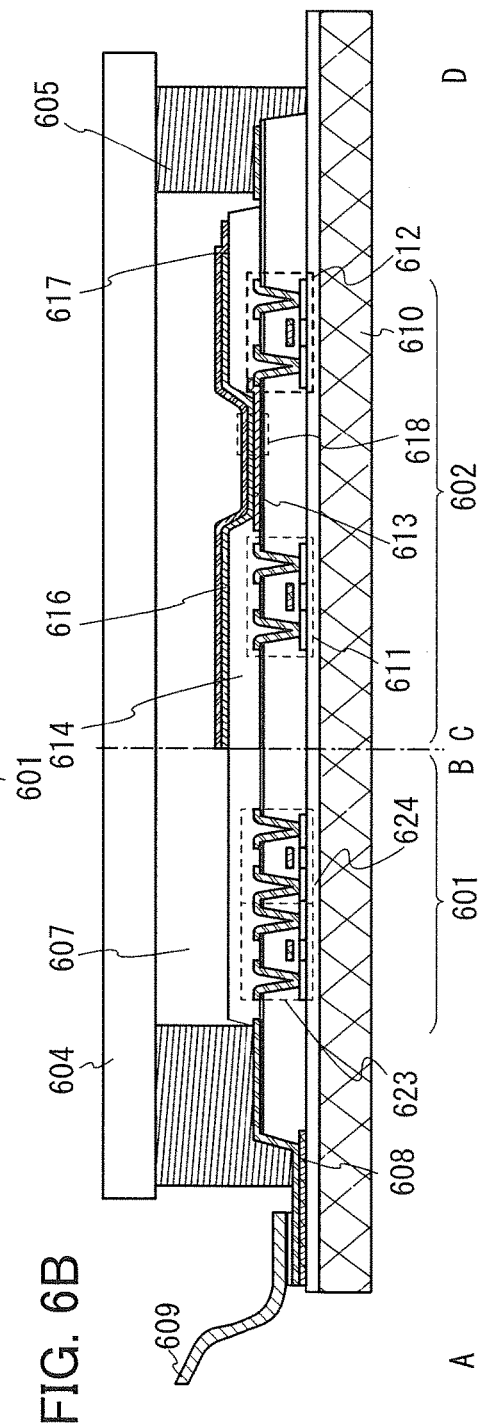

A light-emitting device of one embodiment of the present invention will be described with reference to FIGS. 6A and 6B. Note that FIG. 6A is a top view of the light-emitting device and FIG. 6B is a cross-sectional view taken along the lines A-B and C-D in FIG. 6A. The light-emitting device includes a driver circuit portion (source line driver circuit) 601, a pixel portion 602, and a driver circuit portion (gate line driver circuit) 603 which are illustrated with dotted lines. Furthermore, reference numeral 604 denotes a sealing substrate and reference numeral 605 denotes a sealant. A portion surrounded by the sealant 605 is a space 607.

Note that a lead wiring 608 is a wiring for transmitting signals to be input to the source line driver circuit 601 and the gate line driver circuit 603 and for receiving a video signal, a clock signal, a start signal, a reset signal, and the like from an FPC (flexible printed circuit) 609 functioning as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, a cross-sectional structure is described with reference to FIG. 6B. The driver circuit portion and the pixel portion are formed over an element substrate 610. Here, the source line driver circuit 601, which is the driver circuit portion, and one pixel of the pixel portion 602 are illustrated.

In the source line driver circuit 601, a CMOS circuit is formed in which an n-channel FET 623 and a p-channel FET 624 are combined. The driver circuit may be formed using various circuits such as a CMOS circuit, a PMOS circuit, or an NMOS circuit. Although a driver-integrated type where the driver circuit is formed over the substrate is described in this embodiment, a driver circuit is not necessarily formed over a substrate; a driver circuit may be formed outside a substrate.

The pixel portion 602 includes a plurality of pixels including a switching FET 611, a current controlling FET 612, and a first electrode 613 electrically connected to a drain of the current controlling FET 612. One embodiment of the present invention is not limited to this structure. The pixel portion may include three or more FETs and a capacitor in combination.

The kind and crystallinity of a semiconductor used for the FETs is not particularly limited; an amorphous semiconductor or a crystalline semiconductor may be used. Examples of the semiconductor used for the FETs include Group 13 semiconductor, Group 14 semiconductor, compound semiconductor, oxide semiconductor, and organic semiconductor materials. Oxide semiconductors are particularly preferable. Examples of the oxide semiconductor include an In—Ga oxide and an In-M-Zn oxide (M is Al, Ga, Y, Zr, La, Ce, or Nd). Note that an oxide semiconductor material that has an energy gap of 2 eV or more, preferably 2.5 eV or more, more preferably 3 eV or more is preferably used, in which case the off-state current of the transistors can be reduced.

Note that an insulator 614 is formed so as to cover an end portion of the first electrode 613. The insulator 614 can be formed using a positive photosensitive acrylic resin film here.

In order to improve the coverage, the insulator 614 is formed to have a curved surface with curvature at its upper or lower end portion. For example, in the case where a positive photosensitive acrylic resin is used for a material of the insulator 614, only the upper end portion of the insulator 614 preferably has a curved surface with a curvature radius (0.2 μm to 3 μm). Moreover, either a negative photosensitive resin or a positive photosensitive resin can be used for the insulator 614.

An EL layer 616 and a second electrode 617 are formed over the first electrode 613. The first electrode 613, the EL layer 616, and the second electrode 617 correspond, respectively, to the first electrode 101, the EL layer 103, and the second electrode 102 in FIG. 3A or 3B, and correspond, respectively, to the first electrode 501, the EL layer (511 to 513), and the second electrode 502 in FIG. 3C.

The EL layer 616 preferably contains an organometallic complex. The organometallic complex is preferably used as an emission center substance in the light-emitting layer.

The sealing substrate 604 is attached using the sealant 605 to the element substrate 610; thus, a light-emitting element 618 is provided in the space 607 surrounded by the element substrate 610, the sealing substrate 604, and the sealant 605. The space 607 is filled with filler, and may be filled with an inert gas (e.g., nitrogen or argon), the sealant 605, or the like. It is preferable that the sealing substrate be provided with a recessed portion and a drying agent be provided in the recessed portion, in which case deterioration due to influence of moisture can be suppressed.

An epoxy-based resin or glass frit is preferably used for the sealant 605. A material used for them is desirably a material which does not transmit moisture or oxygen as much as possible. As the element substrate 610 and the sealing substrate 604, for example, a glass substrate, a quartz substrate, or a plastic substrate formed of fiber reinforced plastic (FRP), polyvinyl fluoride (PVF), polyester, or acrylic can be used.

Note that in this specification and the like, a transistor or a light-emitting element can be formed using any of a variety of substrates, for example. The type of a substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used, for example. As an example of a glass substrate, a barium borosilicate glass substrate, an aluminoborosilicate glass substrate, a soda lime glass substrate, or the like can be given. Examples of the flexible substrate, the attachment film, the base material film, or the like are as follows: plastic typified by polyethylene terephthalate (PET), polyethylene naphthalate (PEN), and polyether sulfone (PES). Another example is a synthetic resin such as acrylic. Alternatively, polytetrafluoroethylene (PTFE), polypropylene, polyester, polyvinyl fluoride, polyvinyl chloride, or the like can be used. Alternatively, polyamide, polyimide, aramid, epoxy, an inorganic film formed by evaporation, paper, or the like can be used. Specifically, the use of semiconductor substrates, single crystal substrates, SOI substrates, or the like enables the manufacture of small-sized transistors with a small variation in characteristics, size, shape, or the like and with high current capability. A circuit using such transistors achieves lower power consumption of the circuit or higher integration of the circuit.

Alternatively, a flexible substrate may be used as the substrate, and the transistor or the light-emitting element may be provided directly over the flexible substrate. Still alternatively, a separation layer may be provided between a substrate and the transistor or between the substrate and the light-emitting element. The separation layer can be used when part or the whole of a semiconductor device formed over the separation layer is separated from the substrate and transferred onto another substrate. In such a case, the transistor can be transferred to a substrate having low heat resistance or a flexible substrate as well. For the above separation layer, a stack including inorganic films, which are a tungsten film and a silicon oxide film, or an organic resin film of polyimide or the like formed over a substrate can be used, for example.

In other words, a transistor or a light-emitting element may be formed using one substrate, and then transferred to another substrate. Examples of the substrate to which the transistor or the light-emitting element is transferred include, in addition to the above-described substrates over which transistors can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. When such a substrate is used, a transistor with excellent properties or a transistor with low power consumption can be formed, a device with high durability and high heat resistance can be provided, or a reduction in weight or thickness can be achieved.

FIGS. 7A and 7B each illustrate an example of a light-emitting device in which full color display is achieved by forming a light-emitting element exhibiting white light emission and using coloring layers (color filters) and the like. In FIG. 7A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, an EL layer 1028, a second electrode 1029 of the light-emitting elements, a sealing substrate 1031, a sealant 1032, and the like are illustrated.

In FIG. 7A, coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is positioned and fixed to the substrate 1001. Note that the coloring layers and the black layer are covered with an overcoat layer.

In FIG. 7A, light emitted from some of the light-emitting layers does not pass through the coloring layers, while light emitted from the others of the light-emitting layers passes through the coloring layers. Since light which does not pass through the coloring layers is white and light which passes through any one of the coloring layers is red, blue, or green, an image can be displayed using pixels of the four colors.

FIG. 7B illustrates an example in which the coloring layers (the red coloring layer 1034R, the green coloring layer 1034G, and the blue coloring layer 1034B) are formed between the gate insulating film 1003 and the first interlayer insulating film 1020. As in this structure, the coloring layers may be provided between the substrate 1001 and the sealing substrate 1031.

Figure 8:
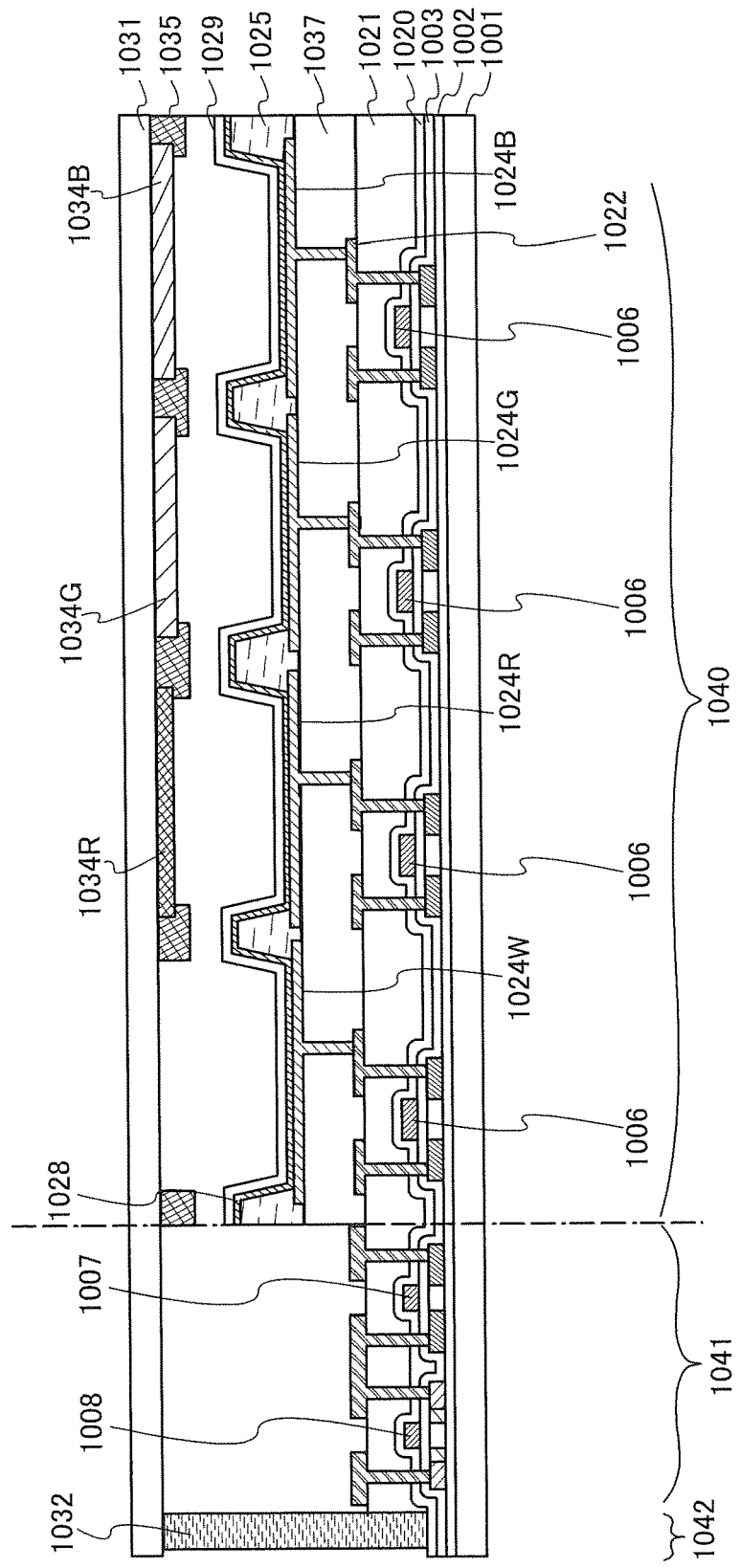
FIG. 8 is a conceptual diagram of an active matrix light-emitting device.

The above-described light-emitting device has a structure in which light is extracted from the substrate 1001 side where the FETs are formed (a bottom emission structure), but may have a structure in which light is extracted from the sealing substrate 1031 side (a top emission structure). FIG. 8 is a cross-sectional view of a light-emitting device having a top emission structure. In that case, a substrate which does not transmit light can be used as the substrate 1001. The process up to the step of forming of a connection electrode which connects the FET and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, or can be formed using any other various materials.

The first electrodes 1024W, 1024R, 1024G, and 1024B of the light-emitting elements each function as an anode here, but may function as a cathode. Furthermore, in the case of the light-emitting device having a top emission structure as illustrated in FIG. 8, the first electrodes are preferably reflective electrodes. The EL layer 1028 is formed to have a structure similar to the structure of the EL layer 103 in FIG. 3A or 3B or the EL layer (511 to 513) in FIG. 3C, with which white light emission can be obtained.

In the case of a top emission structure as illustrated in FIG. 8, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (the black matrix) 1035 which is positioned between pixels. The coloring layers (the red coloring layer 1034R, the green coloring layer 1034G, and the blue coloring layer 1034B) and the black layer may be covered with the overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue or four colors of red, green, blue, and yellow may be performed.

Figure 9A:
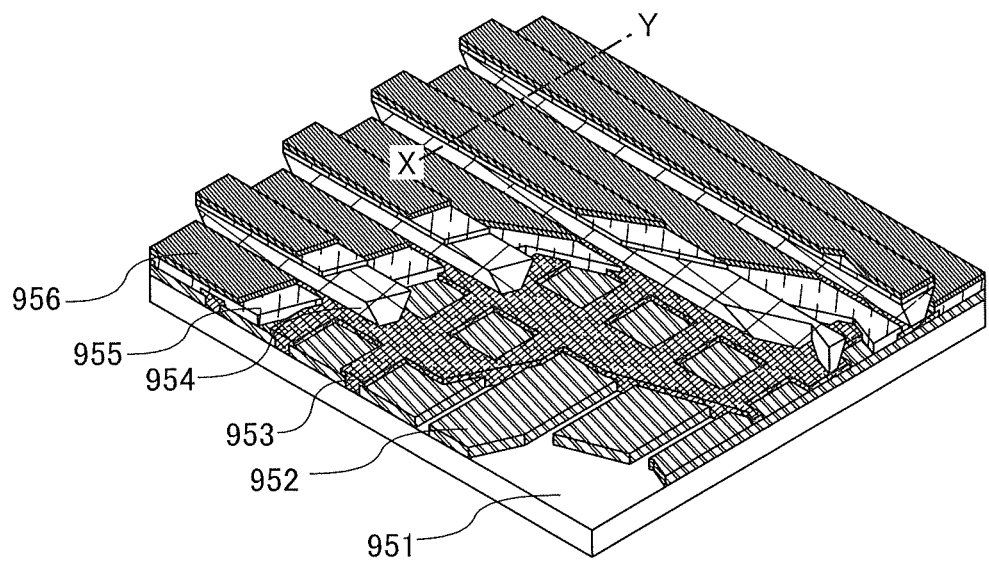
FIGS. 9A and 9B are conceptual diagrams of a passive matrix light-emitting device.
Figure 9B:
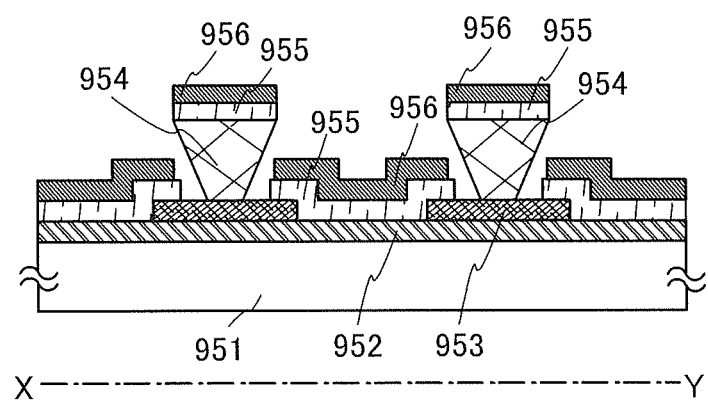

FIGS. 9A and 9B illustrate a passive matrix light-emitting device of one embodiment of the present invention. FIG. 9A is a perspective view of a light-emitting device, and FIG. 9B is a cross-sectional view taken along the line X-Y of FIG. 9A. In FIGS. 9A and 9B, an EL layer 955 is provided between an electrode 952 and an electrode 956 over a substrate 951. An end portion of the electrode 952 is covered with an insulating layer 953. A partition layer 954 is provided over the insulating layer 953. Sidewalls of the partition layer 954 are aslope such that the distance between the sidewalls is gradually narrowed toward the surface of the substrate. That is, a cross section in a short side direction of the partition layer 954 is a trapezoidal shape, and a lower side (the side facing the same direction as the plane direction of the insulating layer 953 and touching the insulating layer 953) is shorter than an upper side (the side facing the same direction as the plane direction of the insulating layer 953, and not touching the insulating layer 953). By providing the partition layer 954 in this manner, defects of the light-emitting element due to static charge and the like can be prevented.

Since many minute light-emitting elements arranged in a matrix can be controlled with the FETs formed in the pixel portion, the above-described light-emitting device can be suitably used as a display device for displaying images.

<<Lighting Device>>

Figure 10A:
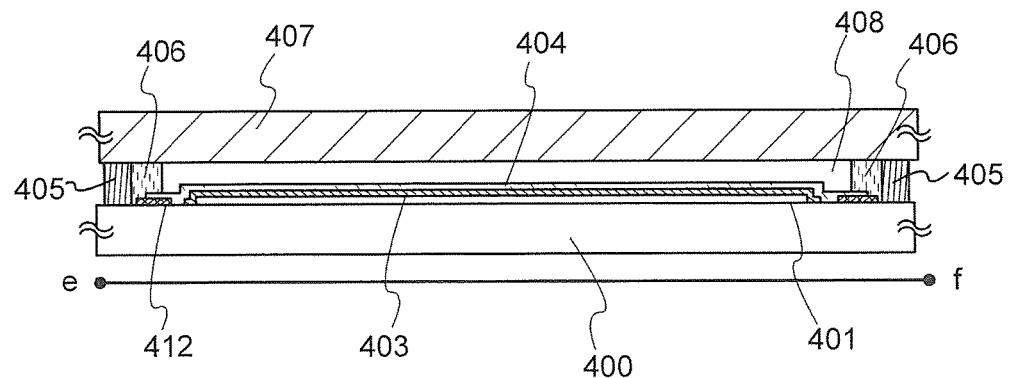
FIGS. 10A and 10B illustrate a lighting device.
Figure 10B:
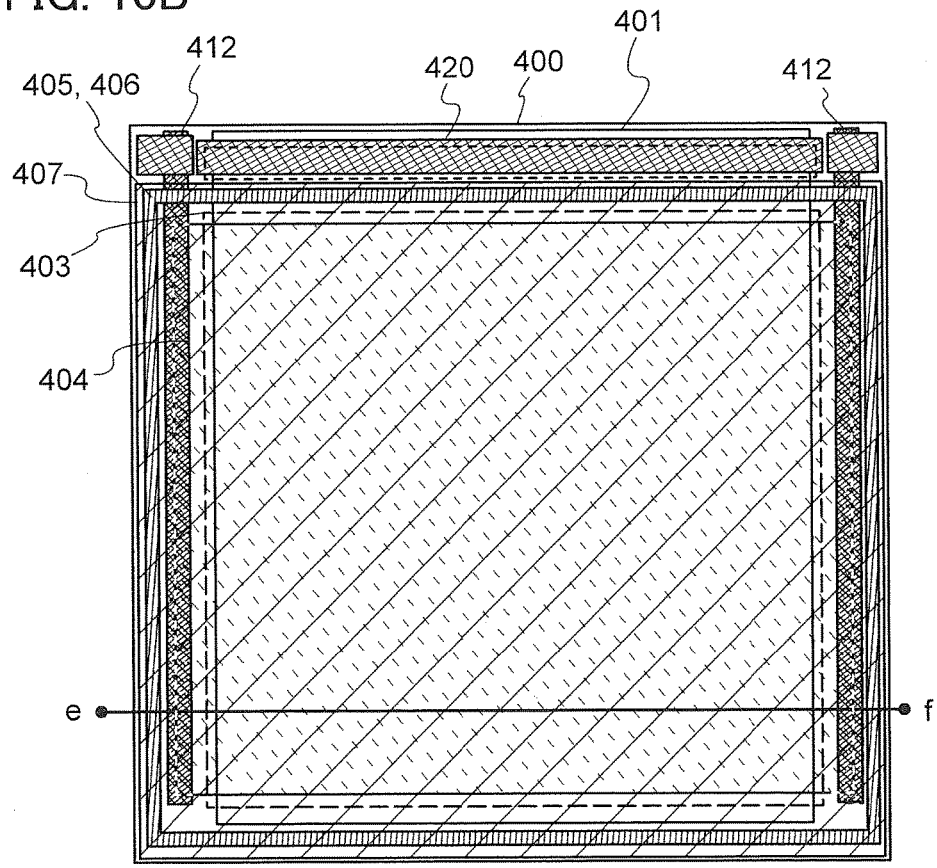

A lighting device of one embodiment of the present invention is described with reference to FIGS. 10A and 10B. FIG. 10B is a top view of the lighting device, and FIG. 10A is a cross-sectional view taken along the line e-f in FIG. 10B.

In the lighting device, a first electrode 401 is formed over a substrate 400 which is a support and has a light-transmitting property. The first electrode 401 corresponds to the first electrode 101 in FIGS. 3A and 3B. When light is extracted through the first electrode 401 side, the first electrode 401 is formed using a material having a light-transmitting property.

A pad 412 for applying voltage to a second electrode 404 is provided over the substrate 400.

An EL layer 403 is formed over the first electrode 401. The EL layer 403 corresponds to, for example, the EL layer 103 in FIGS. 3A and 3B or the EL layer (511 to 513) in FIG. 3C. For these structures, the corresponding description can be referred to.

The second electrode 404 is formed to cover the EL layer 403. The second electrode 404 corresponds to the second electrode 102 in FIG. 3A or 3B. The second electrode 404 contains a material having high reflectivity when light is extracted through the first electrode 401 side. The second electrode 404 is connected to the pad 412, whereby voltage is applied thereto.

A light-emitting element is formed with the first electrode 401, the EL layer 403, and the second electrode 404. The light-emitting element is fixed to a sealing substrate 407 with sealants 405 and 406 and sealing is performed, whereby the lighting device is completed. It is possible to use only either the sealant 405 or the sealant 406. In addition, the inner sealant 406 (not illustrated in FIG. 10B) can be mixed with a desiccant that enables moisture to be adsorbed, which results in improved reliability.

When part of the pad 412 and part of the first electrode 401 are extended to the outside of the sealants 405 and 406, the extended parts can function as external input terminals. An IC chip 420 mounted with a converter or the like may be provided over the external input terminals.

<<Electronic Device>>

Examples of an electronic device of one embodiment of the present invention are described. Examples of the electronic device include a television device (also referred to as a television or a television receiver), a monitor of a computer or the like, a camera such as a digital camera or a digital video camera, a digital photo frame, a mobile phone (also referred to as a mobile telephone or a mobile phone device), a portable game console, a portable information terminal, an audio reproducing device, and a large-sized game machine such as a pachinko machine. Specific examples of these electronic devices are described below.

FIG. 11A illustrates an example of a television device. In the television device, a display portion 7103 is incorporated in a housing 7101. In addition, here, the housing 7101 is supported by a stand 7105. Images can be displayed on the display portion 7103, and in the display portion 7103, light-emitting elements are arranged in a matrix.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, a general television broadcast can be received. Moreover, when the television device is connected to a communication network with or without wires via the modem, one-way (from a sender to a receiver) or two-way (between a sender and a receiver or between receivers) data communication can be performed.

FIG. 11B1 illustrates a computer, which includes a main body 7201, a housing 7202, a display portion 7203, a keyboard 7204, an external connection port 7205, a pointing device 7206, and the like. Note that this computer is manufactured by using light-emitting elements arranged in a matrix in the display portion 7203. The computer illustrated in FIG. 11B1 may have a structure illustrated in FIG. 11B2. The computer illustrated in FIG. 11B2 is provided with a second display portion 7210 instead of the keyboard 7204 and the pointing device 7206. The second display portion 7210 is a touch panel, and input can be performed by operation of display for input on the second display portion 7210 with a finger or a dedicated pen. The second display portion 7210 can also display images other than the display for input. The display portion 7203 may also be a touch panel. Connecting the two screens with a hinge can prevent troubles; for example, the screens can be prevented from being cracked or broken while the computer is being stored or carried.

FIGS. 11C and 11D illustrate an example of a portable information terminal. The portable information terminal is provided with a display portion 7402 incorporated in a housing 7401, operation buttons 7403, an external connection port 7404, a speaker 7405, a microphone 7406, and the like. Note that the portable information terminal has the display portion 7402 including light-emitting elements arranged in a matrix.

Information can be input to the portable information terminal illustrated in FIGS. 11C and 11D by touching the display portion 7402 with a finger or the like. In that case, operations such as making a call and creating e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or creating e-mail, a text input mode mainly for inputting text is selected for the display portion 7402 so that text displayed on a screen can be input. In that case, it is preferable to display a keyboard or number buttons on almost the entire screen of the display portion 7402.

When a detection device including a sensor such as a gyroscope sensor or an acceleration sensor for sensing inclination is provided inside the portable information terminal, screen display of the display portion 7402 can be automatically changed by determining the orientation of the mobile phone (whether the mobile phone is placed horizontally or vertically).

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal sensed by an optical sensor in the display portion 7402 is sensed, the screen mode may be controlled so as to be switched from the input mode to the display mode.

The display portion 7402 may also function as an image sensor. For example, an image of a palm print, a fingerprint, or the like is taken by touch on the display portion 7402 with the palm or the finger, whereby personal authentication can be performed. Furthermore, by providing a backlight or a sensing light source which emits near-infrared light in the display portion, an image of a finger vein, a palm vein, or the like can be taken.

Note that in the above electronic devices, any of the structures described in this specification can be combined as appropriate.

The display portion preferably includes a light-emitting element of one embodiment of the present invention. The light-emitting element can have high emission efficiency. In addition, the light-emitting element can be driven with low drive voltage. Thus, the electronic device including the light-emitting element of one embodiment of the present invention can have low power consumption.

Figure 12:
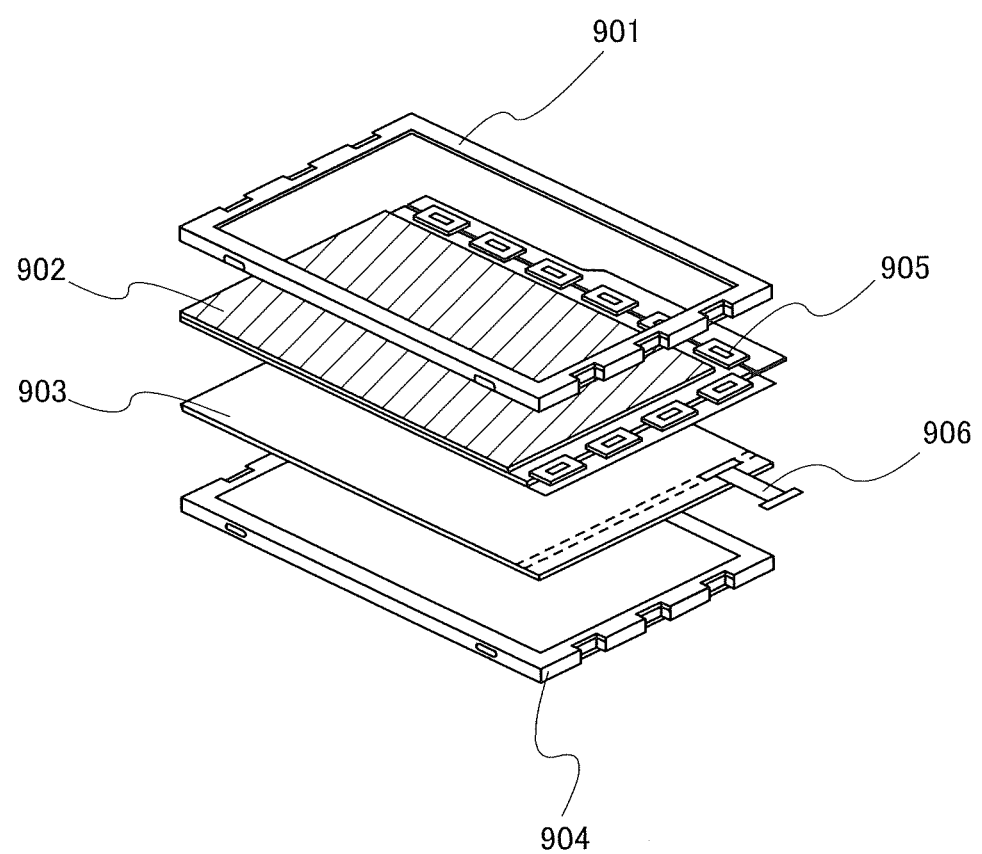
FIG. 12 illustrates a light source device.

FIG. 12 illustrates an example of a liquid crystal display device including the light-emitting element for a backlight. The liquid crystal display device illustrated in FIG. 12 includes a housing 901, a liquid crystal layer 902, a backlight unit 903, and a housing 904. The liquid crystal layer 902 is connected to a driver IC 905. The light-emitting element is used for the backlight unit 903, to which current is supplied through a terminal 906.

As the light-emitting element, a light-emitting element of one embodiment of the present invention is preferably used. By including the light-emitting element, the backlight of the liquid crystal display device can have low power consumption.

Figure 13:
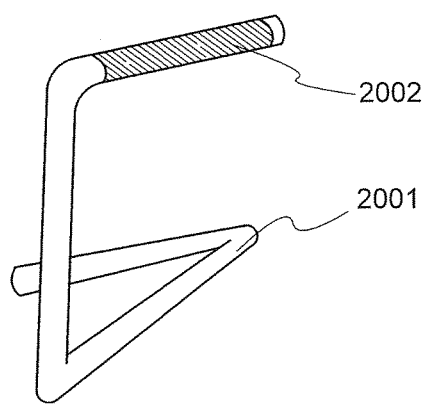
FIG. 13 illustrates a lighting device.

FIG. 13 illustrates an example of a desk lamp of one embodiment of the present invention. The desk lamp illustrated in FIG. 13 includes a housing 2001 and a light source 2002, and a lighting device including a light-emitting element is used as the light source 2002.

Figure 14:
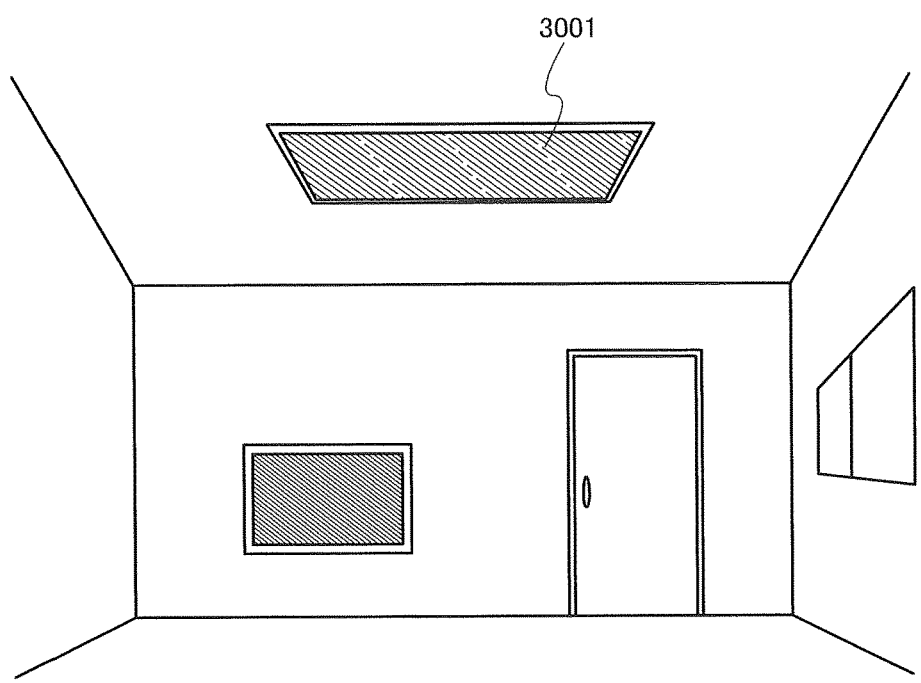
FIG. 14 illustrates a lighting device.

FIG. 14 illustrates an example of an indoor lighting device 3001. The light-emitting element of one embodiment of the present invention is preferably used in the lighting device 3001.

Figure 15:
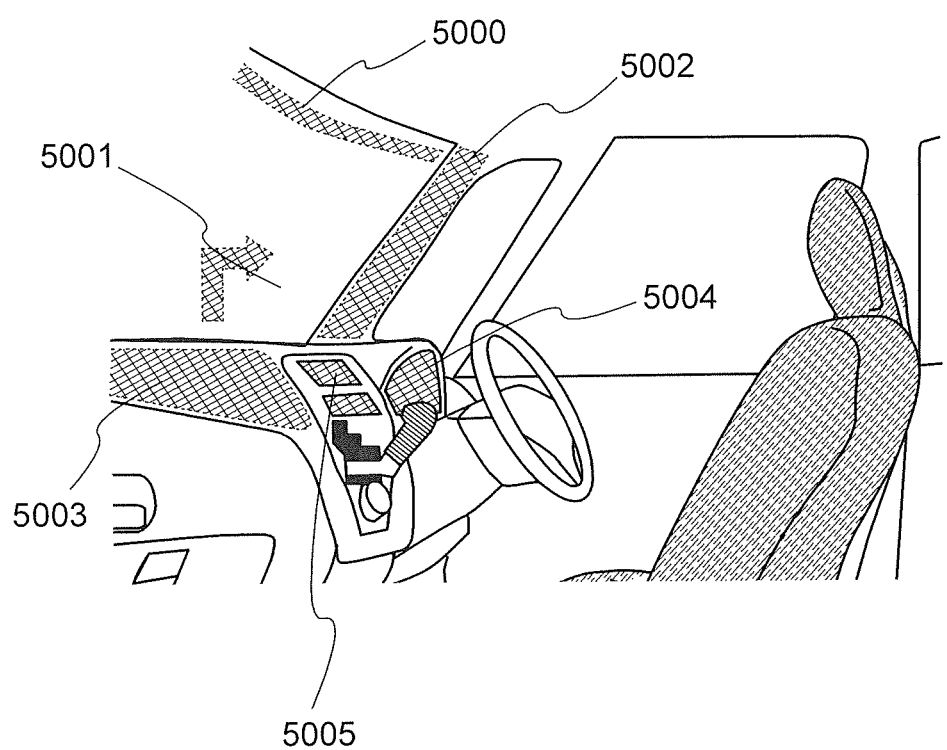
FIG. 15 illustrates car-mounted display devices and lighting devices.

An automobile of one embodiment of the present invention is illustrated in FIG. 15. In the automobile, light-emitting elements are used for a windshield and a dashboard. Display regions 5000 to 5005 are preferably formed by using the light-emitting elements of one embodiment of the present invention. This suppresses power consumption of the display regions 5000 to 5005, showing suitability for use in an automobile.

The display regions 5000 and 5001 are display devices which are provided in the automobile windshield and which include the light-emitting elements. When a first electrode and a second electrode are formed of electrodes having light-transmitting properties in these light-emitting elements, what is called a see-through display device, through which the opposite side can be seen, can be obtained. Such see-through display devices can be provided even in the windshield of the automobile, without hindering the vision. Note that in the case where a transistor for driving the light-emitting element is provided, a transistor having a light-transmitting property, such as an organic transistor using an organic semiconductor material or a transistor using an oxide semiconductor, is preferably used.

The display region 5002 is a display device which is provided in a pillar portion and which includes the light-emitting element. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation information, a speedometer, a tachometer, a mileage, a fuel meter, a gearshift indicator, and air-condition setting. The content or layout of the display can be changed freely by a user as appropriate. Note that such information can also be shown by the display regions 5000 to 5003. The display regions 5000 to 5005 can also be used as lighting devices.

Figure 16A:
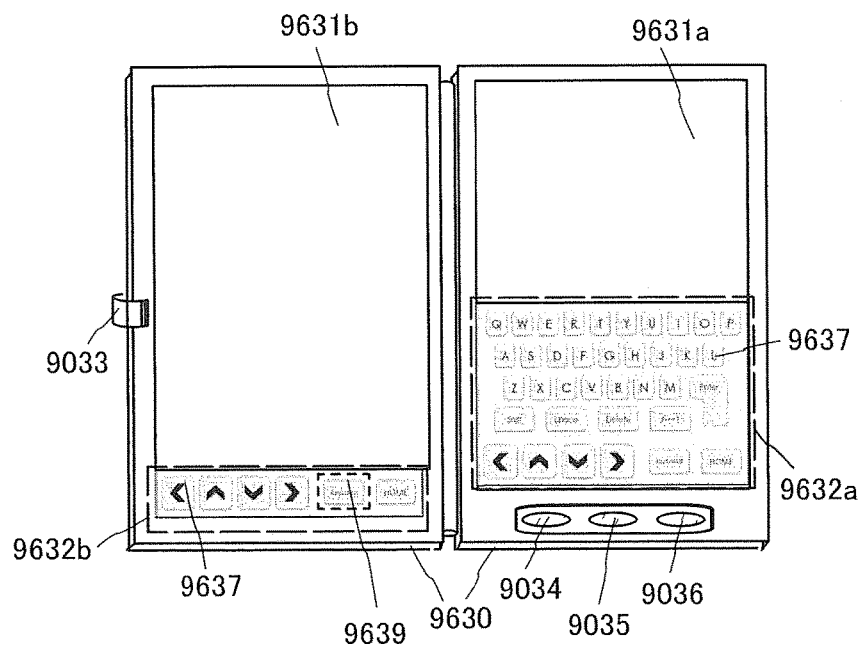
FIGS. 16A to 16C illustrate an electronic device.
Figure 16B:
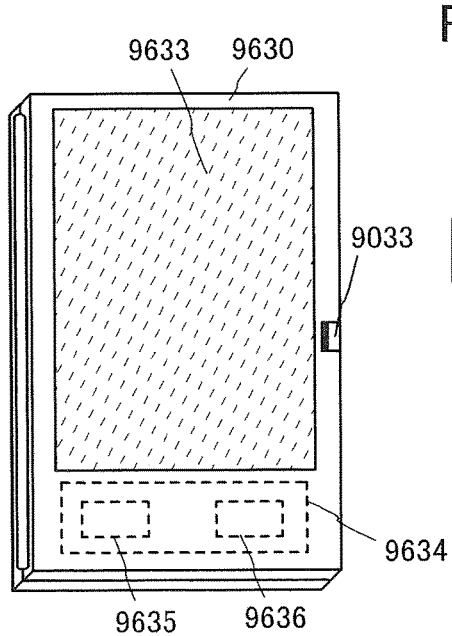

FIGS. 16A and 16B illustrate an example of a foldable tablet terminal. In FIG. 16A, the tablet terminal is opened, and includes a housing 9630, a display portion 9631a, a display portion 9631b, a switch 9034 for switching display modes, a power switch 9035, a switch 9036 for switching to power-saving mode, a fastener 9033, and an operation switch 9038. Note that in the tablet terminal, one or both of the display portion 9631a and the display portion 9631b are formed using a light-emitting device which includes the light-emitting element of one embodiment of the present invention.

Part of the display portion 9631a can be a touch panel region 9632a and data can be input when a displayed operation key 9637 is touched. Although a structure in which a half region in the display portion 9631a has only a display function and the other half region has a touch panel function is illustrated as an example, the structure of the display portion 9631a is not limited thereto. The whole region in the display portion 9631a may have a touch panel function. For example, the display portion 9631a can display keyboard buttons in the whole region to be a touch panel, and the display portion 9631b can be used as a display screen.

Like the display portion 9631a, part of the display portion 9631b can be a touch panel region 9632b. When a switching button 9639 for showing/hiding a keyboard on the touch panel is touched with a finger, a stylus, or the like, the keyboard can be displayed on the display portion 9631b.

Touch input can be performed in the touch panel region 9632a and the touch panel region 9632b at the same time.

The switch 9034 for switching display modes can switch the display between portrait mode, landscape mode, and the like, and between monochrome display and color display, for example. The switch 9036 for switching to power-saving mode can control display luminance to be optimal in accordance with the amount of external light in use of the tablet terminal which is sensed by an optical sensor incorporated in the tablet terminal. Another sensing device including a sensor for sensing inclination, such as a gyroscope sensor or an acceleration sensor, may be incorporated in the tablet terminal, in addition to the optical sensor.

Note that FIG. 16A illustrates an example in which the display portion 9631a and the display portion 9631b have the same display area; however, without limitation thereon, one of the display portions may be different from the other display portion in size and display quality. For example, one display panel may be capable of higher-definition display than the other display panel.

FIG. 16B illustrates the tablet terminal which is folded. The tablet terminal in this embodiment includes the housing 9630, a solar cell 9633, a charge and discharge control circuit 9634, a battery 9635, and a DCDC converter 9636. Note that in FIG. 16B, an example in which the charge and discharge control circuit 9634 includes the battery 9635 and the DCDC converter 9636 is illustrated.

Since the tablet terminal can be folded, the housing 9630 can be closed when the tablet terminal is not used. As a result, the display portion 9631a and the display portion 9631b can be protected; thus, a tablet terminal which has excellent durability and excellent reliability in terms of long-term use can be provided.

In addition, the tablet terminal illustrated in FIGS. 16A and 16B can have a function of displaying a variety of kinds of data (e.g., a still image, a moving image, and a text image), a function of displaying a calendar, a date, the time, or the like on the display portion, a touch-input function of operating or editing the data displayed on the display portion by touch input, a function of controlling processing by a variety of kinds of software (programs), and the like.

The solar cell 9633 provided on a surface of the tablet terminal can supply power to the touch panel, the display portion, a video signal processing portion, or the like. Note that the solar cell 9633 is preferably provided on one or two surfaces of the housing 9630, in which case the battery 9635 can be charged efficiently.

Figure 16C:
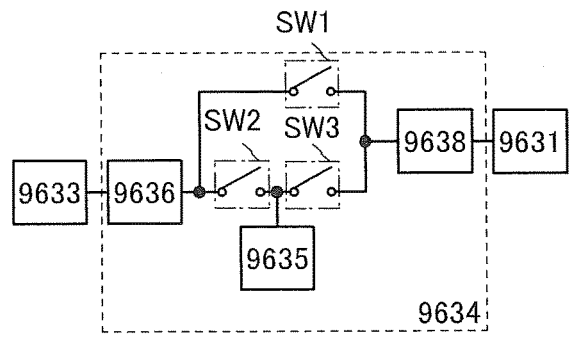

The structure and the operation of the charge and discharge control circuit 9634 illustrated in FIG. 16B are described with reference to a block diagram in FIG. 16C. FIG. 16C illustrates the solar cell 9633, the battery 9635, the DCDC converter 9636, a converter 9638, switches SW1 to SW3, and the display portion 9631. The battery 9635, the DCDC converter 9636, the converter 9638, and the switches SW1 to SW3 correspond to the charge and discharge control circuit 9634 illustrated in FIG. 16B.

First, an example of the operation in the case where power is generated by the solar cell 9633 using external light is described. The voltage of power generated by the solar cell is raised or lowered by the DCDC converter 9636 so that the power has a voltage for charging the battery 9635. Then, when power supplied from the battery 9635 charged by the solar cell 9633 is used for the operation of the display portion 9631, the switch SW1 is turned on and the voltage of the power is raised or lowered by the converter 9638 so as to be voltage needed for the display portion 9631. In addition, when display on the display portion 9631 is not performed, the switch SW1 is turned off and the switch SW2 is turned on so that charge of the battery 9635 may be performed.

Although the solar cell 9633 is described as an example of a power generation means, the power generation means is not particularly limited, and the battery 9635 may be charged by another power generation means such as a piezoelectric element or a thermoelectric conversion element (Peltier element). The battery 9635 may be charged by a non-contact power transmission module capable of performing charging by transmitting and receiving power wirelessly (without contact), or any of the other charge means used in combination, and the power generation means is not necessarily provided.

One embodiment of the present invention is not limited to the tablet terminal having the shape illustrated in FIGS. 16A to 16C as long as the display portion 9631 is included.

Figure 17A:
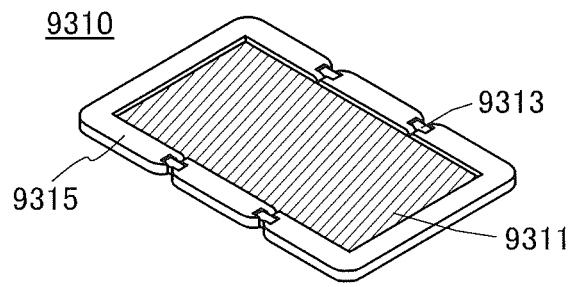
FIGS. 17A to 17C illustrate an electronic device.
Figure 17B:
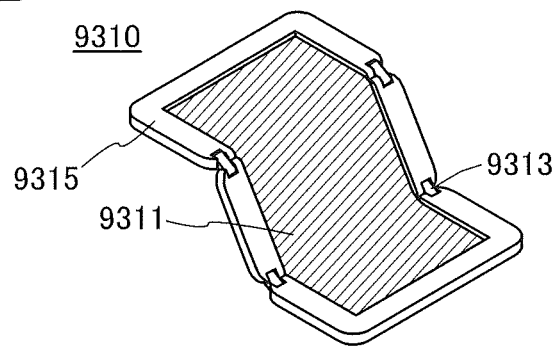
Figure 17C:
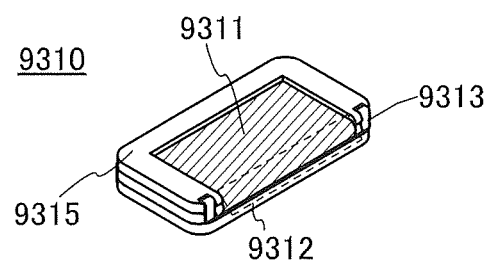

FIGS. 17A to 17C illustrate a foldable portable information terminal 9310. FIG. 17A illustrates the portable information terminal 9310 which is opened. FIG. 17B illustrates the portable information terminal 9310 which is being opened or being folded. FIG. 17C illustrates the portable information terminal 9310 which is folded. The portable information terminal 9310 is highly portable when folded. The portable information terminal 9310 is highly browsable when opened because of a seamless large display region.

A display panel 9311 is supported by three housings 9315 joined together by hinges 9313. Note that the display panel 9311 may be a touch panel (an input/output device) including a touch sensor (an input device). By bending the display panel 9311 at a connection portion between two housings 9315 with the use of the hinges 9313, the portable information terminal 9310 can be reversibly changed in shape from an opened state to a folded state. A light-emitting device of one embodiment of the present invention can be used for the display panel 9311. A display region 9312 in the display panel 9311 is a display region that is positioned at a side surface of the portable information terminal 9310 that is folded. On the display region 9312, information icons, file shortcuts of frequently used applications or programs, and the like can be displayed, and confirmation of information and start of application can be smoothly performed.

Example 1

Figure 18:
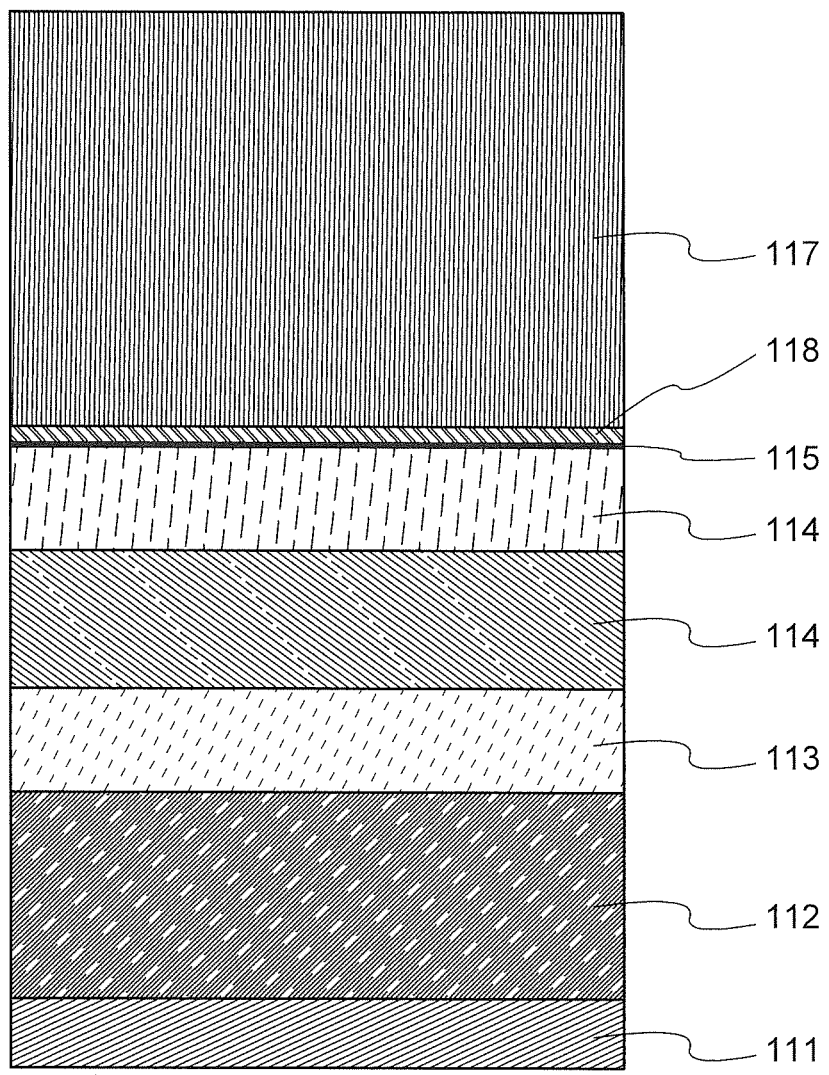
FIG. 18 is a conceptual diagram of a light-emitting element for measurement.

In this example, results of calculating the parameter a of a light-emitting element (Light-emitting Element 1) of one embodiment of the present invention with high efficiency are described in detail. For the above purpose, a light-emitting element (Light-emitting Element 1-1) for measurement which includes a light-emitting layer having the same structure as that of Light-emitting Element 1 and in which the luminance in the front direction is reduced as much as possible was also fabricated. FIG. 18 illustrates the structure of the light-emitting element.

First, a fabrication method and the structure of the light-emitting element of one embodiment of the present invention are described. Organic compounds used in the light-emitting element of one embodiment of the present invention are given below.

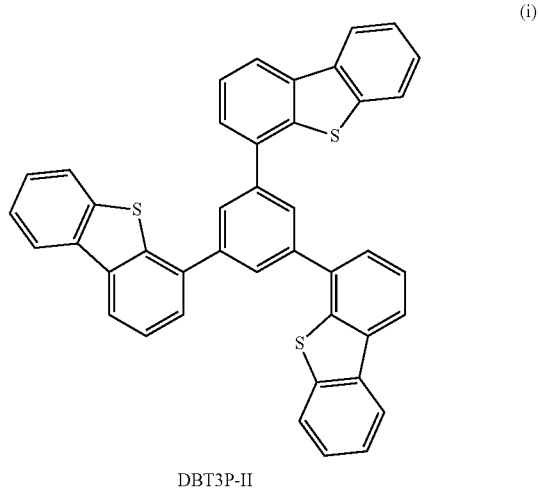

DBT3P-II

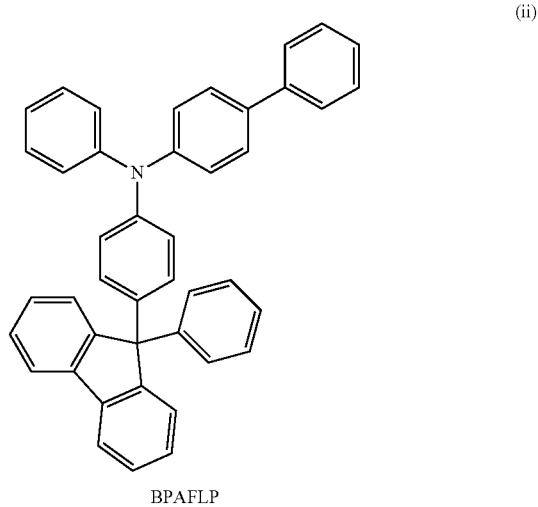

BPAFLP

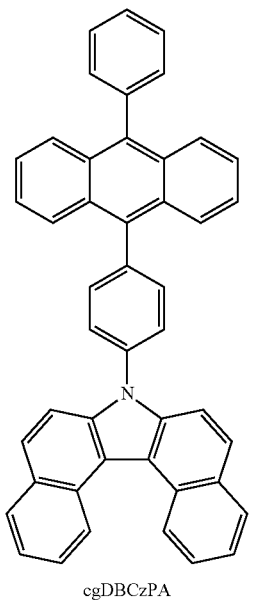

cgDBCzPA

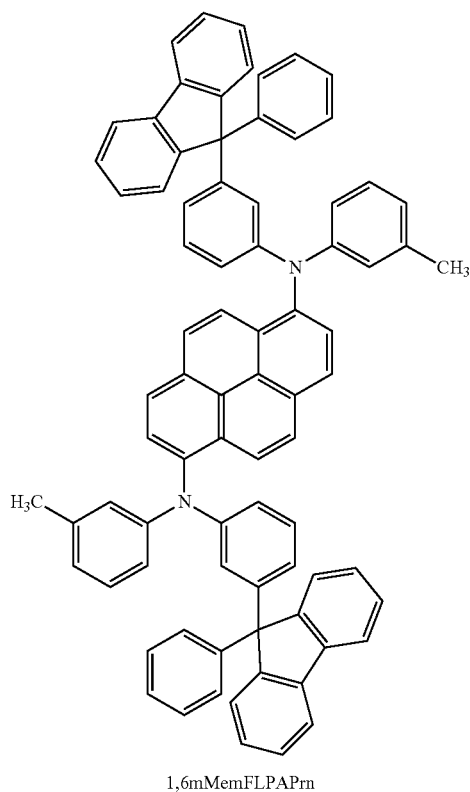

1,6mMemFLPAPrn

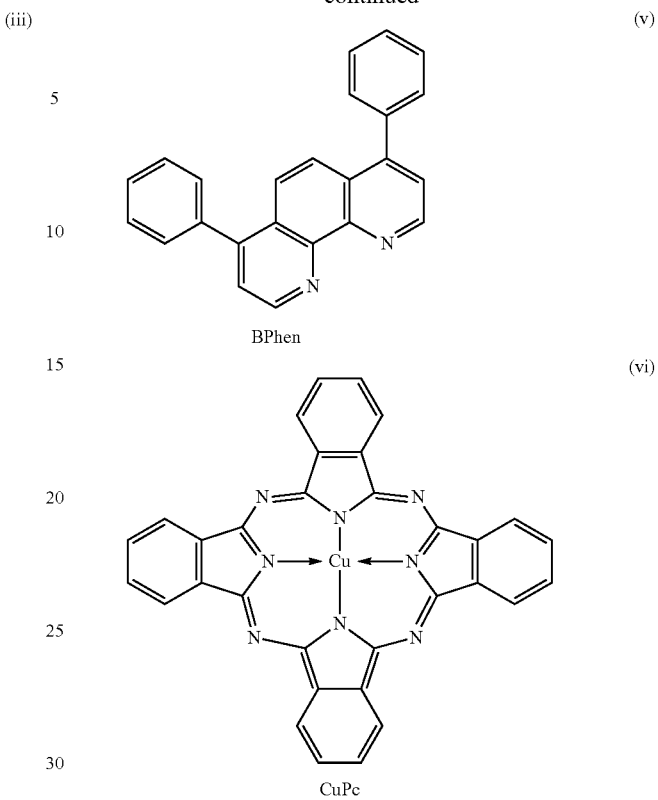

BPhen

CuPc (Fabrication Method of Light-Emitting Element 1)

First, a film of indium tin oxide containing silicon oxide (ITSO) was formed over a glass substrate by a sputtering method, so that the first electrode 101 was formed. The thickness of the first electrode 101 was 70 nm and the electrode area was 2 mm×2 mm.

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 4,4',4''-(benzene-1,3,5-triyl) tri(dibenzothiophene) (abbreviation: DBT3P-II) represented by Structural Formula (i) and molybdenum(VI) oxide were deposited by co-evaporation to a thickness of 10 nm at a weight ratio of 4:2 (=DBT3P-II: molybdenum oxide) by an evaporation method using resistance heating, so that the hole-injection layer 111 was formed.

Next, a film of 4-phenyl-4'-(9-phenylfluoren-9-yl)triphenylamine (abbreviation: BPAFLP) represented by Structural Formula (ii) was formed by evaporation to a thickness of 30 nm on the hole-injection layer 111 to form the hole-transport layer 112.

After that, the light-emitting layer 113 was formed by co-evaporation of 7-[4-(10-phenyl-9-anthryl)phenyl]-7H- dibenzo[c,g]carbazole (abbreviation: cgDBCzPA) represented by Structural Formula (iii) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by Structural Formula (iv) at a weight ratio of 1:0.03 (=cgDBCzPA: 1,6mMemFLPAPrn) to a thickness of 15 nm. In the step of forming the light-emitting layer 113 (at the time of evaporation), the total pressure was approximately $1 \times 10^{-4}$ Pa and the partial pressure of carbon dioxide whose molecular weight was detected as 44 was approximately $6 \times 10^{-7}$ Pa when the measurement was performed by Q-mass provided in an evaporation chamber. That is, the percentage of the partial pressure of carbon dioxide with respect to the total pressure at the time of evaporation was approximately 0.6%. In this manner, it is important that the percentage of the partial pressure of carbon dioxide with respect to the total pressure at the time of evaporation is higher than 0.03%, specifically, higher than or equal to 0.1%. Since only gases whose molecular weight is 1 to 200 can be detected by Q-mass, the total pressure measured by Q-mass is, strictly speaking, different from a practical total pressure in the chamber. However, the partial pressure of gas components whose molecular weight exceeds 200 is negligible; thus, with the use of either the total pressure measured by Q-mass or the practical total pressure in the chamber, similar results can be obtained.

Then, on the light-emitting layer 113, cgDBCzPA was deposited by evaporation to a thickness of 20 nm, and bathophenanthroline (abbreviation: BPhen) represented by Structural Formula (v) was deposited by evaporation to a thickness of 15 nm to form the electron-transport layer 114.

After the formation of the electron-transport layer 114, lithium oxide ($Li_2O$) was deposited by evaporation to a thickness of 0.1 nm to form the electron-injection layer 115. Then, aluminum was deposited by evaporation to a thickness of 200 nm to form the second electrode 102. Through the above-described steps, Light-emitting Element 1 of this example was fabricated.

(Fabrication Method of Light-Emitting Element 1-1)

Light-emitting Element 1-1 was fabricated in the following manner. After the electron-injection layer 115 of Light-emitting Element 1 was formed, copper phthalocyanine (abbreviation: CuPc) represented by Structural Formula (vi) was deposited by evaporation to a thickness of 2 nm to form the electron-relay layer 118, and then, DBT3P-II and molybdenum(VI) oxide were deposited by co-evaporation at a weight ratio of 2:1 (=DBT3P-II: molybdenum oxide) to a thickness of 60 nm to form the p-type layer 117. In such a manner, a layer for adjusting the thickness was formed.

The element structures of Light-emitting Elements 1 and 1-1 are shown in the following table.

TABLE 1

| | hole-injection layer | hole-transport layer | light-emitting layer | electron-transport layer | electron-injection layer | layer for adjusting the thickness | |
|---|---|---|---|---|---|---|---|
| | 10 nm | 30 nm | 15 nm | 20 nm | 15 nm | 0.1 nm | 2 nm | 60 nm |
| Element 1 | DBT3P-II:MoOx (4:2) | BPAFLP | cgDBCzPA: 1,6mMemFLPAPrn (1:0.03) | cgDBCzPA | BPhen | $Li_2O$ | — | — |
| Element 1-1 | | | | | | | CuPc | DBT3P-II:MoOx (4:2) |

Light-emitting Elements 1 and 1-1 were each sealed using a glass substrate in a glove box containing a nitrogen atmosphere so as not to be exposed to the air (specifically, a sealant was applied to surround the element and UV treatment and heat treatment at 80° C. for 1 hour were performed at the time of sealing). Then, the initial characteristics of Light-emitting Elements 1 and 1-1 were measured. Note that the measurement was carried out in an atmosphere kept at 25° C.

Figure 19:
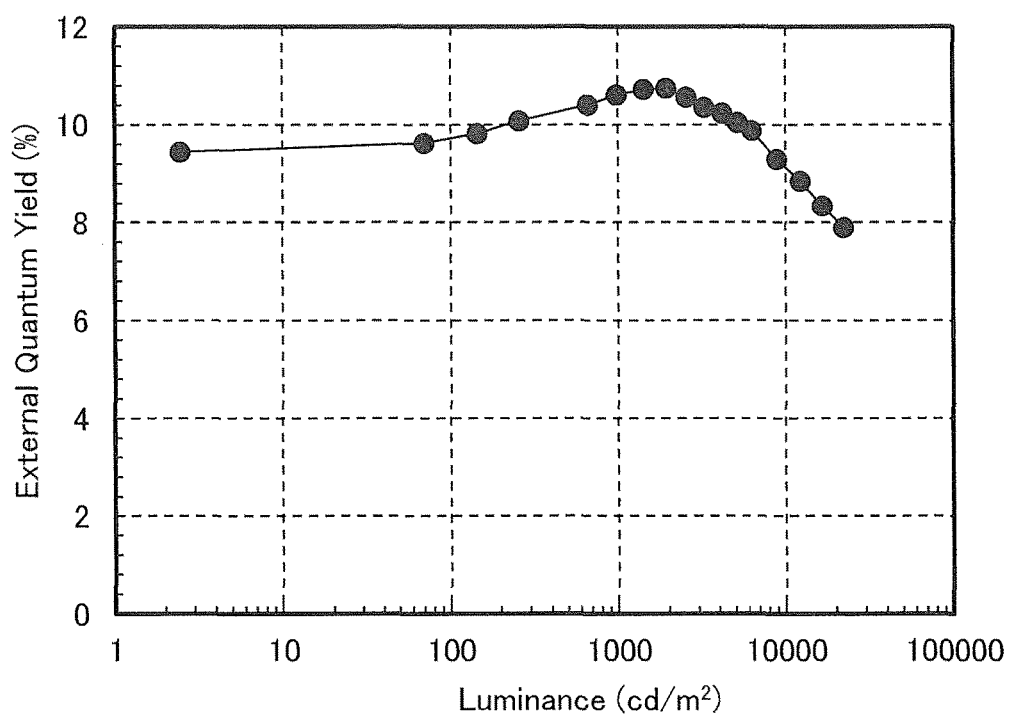
FIG. 19 shows the external quantum efficiency-luminance characteristics of Light-emitting Element 1.

FIG. 19 shows the external quantum efficiency-luminance characteristics of Light-emitting Element 1. Table 2 shows the main characteristics of Light-emitting Elements 1 and 1-1 at a luminance of about 1000 $cd/m^2$.

TABLE 2

| | Voltage (V) | Current (mA) | Current density ($mA/cm^2$) | chromaticity x | chromaticity y | Current Efficiency (cd/A) | External Quantum Efficiency (%) |
|---|---|---|---|---|---|---|---|
| Element 1 | 3.3 | 0.27 | 6.9 | 0.14 | 0.18 | 14 | 11 |
| Element 1-1 | 4.6 | 4.38 | 110 | 0.23 | 0.36 | 1.0 | 0.4 |

As shown in Table 2, Light-emitting Element 1 has a very high efficiency, e.g., an external quantum efficiency of 11%.

Light-emitting Element 1-1 includes the layer for adjusting the thickness in addition to the components of Light-emitting Element 1. By adjusting the optical path length, light that travels in the front direction is attenuated, so that a representing the orientation state can be easily obtained. A difference between the structure and the fabrication method of Light-emitting Element 1 and those of Light-emitting Element 1-1 lies only in the layer for adjusting the thickness; thus, the orientation states of light-emitting substances in the light-emitting layers are assumed to be the same.

Figure 20:
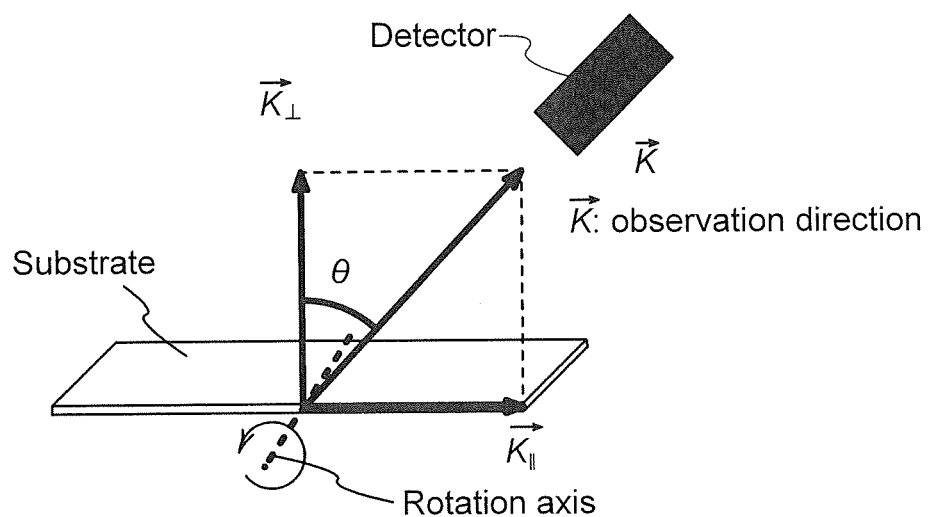
FIG. 20 shows a method for measuring the angle dependence of the emission spectrum.

The orientation state of a light-emitting material in the light-emitting layer was examined with the use of Light-emitting Element 1-1. First, the angle dependence of the shape of the EL emission spectrum was measured by measuring the EL spectrum in steps of 1° in such a manner that, as shown in FIG. 20, the substrate provided with Light-emitting Element 1-1 was inclined to a detector (a photonic multichannel analyzer PMA-12, produced by Hamamatsu Photonics K.K.) from θ=0° to 80°. In this measurement, a linear polarizer (Glan-Taylor prism) was disposed between Light-emitting Element 1-1 and the detector to be perpendicular to the substrate surface in order to remove an S polarization from light emitted from Light-emitting Element 1-1, so that the spectrum of only a P polarization was measured.

Figure 21:
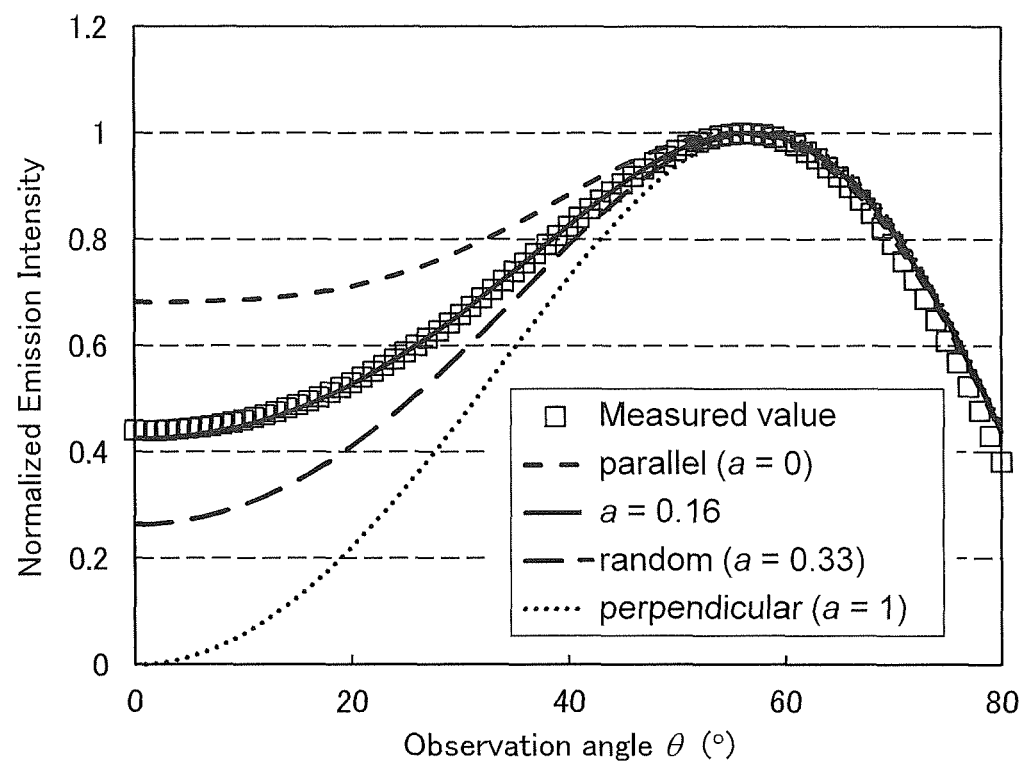
FIG. 21 is a graph showing the measured and calculated integrated intensity of the EL emission spectrum depending on the angle ($\theta$) of a detector of Light-emitting Element 1-1.

FIG. 21 is a graph in which the vertical axis represents the integrated intensity of the EL emission spectrum from 440 nm to 956 nm depending on the angle (θ) and the horizontal axis represents the angle (θ) of the detector. In FIG. 21, a curve plotted by open squares represents the measured values, and a solid curve and a dashed curve represent the calculation results obtained by setfos which is an organic device simulator. The calculation was performed by inputting the thickness of each layer in the element, the measured values of the refractive index and the extinction efficiency, the measured value of the emission spectrum of a dopant, the position and the width of a light-emitting region, and the orientation parameter a. Among them, the thickness of each layer, the refractive index, and the extinction efficiency were measured with the use of a spectroscopic ellipsometer (M-2000U, produced by J.A. Woollam Japan Corp.). For the measurement, a film was used which was formed of the light-emitting material over a quartz substrate by a vacuum evaporation method to a thickness of 150 nm. The emission spectrum of the dopant was measured using a fluorescence spectrophotometer (FS920, produced by Hamamatsu Photonics K.K.). For the measurement, a film was used which was formed by co-evaporation of cgDBCzPA and 1,6mMemFLPAPrn using a vacuum evaporation method at a weight ratio of 1:0.03 (=cgDBCzPA: 1,6mMemFLPAPrn) over a quartz substrate so that cgDBCzPA has a thickness of 50 nm. In the calculation by setfos, further, the light-emitting region was set. The light-emitting region was assumed to spread such that the recombination probability was attenuated exponentially in the cathode direction with the interface between the hole-transport layer and the light-emitting layer as a top, specifically, the recombination probability was attenuated to 1/e at a thickness of 10 nm. Thus, the angle dependence of the integrated intensity of the emission spectrum corresponding to each parameter a can be calculated. In Light-emitting Element 1-1, the measured value well fitted a curve of a=0.16.

Figure 22:
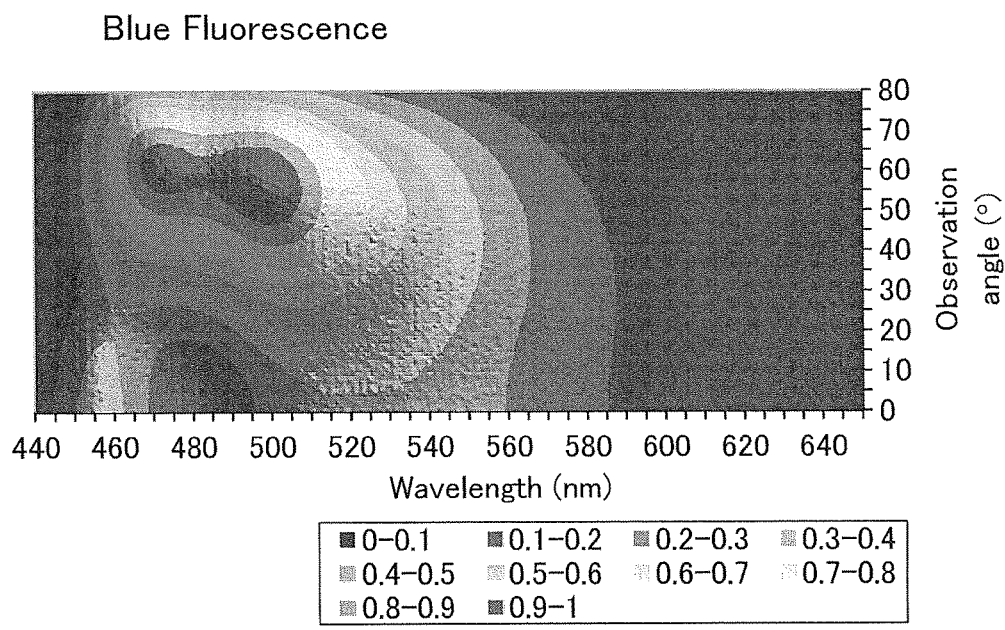
FIG. 22 is a 2D contour map showing the measured angle dependence of the EL emission spectrum of Light-emitting Element 1-1.
Figure 23:
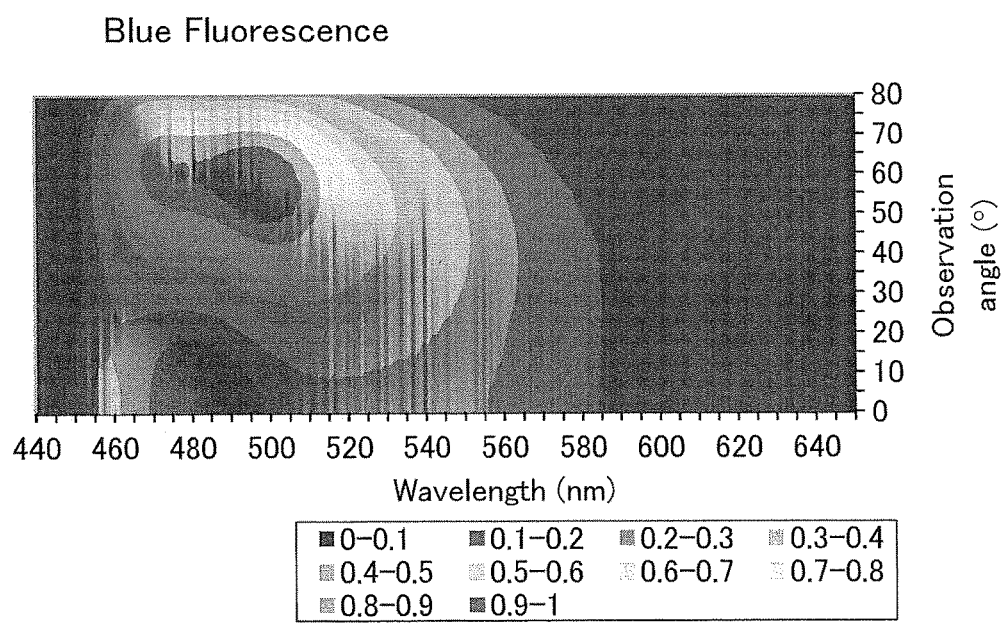
FIG. 23 is a 2D contour map obtained by calculation of Light-emitting Element 1-1.

FIG. 22 is a 2D contour map obtained by measuring the angle dependence of the EL emission spectrum of Light-emitting Element 1-1. FIG. 23 is a 2D contour map obtained by calculation. FIG. 22 and FIG. 23 show that these 2D contour maps match well. This indicates that the orientation of the light-emitting materials in Light-emitting Elements 1 and 1-1 was accurately obtained in both the experiment and the calculation.

The parameter a is 1/3≈0.33 in the case where the transition dipole is oriented in a random direction, and the parameter a is 0 in the case where the transition dipole is completely parallel to the substrate. The light extraction efficiency in the case of a=0 is 1.5 times the light extraction efficiency in the case of a=1/3≈0.33. In view of this, the light-emitting element of this example in which a=0.16 has light extraction efficiency that is 1.26 times the light extraction efficiency of the light-emitting element with a random orientation. That is, the light-emitting element of one embodiment of the present invention has an emission efficiency that is 1.26 times the emission efficiency of the light-emitting element with a random orientation.

Light-emitting Elements 1 and 1-1 are formed using the same material for their light-emitting layers by the same method; thus, it can be said that Light-emitting Element 1 has, like Light-emitting Element 1-1, an orientation of a=0.16. Light-emitting Element 1 has a very high external quantum efficiency of 11%. It is found that a light-emitting element with high emission efficiency can be obtained by setting a to less than or equal to 0.2. Measurement results of transient EL emission indicate that TTA also occurred in this element. The quantum yield of the film was 0.85 on average in the case of excitation light at 360 nm; the film was formed by co-evaporation of cgDBCzPA and 1,6mMemFLPAPrn using a vacuum evaporation method at a weight ratio of 1:0.03 (=cgDBCzPA: 1,6mMemFLPAPrn) so that cgDBCzPA has a thickness of 50 nm. That is, the light-emitting layer of this example has a parameter a of 0.2 or less and a fluorescent quantum yield of 0.84 or higher; thus, even when TTA does not occur, this layer satisfies theoretical conditions under which the external quantum efficiency can be higher than or equal to 7.5%. In addition to the above, since TTA occurs, a light-emitting element which has excellent characteristics, an external quantum efficiency of higher than 10%, was able to be obtained in this example.

Example 2

In this example, results of calculating the parameter a of a light-emitting element (Light-emitting Element 2) of one embodiment of the present invention with high efficiency are described in detail. For the above purpose, a light-emitting element (Light-emitting Element 2-1) for measurement which includes a light-emitting layer having the same structure as that of Light-emitting Element 2 and in which the luminance in the front direction is reduced as much as possible was also fabricated.

First, a fabrication method and the structure of the light-emitting element of one embodiment of the present invention are described. Organic compounds used in the light-emitting element of one embodiment of the present invention are given below.

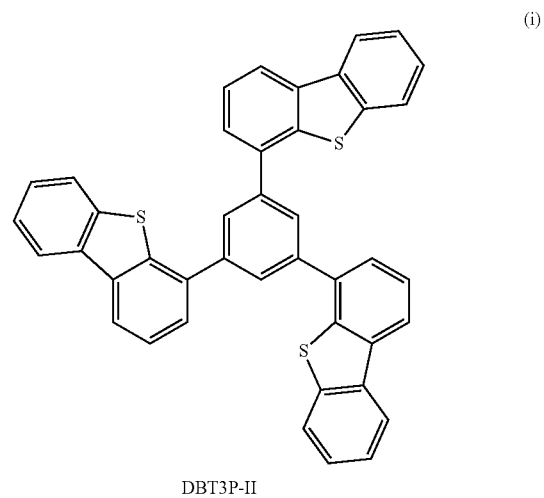

(i)

DBT3P-II (ii)

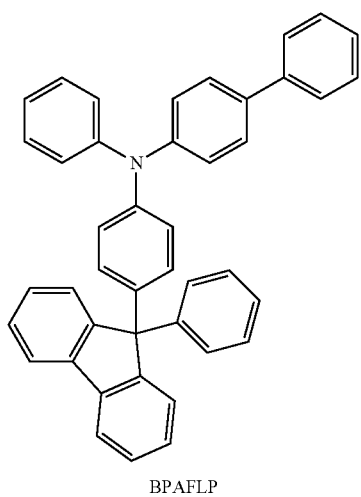

BPAFLP (vii)

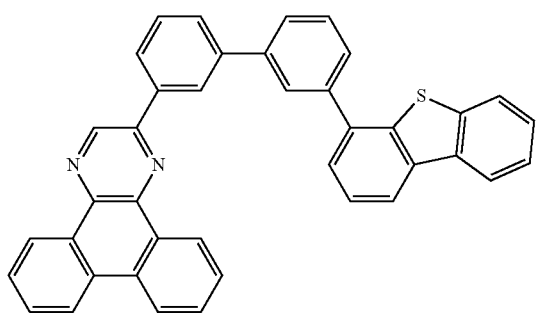

2mDBTBPDBq-II (viii)

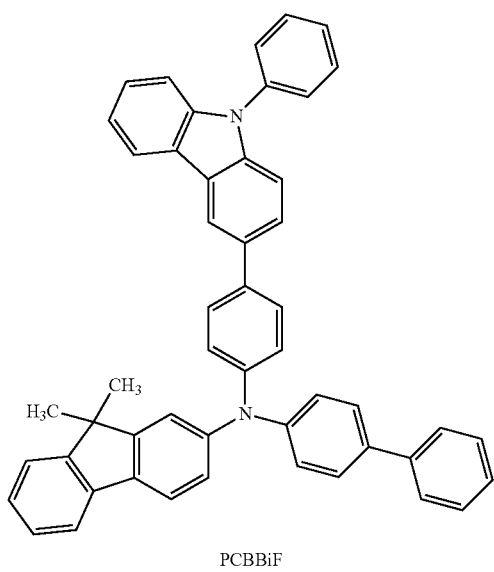

PCBBiF

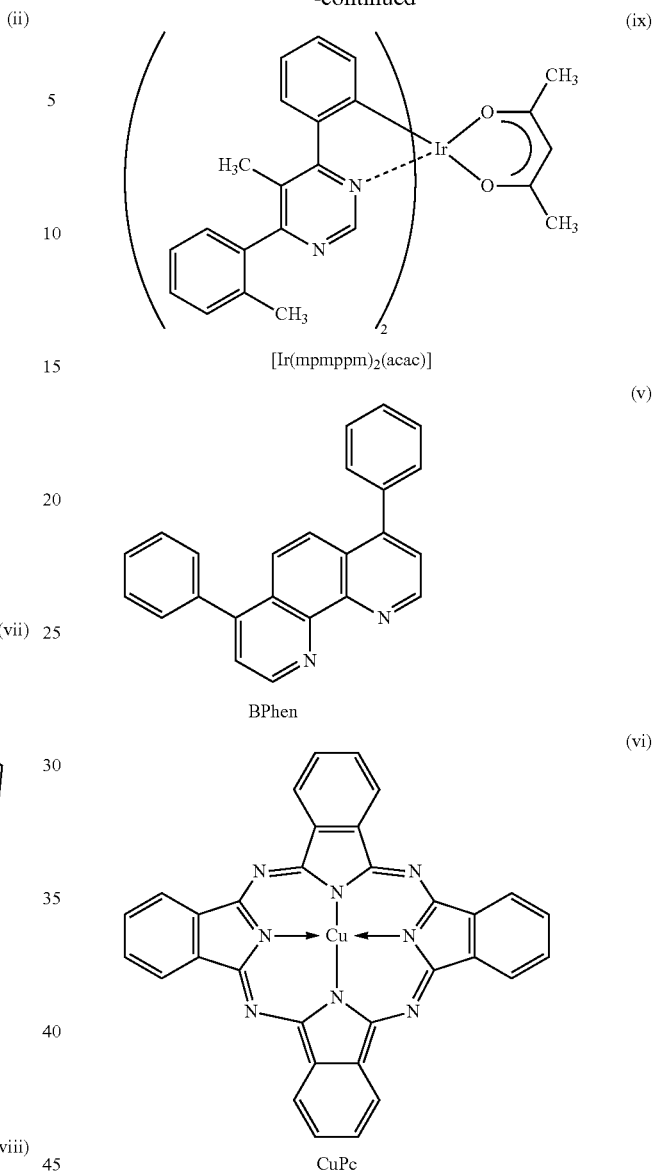

(ix) [Ir(mpmppm)$_2$(acac)]

(v) BPhen (vi) CuPc (Fabrication Method of Light-Emitting Element 2)

First, a film of indium tin oxide containing silicon oxide (ITSO) was formed over a glass substrate by a sputtering method, so that the first electrode 101 was formed. The thickness of the first electrode 101 was 70 nm and the electrode area was 2 mm×2 mm.

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus where the pressure had been reduced to approximately 10$^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 4,4',4"-(benzene-1,3,5-triyl)tri(dibenzothiophene) (abbreviation: DBT3P-II) represented by Structural Formula (i) and molybdenum(VI) oxide were deposited by co-evaporation to a thickness of 50 nm at a weight ratio of 4:2 (=DBT3P-II: molybdenum oxide) by an evaporation method using resistance heating, so that the hole-injection layer 111 was formed.

Next, a film of 4-phenyl-4'-(9-phenylfluoren-9-yl)triphenylamine (abbreviation: BPAFLP) represented by Structural Formula (ii) was formed by evaporation to a thickness of 20 nm on the hole-injection layer 111 to form the hole-transport layer 112.

After that, the light-emitting layer 113 was formed in the following manner: 2-[3'-(dibenzothiophen-4-yl)biphenyl-3-yl]dibenzo[/h]quinoxaline (abbreviation: 2mDBTBPDBq-II) represented by Structural Formula (vii), N-(1,1'-biphenyl-4-yl)-9,9-dimethyl-N-[4-(9-phenyl-9H-carbazol-3-yl)phenyl]-9H-fluor en-2-amine (abbreviation: PCBBiF) represented by Structural Formula (viii), and bis{2-[5-methyl-6-(2-methylphenyl)-4-pyrimidinyl-κN3]phenyl-κC}(2,4-pentanedionato-$\kappa^2$O,O')iridium(III) (abbreviation: [Ir(mpmppm)$_2$(acac)]) represented by Structural Formula (ix) were deposited by co-evaporation at a weight ratio of 0.8:0.2:0.05 (=2mDBTBPDBq-II:PCBBiF:[Ir(mpmppm)$_2$(acac)]) to a thickness of 40 nm. In the step of forming the light-emitting layer 113 (at the time of evaporation), the total pressure was approximately $2 \times 10^{-4}$ Pa and the partial pressure of carbon dioxide whose molecular weight was detected as 44 was approximately $1 \times 10^{-6}$ Pa when the measurement was performed by Q-mass provided in an evaporation chamber. That is, the percentage of the partial pressure of carbon dioxide with respect to the total pressure at the time of evaporation was approximately 0.5%. In this manner, it is important that the percentage of the partial pressure of carbon dioxide with respect to the total pressure at the time of evaporation is higher than 0.03%, specifically, higher than or equal to 0.1%. Since only gases whose molecular weight is 1 to 200 can be detected by Q-mass, the total pressure measured by Q-mass is, strictly speaking, different from a practical total pressure in the chamber. The partial pressure of gas components whose molecular weight exceeds 200 is negligible; thus, with the use of either the total pressure measured by Q-mass or the practical total pressure in the chamber, similar results can be obtained.

Then, on the light-emitting layer 113, 2mDBTBPDBq-II was deposited by evaporation to a thickness of 25 nm, and bathophenanthroline (abbreviation: BPhen) represented by Structural Formula (v) was deposited by evaporation to a thickness of 10 nm to form the electron-transport layer 114.

After the formation of the electron-transport layer 114, lithium oxide (Li$_2$O) was deposited by evaporation to a thickness of 0.1 nm to form the electron-injection layer 115. Then, aluminum was deposited by evaporation to a thickness of 200 nm to form the second electrode 102. Through the above-described steps, Light-emitting Element 2 of this example was fabricated.

(Fabrication Method of Light-Emitting Element 2-1)

Light-emitting Element 2-1 was fabricated in the following manner. After the electron-injection layer 115 of Light-emitting Element 2 was formed, copper phthalocyanine (abbreviation: CuPc) represented by Structural Formula (vi) was deposited by evaporation to a thickness of 2 nm, and then, DBT3P-II and molybdenum(VI) oxide were deposited by co-evaporation at a weight ratio of 2:1 (=DBT3P-II: molybdenum oxide) to a thickness of 85 nm. In such a manner, a layer for adjusting the thickness was formed.

The element structures of Light-emitting elements 2 and 2-1 are shown in the following table.

TABLE 3

|  | hole-injection layer | hole-transport layer | light-emitting layer | electron-transport layer | electron-injection layer | layer for adjusting the thickness | |
|---|---|---|---|---|---|---|---|
|  | 50 nm | 20 nm | 40 nm | 25 nm | 10 nm | 0.1 nm | 2 nm | 85 nm |
| Element 2 | DBT3P-II:MoOx (4:2) | BPAFLP | 2mDBTBPDBq-II: PCBBiF: [Ir(mpmppm)$_2$(acac)] (0.8:0.2:0.05) | 2mDBTBPDBq-II | BPhen | Li$_2$O | — | — |
| Element 2-1 |  |  |  |  |  |  | CuPc | DBT3P-II:MoOx (4:2) |

Light-emitting Elements 2 and 2-1 were each sealed using a glass substrate in a glove box containing a nitrogen atmosphere so as not to be exposed to the air (specifically, a sealant was applied to surround the element and UV treatment and heat treatment at 80° C. for 1 hour were performed at the time of sealing). Then, the initial characteristics of Light-emitting Elements 2 and 2-1 were measured. Note that the measurement was carried out in an atmosphere kept at 25° C.

FIG. 24 shows the external quantum efficiency-luminance characteristics of Light-emitting Element 2. Table 4 shows the main characteristics of Light-emitting Elements 2 and 2-1 at a luminance of about 1000 cd/m$^2$.

TABLE 4

|  | Voltage | Current | Current density | chromaticity | | Current Efficiency | External Quantum Efficiency |
|---|---|---|---|---|---|---|---|
|  | (V) | (mA) | (mA/cm$^2$) | x | y | (cd/A) | (%) |
| Element 2 | 2.8 | 0.03 | 0.8 | 0.49 | 0.50 | 105 | 30 |
| Element 2-1 | 4.2 | 0.90 | 23 | 0.49 | 0.50 | 4.1 | 2.5 |

As shown in Table 4, Light-emitting Element 2 has a very high efficiency, e.g., an external quantum efficiency of 30%. The light-emitting material used in Light-emitting Element 2, [Ir(mpmppm)$_2$(acac)], has an emission quantum yield (ϕ)

of 0.84. Assuming that the carrier balance (γ) is 1 and the proportion of generated excitons (α) is 1, the light extraction efficiency (χ) is calculated to 35.7%, which is much higher than a general theoretical light extraction efficiency of 20% to 30%.

Light-emitting Element 2-1 includes the layer for adjusting the thickness in addition to the components of Light-emitting Element 2. By adjusting the optical path length, light that travels in the front direction is attenuated, so that a representing the orientation state can be easily obtained. A difference between the structure and the fabrication method of Light-emitting Element 2 and those of Light-emitting Element 2-1 lies only in the layer for adjusting the thickness; thus, the orientation states of light-emitting substances in the light-emitting layers are assumed to be the same.

The orientation state of a light-emitting material in the light-emitting layer was examined with the use of Light-emitting Element 2-1. First, the angle dependence of the shape of the EL emission spectrum was measured by measuring the EL spectrum in steps of 1° in such a manner that, as shown in FIG. 20, the substrate provided with Light-emitting Element 2-1 was inclined to a detector (a photonic multichannel analyzer PMA-12, produced by Hamamatsu Photonics K.K.) from θ=0° to 80°. In this measurement, a linear polarizer (Glan-Taylor prism) was disposed between Light-emitting Element 2-1 and the detector to be perpendicular to the substrate surface in order to remove an S polarization from light emitted from Light-emitting Element 2-1, so that the spectrum of only a P polarization was measured.

FIG. 25 is a graph in which the vertical axis represents the integrated intensity of the EL emission spectrum from 440 nm to 956 nm depending on the angle (θ) and the horizontal axis represents the angle (θ) of the detector. In FIG. 25, a curve plotted by open squares represents the measured values, and a solid curve and a dashed curve represent the calculation results obtained by setfos which is an organic device simulator. The calculation was performed by inputting the thickness of each layer in the element, the measured values of the refractive index and the extinction efficiency, the measured value of the emission spectrum of a dopant, the position and the width of a light-emitting region, and the orientation parameter a. Among them, the thickness of each layer, the refractive index, and the extinction efficiency were measured with the use of a spectroscopic ellipsometer (M-2000U, produced by J.A. Woollam Japan Corp.). For the measurement, a film was used which was formed of the light-emitting material over a quartz substrate by a vacuum evaporation method to a thickness of 150 nm. The emission spectrum of the dopant was measured using a fluorescence spectrophotometer (FS920, produced by Hamamatsu Photonics K.K.). For the measurement, a film was used which was formed by co-evaporation of 2mDBTBPDBq-II, PCBBiF, and Ir(mpmppm)$_2$(acac) using a vacuum evaporation method at a weight ratio of 0.8:0.2:0.05 (=2mDBTBPDBq-II:PCBBiF:Ir(mpmppm)$_2$(acac)) over a quartz substrate to a thickness of 50 nm. In the calculation by setfos, further, the light-emitting region was set. The light-emitting region was assumed to spread such that the recombination probability was attenuated exponentially in the cathode direction with the interface between the hole-transport layer and the light-emitting layer as a top, specifically, the recombination probability was attenuated to 1/e at a thickness of 25 nm. Thus, the angle dependence of the integrated intensity of the emission spectrum corresponding to each parameter a can be calculated In Light-emitting Element 2-1, the measured value well fitted a curve of a=0.18.

Figure 26:
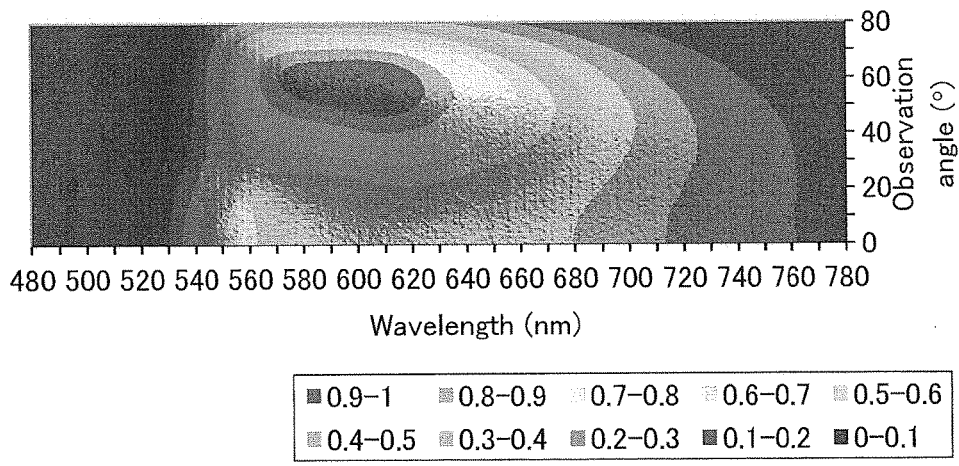
FIG. 26 is a 2D contour map showing the measured angle dependence of the EL emission spectrum of Light-emitting Element 2-1.
Figure 27:
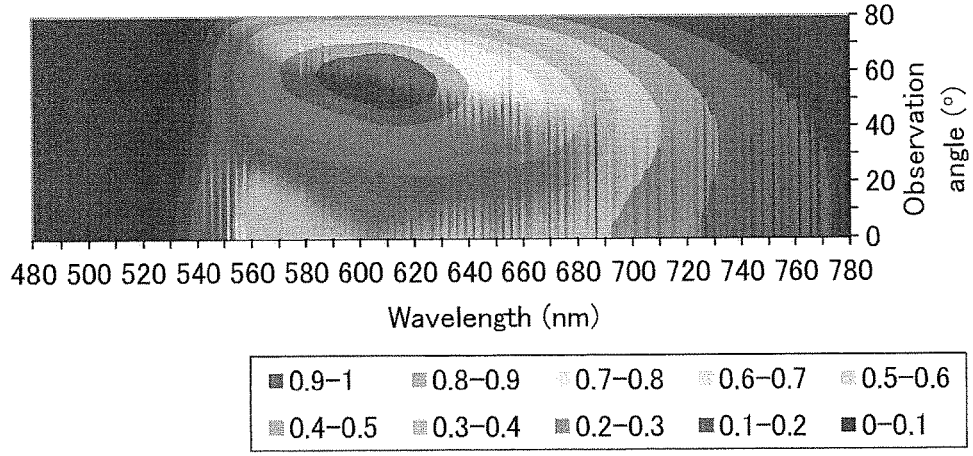
FIG. 27 is a 2D contour map obtained by calculation of Light-emitting Element 2-1.

FIG. 26 is a 2D contour map obtained by measuring the angle dependence of the EL emission spectrum of Light-emitting Element 2-1. FIG. 27 is a 2D contour map obtained by calculation. FIG. 26 and FIG. 27 show that these 2D contour maps match well. This indicates that the orientation of the light-emitting materials in Light-emitting Elements 2 and 2-1 was accurately obtained in both the experiment and the calculation.

The parameter a is ⅓≈0.33 in the case where the transition dipole is oriented in a random direction, and the parameter a is 0 in the case where the transition dipole is completely parallel to the substrate. The light extraction efficiency in the case of a=0 is 1.5 times the light extraction efficiency in the case of a=⅓≈0.33. In view of this, the light-emitting element of this example in which a=0.18 has light extraction efficiency that is 1.23 times the light extraction efficiency of the light-emitting element with a random orientation.

Light-emitting Elements 2 and 2-1 are formed using the same material for their light-emitting layers by the same method; thus, it can be said that Light-emitting Element 2 has, like Light-emitting Element 2-1, an orientation of a=0.18. Light-emitting Element 2 has a very high external quantum efficiency of 30%. It is found that a light-emitting element with high emission efficiency can be obtained by setting a to less than or equal to 0.2. The quantum yield of the film was 0.84 on average in the case of excitation light at 370 nm; the film was formed by co-evaporation of 2mDBTBPDBq-II, PCBBiF, and Ir(mpmppm)$_2$(acac) using a vacuum evaporation method at a weight ratio of 0.8:0.2:0.05 (=2mDBTBPDBq-II:PCBBiF:Ir(mpmppm)$_2$(acac)) to a thickness of 50 nm. That is, the light-emitting layer of this example has a parameter a of 0.2 or less and a phosphorescent quantum yield of 0.84 or higher; thus, this layer satisfies theoretical conditions under which the external quantum efficiency can be higher than or equal to 30%.

Example 3

In this example, results of calculating the parameter a of a light-emitting element (Light-emitting Element 3) of one embodiment of the present invention with high efficiency are described in detail. For the above purpose, a light-emitting element (Light-emitting Element 3-1) for measurement which includes a light-emitting layer having the same structure as that of Light-emitting Element 3 and in which the luminance in the front direction is reduced as much as possible was also fabricated.

First, a fabrication method and the structure of the light-emitting element of one embodiment of the present invention are described. Organic compounds used in the light-emitting element of one embodiment of the present invention are given below.

(i)
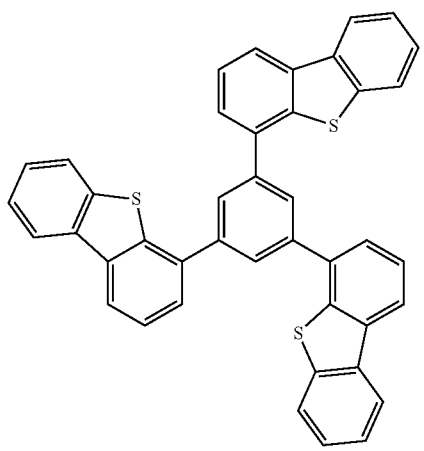
DBT3P-II
(ii)
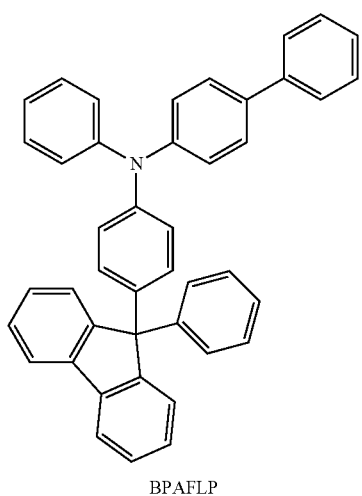
BPAFLP
(vii)
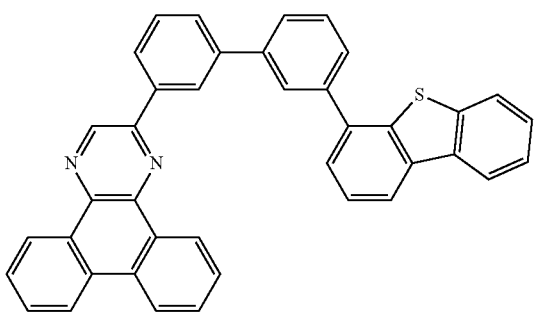
2mDBTBPDBq-II
(viii)
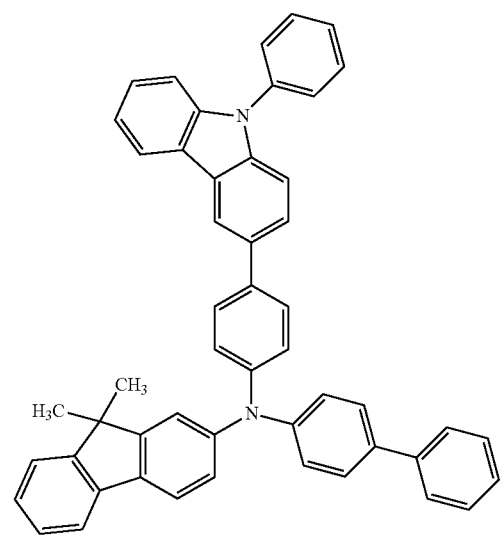
PCBBiF
(x)
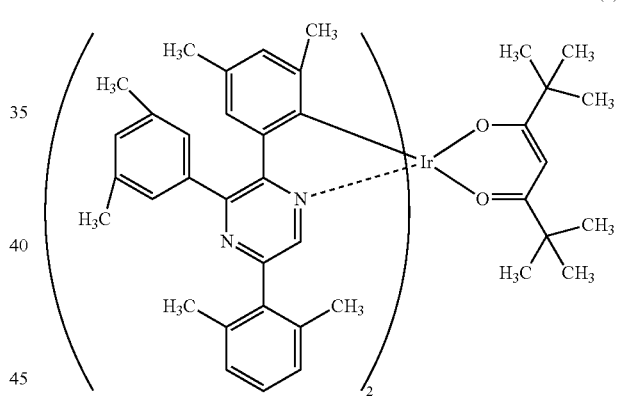
[Ir(dmdppr-dmp)₂(dpm)]
(v)
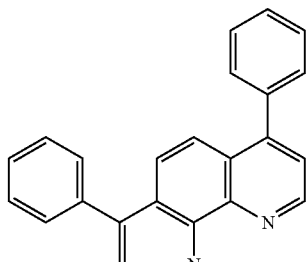
BPhen -continued

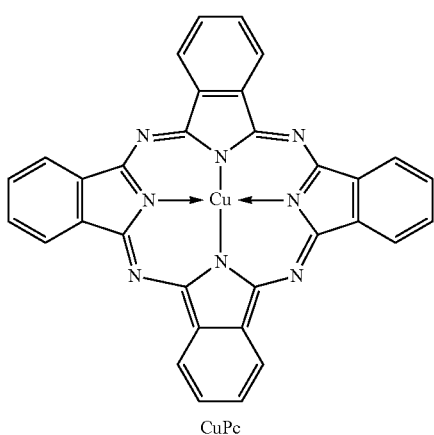

CuPc (vi)

(Fabrication Method of Light-Emitting Element 3)

First, a film of indium tin oxide containing silicon oxide (ITSO) was formed over a glass substrate by a sputtering method, so that the first electrode 101 was formed. The thickness of the first electrode 101 was 70 nm and the electrode area was 2 mm×2 mm.

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 4,4',4''-(benzene-1,3,5-triyl)tri(dibenzothiophene) (abbreviation: DBT3P-II) represented by Structural Formula (i) and molybdenum(VI) oxide were deposited by co-evaporation to a thickness of 75 nm at a weight ratio of 2:1 (=DBT3P-II: molybdenum oxide) by an evaporation method using resistance heating, so that the hole-injection layer 111 was formed.

Next, 4-phenyl-4'-(9-phenylfluoren-9-yl)triphenylamine (abbreviation: BPAFLP) represented by Structural Formula (ii) was deposited by evaporation to a thickness of 20 nm on the hole-injection layer 111 to form the hole-transport layer 112.

Then, the light-emitting layer 113 was formed in the following manner: 2-[3'-(dibenzothiophen-4-yl)biphenyl-3-yl]dibenzo[f,h]quinoxaline (abbreviation: 2mDBTBPDBq-II) represented by Structural Formula (vii), N-(1,1'-biphenyl-4-yl)-9,9-dimethyl-N-[4-(9-phenyl-9H-carbazol-3-yl)phenyl]-9H-fluor en-2-amine (abbreviation: PCBBiF) represented by Structural Formula (viii), and bis{2-[5-(2,6-dimethylphenyl)-3-(3,5-dimethylphenyl)-2-pyrazinyl-1N]-4,6-dimethylphenyl-κC}(2,2,6,6-tetramethyl-3,5-heptanedionato-κ²O,O')iridium(III) (abbreviation: [Ir(dmdppr-dmp)$_2$(dpm)]) represented by Structural Formula (x) were deposited by co-evaporation at a weight ratio of 0.8:0.2:0.05 (=2mDBTBPDBq-II:PCBBiF:[Ir(dmdppr-dmp)$_2$(dpm)]) to a thickness of 40 nm.

Then, on the light-emitting layer 113, 2mDBTBPDBq-II was deposited by evaporation to a thickness of 30 nm, and bathophenanthroline (abbreviation: BPhen) represented by Structural Formula (v) was deposited by evaporation to a thickness of 15 nm to form the electron-transport layer 114.

After the formation of the electron-transport layer 114, lithium oxide ($Li_2O$) was deposited by evaporation to a thickness of 0.1 nm to form the electron-injection layer 115. Then, aluminum was deposited by evaporation to a thickness of 200 nm to form the second electrode 102. Through the above-described steps, Light-emitting Element 3 of this example was fabricated.

(Fabrication Method of Light-Emitting Element 3-1)

Light-emitting element 3-1 was fabricated in the following manner. After the electron-injection layer 115 of Light-emitting Element 3 was formed, copper phthalocyanine (abbreviation: CuPc) represented by Structural Formula (vi) was deposited by evaporation to a thickness of 2 nm, and then, DBT3P-II and molybdenum(VI) oxide were deposited by co-evaporation at a weight ratio of 2:1 (=DBT3P-II: molybdenum oxide) to a thickness of 100 nm. In such a manner, a layer for adjusting the thickness was formed.

The element structures of Light-emitting Elements 3 and 3-1 are shown in the following table.

TABLE 5

| | hole-injection layer | hole-transport layer | light-emitting layer | electron-transport layer | | electron-injection layer | layer for adjusting the thickness | |
|---|---|---|---|---|---|---|---|---|
| | 75 nm | 20 nm | 40 nm | 30 nm | 15 nm | 0.1 nm | 2 nm | 90 nm |
| Element 3 | DBT3P-II:MoOx (4:2) | BPAFLP | 2mDBTBPDBq-II: PCBBiF: [Ir(dmdppr-dmp)$_2$(dpm)] (0.8:0.2:0.05) | 2mDBTBPDBq-II | BPhen | Li$_2$O | — | — |
| Element 3-1 | | | | | | | CuPc | DBT3P-II:MoOx (4:2) |

Light-emitting elements 3 and 3-1 were each sealed using a glass substrate in a glove box containing a nitrogen atmosphere so as not to be exposed to the air (specifically, a sealant was applied to surround the element and UV treatment and heat treatment at 80° C. for 1 hour were performed at the time of sealing). Then, the initial characteristics of Light-emitting elements 3 and 3-1 were measured. Note that the measurement was carried out in an atmosphere kept at 25° C.

Figure 28:
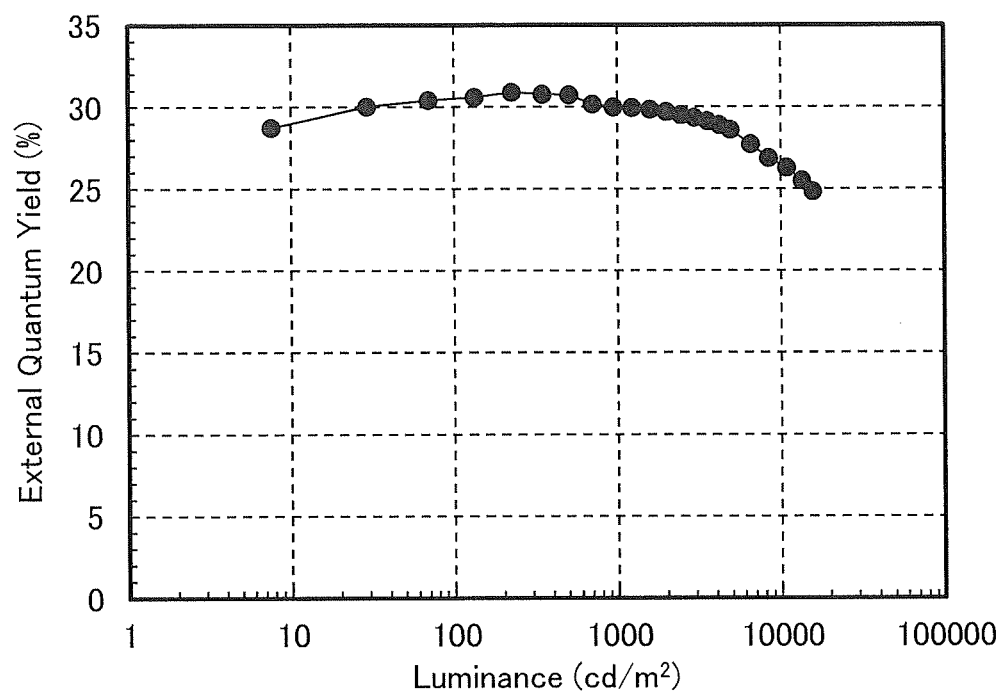
FIG. 28 shows the external quantum efficiency-luminance characteristics of Light-emitting Element 3.

FIG. 28 shows the external quantum efficiency-luminance characteristics of Light-emitting Element 3. Table 6 shows the main characteristics of Light-emitting Elements 3 and 3-1 at a luminance of about 1000 cd/m².

TABLE 6

|  | Voltage | Current | Current density | chromaticity | | Current Efficiency | External Quantum Efficiency |
| --- | --- | --- | --- | --- | --- | --- | --- |
|  | (V) | (mA) | (mA/cm$^2$) | x | y | (cd/A) | (%) |
| Element 3 | 3.2 | 0.10 | 2.5 | 0.67 | 0.33 | 38 | 27 |
| Element 3-1 | 5.0 | 1.77 | 44 | 0.62 | 0.35 | 1.2 | 2.0 |

As shown in Table 6, Light-emitting Element 3 has a very high efficiency, e.g., an external quantum efficiency of 27%. The light-emitting material used in Light-emitting Element 3, [Ir(dmdppr-dmp)$_2$(dpm)], has an emission quantum yield (φ) of 0.79. Assuming that the carrier balance (γ) is 1 and the proportion of generated excitons (α) is 1, the light extraction efficiency (χ) is calculated to 34.1%, which is much higher than a general theoretical light extraction efficiency of 20% to 30%.

Light-emitting Element 3-1 includes the layer for adjusting the thickness in addition to the components of Light-emitting Element 3. By adjusting the optical path length, light that travels in the front direction is attenuated, so that a representing the orientation state can be easily obtained. A difference between the structure and the fabrication method of Light-emitting Element 3 and those of Light-emitting Element 3-1 lies only in the layer for adjusting the thickness; thus, the orientation states of light-emitting substances in the light-emitting layers are assumed to be the same.

The orientation state of a light-emitting material in the light-emitting layer was examined with the use of Light-emitting Element 3-1. The method is the same as those in Examples 1 and 2 and its description is thus omitted.

Figure 29:
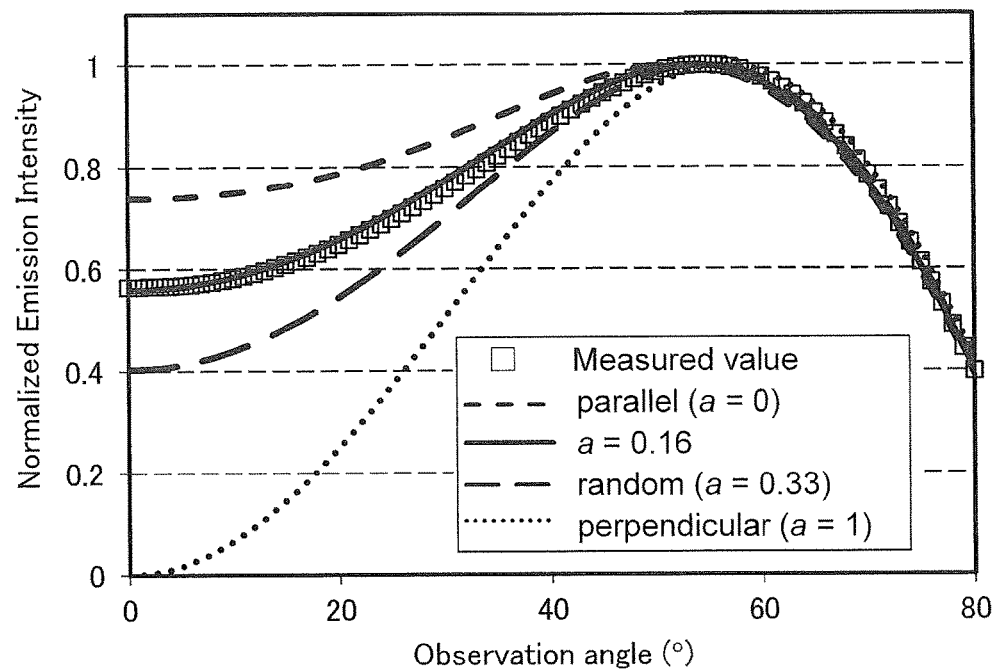
FIG. 29 is a graph showing the measured and calculated integrated intensity of the EL emission spectrum depending on the angle ($\theta$) of the detector of Light-emitting Element 3-1.

FIG. 29 is a graph in which the vertical axis represents the integrated intensity of the EL emission spectrum from 570 nm to 900 nm depending on the angle (θ) and the horizontal axis represents the angle (θ) of the detector. In FIG. 29, a curve plotted by open squares represents the measured values, and a solid curve and a dashed curve represent the calculation results obtained by setfos which is an organic device simulator. The calculation was performed by inputting the thickness of each layer in the element, the measured values of the refractive index and the extinction efficiency, the measured value of the emission spectrum of a dopant, the position and the width of a light-emitting region, and the orientation parameter a. Among them, the thickness of each layer, the refractive index, and the extinction efficiency were measured with the use of a spectroscopic ellipsometer (M-2000U, produced by J.A. Woollam Japan Corp.). For the measurement, a film was used which was formed of the light-emitting material over a quartz substrate by a vacuum evaporation method to a thickness of 150 nm. The emission spectrum of the dopant was measured using a fluorescence spectrophotometer (FS920, produced by Hamamatsu Photonics K.K.). For the measurement, a film was used which was formed by co-evaporation of 2mDBTBPDBq-II, PCBBiF, and [Ir(dmdppr-dmp)$_2$(dpm)] using a vacuum evaporation method at a weight ratio of 0.8:0.2:0.05 (=2mDBT-BPDBq-II:PCBBiF:[Ir(dmdppr-dmp)$_2$(dpm)]) over a quartz substrate to a thickness of 50 nm. In the calculation by setfos, further, the light-emitting region was set. The light-emitting region was assumed to spread such that the recombination probability was attenuated in accordance with the Gaussian distribution with a point which is approximately 38 nm from the interface between the hole-transport layer and the light-emitting layer as a top, specifically, the distance between inflection points of an assumed Gaussian function was 28 nm. Thus, the angle dependence of the integrated intensity of the emission spectrum corresponding to each parameter a can be calculated. In Light-emitting Element 3-1, the measured value well fitted a curve of a=0.16.

Figure 30:
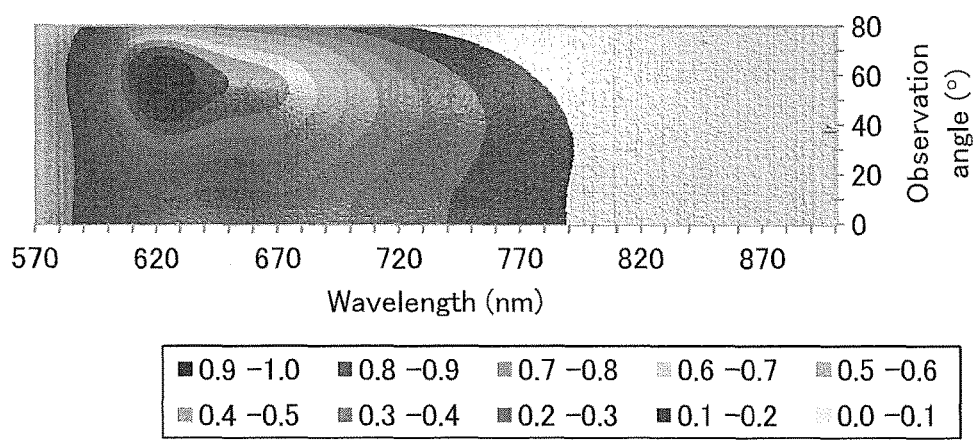
FIG. 30 is a 2D contour map showing the measured angle dependence of the EL emission spectrum of Light-emitting Element 3-1.
Figure 31:
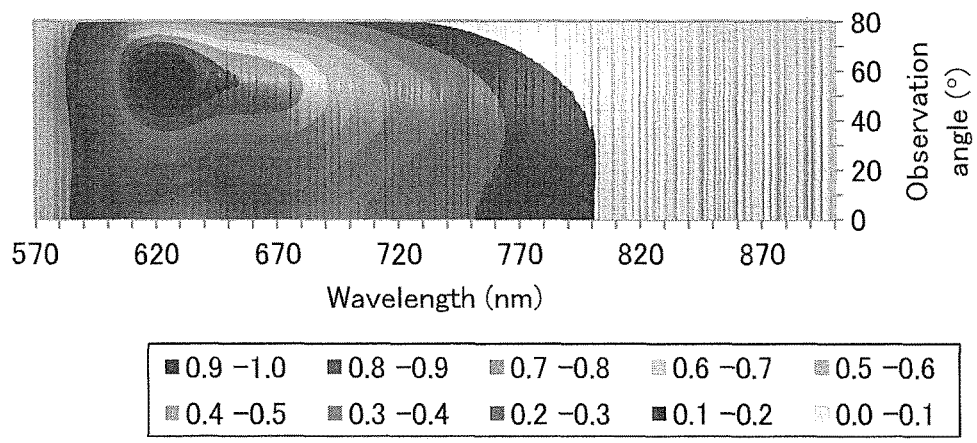
FIG. 31 is a 2D contour map obtained by calculation of Light-emitting Element 3-1.

FIG. 30 is a 2D contour map obtained by measuring the angle dependence of the EL emission spectrum of Light-emitting Element 3-1. FIG. 31 is a 2D contour map obtained by calculation. FIG. 30 and FIG. 31 show that these 2D contour maps match well. This indicates that the orientation of the light-emitting materials in Light-emitting Elements 3 and 3-1 was accurately obtained in both the experiment and the calculation.

The parameter a is ⅓≈0.33 in the case where the transition dipole is oriented in a random direction, and the parameter a is 0 in the case where the transition dipole is completely parallel to the substrate. The light extraction efficiency in the case of a=0 is 1.5 times the light extraction efficiency in the case of a=⅓≈0.33. In view of this, the light-emitting element of this example in which a=0.16 has light extraction efficiency that is 1.26 times the light extraction efficiency of the light-emitting element with a random orientation.

Light-emitting Elements 3 and 3-1 are formed using the same material for their light-emitting layers by the same method; thus, it can be said that, thanks to [Ir(dmdppr-dmp)$_2$(dpm)] in the light-emitting layer, Light-emitting Element 3 has, like Light-emitting Element 3-1, an orientation of a=0.16. Light-emitting Element 3 has a very high external quantum efficiency of 27%. It is found that a light-emitting element with high emission efficiency can be obtained by setting a to less than or equal to 0.2.

Example 4

In this example, results of calculating the parameter a of a light-emitting element (Light-emitting Element 4) of one embodiment of the present invention with high efficiency are described in detail. For the above purpose, a light-emitting element (Light-emitting Element 4-1) for measurement which includes a light-emitting layer having the same structure as that of Light-emitting Element 4 and in which the luminance in the front direction is reduced as much as possible was also fabricated.

First, a fabrication method and the structure of the light-emitting element of one embodiment of the present invention are described. Organic compounds used in the light-emitting element of one embodiment of the present invention are given below.

(i)
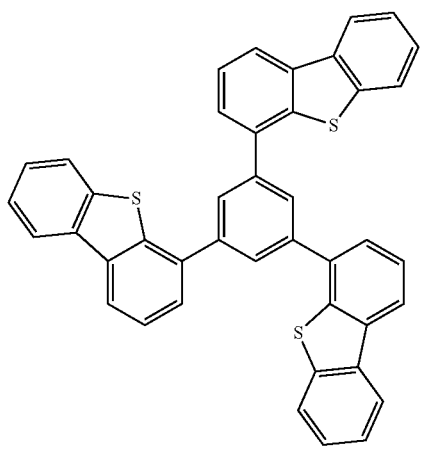
DBT3P-II (xi)
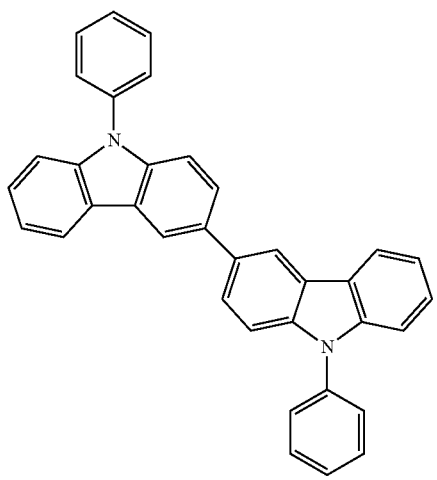
PCCP (xii)
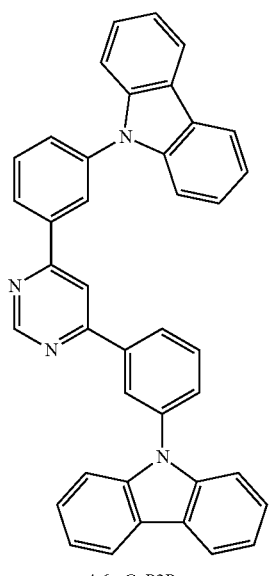
4,6mCzP2Pm

-continued (xiii)
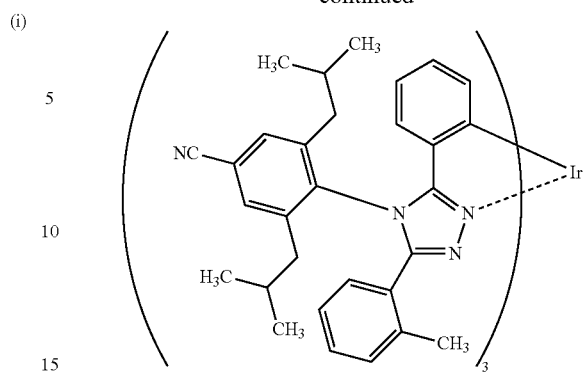
Ir(mpptz-diBuCNp)₃

(v)
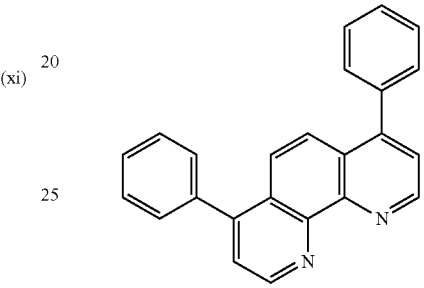
BPhen (vi)
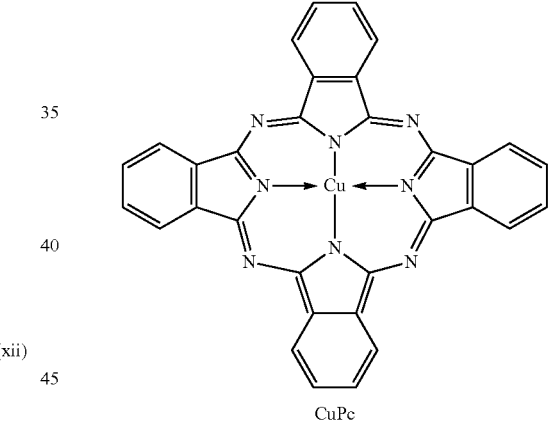
CuPc (Fabrication Method of Light-Emitting Element 4)

First, a film of indium tin oxide containing silicon oxide (ITSO) was formed over a glass substrate by a sputtering method, so that the first electrode 101 was formed. The thickness of the first electrode 101 was 70 nm and the electrode area was 2 mm×2 mm.

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 4,4',4"-(benzene-1,3,5-triyl)tri(dibenzothiophene) (abbreviation: DBT3P-II) represented by Structural Formula (i) and molybdenum(VI) oxide were deposited by co-evaporation to a thickness of 20 nm at a weight ratio of 2:1 (=DBT3P-II: molybdenum oxide) by an evaporation method using resistance heating, so that the hole-injection layer 111 was formed.

Next, 3,3'-bis(9-phenyl-9H-carbazole) (abbreviation: PCCP) represented by Structural Formula (xi) was deposited by evaporation to a thickness of 20 nm on the hole-injection layer 111 to form the hole-transport layer 112.

Then, the light-emitting layer 113 was formed in the following manner: PCCP, 4,6-bis[3-(9H-carbazol-9-yl)phenyl]pyrimidine (abbreviation: 4,6mCzP2Pm) represented by Structural Formula (xii), and tris{2-[4-(4-cyano-2,6-diisobutylphenyl)-5-(2-methylphenyl)-4H-1,2,4-triazol-3-yl-$\kappa N^2$]phenyl-$\kappa C$}iridium(III) (abbreviation: [Ir(mpptz-diBuCNp)$_3$]) represented by Structural Formula (xiii) were deposited by co-evaporation to a thickness of 30 nm at a weight ratio of 0.6:0.4:0.125 (=PCCP: 4,6mCzP2Pm: [Ir(mpptz-diBuCNp)$_3$]), and then, PCCP, 4,6mCzP2Pm, and [Ir(mpptz-diBuCNp)$_3$] were deposited by co-evaporation to a thickness of 10 nm at a weight ratio of 0.2:0.8:0.125 (=PCCP: 4,6mCzP2Pm: [Ir(mpptz-diBuCNp)$_3$]).

Then, on the light-emitting layer 113, 4,6mCzP2Pm was deposited by evaporation to a thickness of 10 nm, and bathophenanthroline (abbreviation: BPhen) represented by Structural Formula (v) was deposited by evaporation to a thickness of 15 nm to form the electron-transport layer 114.

After the formation of the electron-transport layer 114, lithium oxide (Li$_2$O) was deposited by evaporation to a thickness of 0.1 nm to form the electron-injection layer 115. Then, aluminum was deposited by evaporation to a thickness of 200 nm to form the second electrode 102. Through the above-described steps, Light-emitting Element 4 of this example was fabricated.

(Fabrication Method of Light-Emitting Element 4-1)

Light-emitting element 4-1 was fabricated in the following manner. After the electron-injection layer 115 of Light-emitting Element 4 was formed, copper phthalocyanine (abbreviation: CuPc) represented by Structural Formula (vi) was deposited by evaporation to a thickness of 2 nm, and then, DBT3P-II and molybdenum(VI) oxide were deposited by co-evaporation at a weight ratio of 2:1 (=DBT3P-II: molybdenum oxide) to a thickness of 55 nm. In such a manner, a layer for adjusting the thickness was formed.

The element structures of Light-emitting Elements 4 and 4-1 are shown in the following table.

TABLE 7

| | hole-injection layer | hole-transport layer | light-emitting layer | | electron-transport layer | | electron-injection layer | layer for adjusting the thickness | |
|---|---|---|---|---|---|---|---|---|---|
| | 20 nm | 20 nm | 30 nm | 10 nm | 10 nm | 15 nm | 0.1 nm | 2 nm | 55 nm |
| Element 4 | DBT3P-II:MoOx (4:2) | PCCP | *1 | *2 | 4,6mCzP2Pm | BPhen | Li$_2$O | — | — |
| Element 4-1 | | | | | | | | CuPc | DBT3P-II:MoOx (4:2) |

*1 PCCP:4,6mCzP2Pm:[Ir(mpptz-diBuCNp)$_3$] (0.6:0.4:0.125)
*2 PCCP:4,6mCzP2Pm:[Ir(mpptz-diBuCNp)$_3$] (0.2:0.8:0.125)

Light-emitting Elements 4 and 4-1 were each sealed using a glass substrate in a glove box containing a nitrogen atmosphere so as not to be exposed to the air (specifically, a sealant was applied to surround the element and UV treatment and heat treatment at 80° C. for 1 hour were performed at the time of sealing). Then, the initial characteristics of Light-emitting Elements 4 and 4-1 were measured. Note that the measurement was carried out in an atmosphere kept at 25° C.

Figure 32:
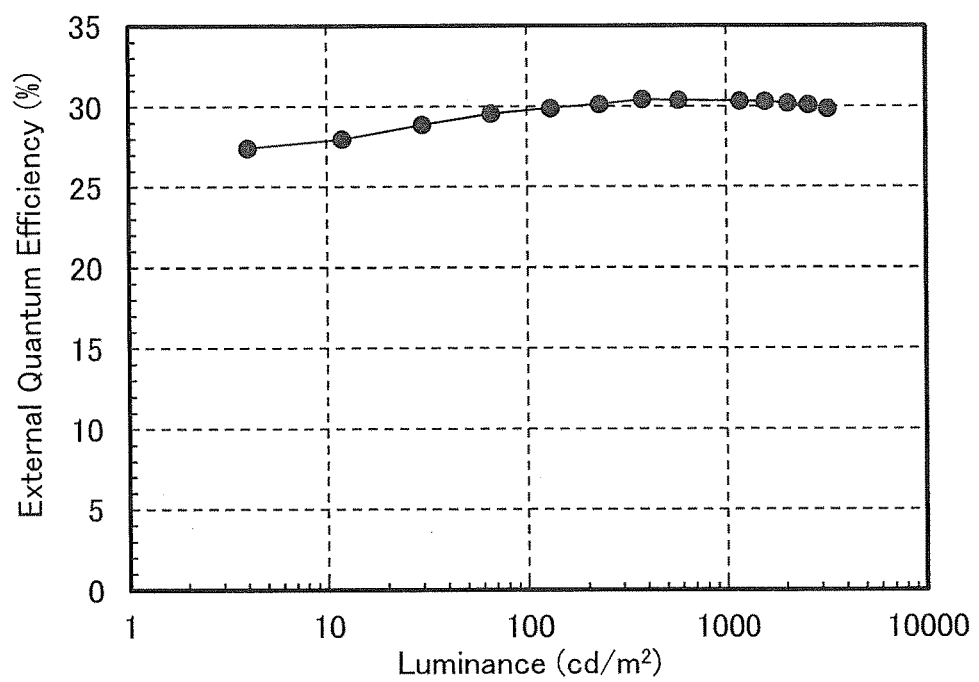
FIG. 32 shows the external quantum efficiency-luminance characteristics of Light-emitting Element 4.

FIG. 32 shows the external quantum efficiency-luminance characteristics of Light-emitting Element 4. Table 8 shows the main characteristics of Light-emitting Elements 4 and 4-1 at a luminance of about 1000 cd/m$^2$.

TABLE 8

| | Voltage (V) | Current (mA) | Current density (mA/cm$^2$) | chromaticity | | Current Efficiency (cd/A) | External Quantum Efficiency (%) |
|---|---|---|---|---|---|---|---|
| | | | | x | y | | |
| Element 4 | 3.2 | 0.03 | 0.7 | 0.21 | 0.53 | 84 | 30 |
| Element 4-1 | 4.4 | 0.52 | 13 | 0.33 | 0.45 | 7.7 | 3.0 |

As shown in Table 8, Light-emitting Element 4 has a very high efficiency, e.g., an external quantum efficiency of 30%. The light-emitting material used in Light-emitting Element 4, [Ir(mpptz-diBuCNp)$_3$], has an emission quantum yield ($\phi$) of 0.93. Assuming that the carrier balance ($\gamma$) is 1 and the proportion of generated excitons ($\alpha$) is 1, the light extraction efficiency ($\chi$) is calculated to 32.3%, which is much higher than a general theoretical light extraction efficiency of 20% to 30%.

Light-emitting Element 4-1 includes the layer for adjusting the thickness in addition to the components of Light-emitting Element 4. By adjusting the optical path length, light that travels in the front direction is attenuated, so that a representing the orientation state can be easily obtained. A difference between the structure and the fabrication method of Light-emitting Element 4 and those of Light-emitting Element 4-1 lies only in the layer for adjusting the thickness;

thus, the orientation states of light-emitting substances in the light-emitting layers are assumed to be the same.

The orientation state of a light-emitting material in the light-emitting layer was examined with the use of Light-emitting Element 4-1. The method is the same as those in Examples 1 and 2 and its description is thus omitted.

Figure 33:
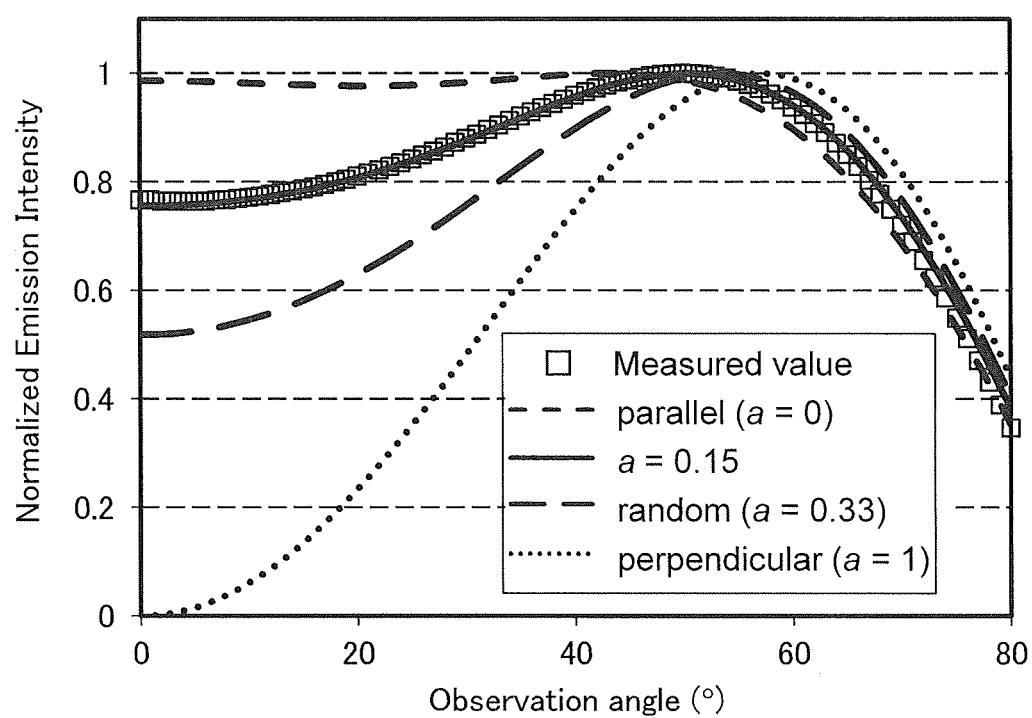
FIG. 33 is a graph showing the measured and calculated integrated intensity of the EL emission spectrum depending on the angle (θ) of the detector of Light-emitting Element 4-1.

FIG. 33 is a graph in which the vertical axis represents the integrated intensity of the EL emission spectrum from 350 nm to 810 nm depending on the angle (θ) and the horizontal axis represents the angle (θ) of the detector. In FIG. 33, a curve plotted by open squares represents the measured values, and a solid curve and a dashed curve represent the calculation results obtained by setfos which is an organic device simulator. The calculation was performed by inputting the thickness of each layer in the element, the measured values of the refractive index and the extinction efficiency, the measured value of the emission spectrum of a dopant, the position and the width of a light-emitting region, and the orientation parameter a. Among them, the thickness of each layer, the refractive index, and the extinction efficiency were measured with the use of a spectroscopic ellipsometer (M-2000U, produced by J.A. Woollam Japan Corp.). For the measurement, a film was used which was formed of the light-emitting material over a quartz substrate by a vacuum evaporation method to a thickness of 150 nm. The emission spectrum of the dopant was measured using a fluorescence spectrophotometer (FS920, produced by Hamamatsu Photonics K.K.). For the measurement, a film was used which was formed by co-evaporation of PCCP, 4,6mCzP2Pm, and [Ir(mpptz-diBuCNp)$_3$] at a weight ratio of 0.6:0.4:0.125 (=PCCP: 4,6mCzP2Pm: Ir(mpptz-diBuCNp)$_3$) over a quartz substrate to a thickness of 15 nm. In the calculation by setfos, further, the light-emitting region was set. The light-emitting region was assumed to spread such that the recombination probability was attenuated in accordance with the Gaussian distribution with a point which is approximately 20 nm from the interface between the hole-transport layer and the light-emitting layer as a top, specifically, the distance between inflection points of an assumed Gaussian function was 30 nm. Thus, the angle dependence of the integrated intensity of the emission spectrum corresponding to each parameter a can be calculated. In Light-emitting Element 4-1, the measured value well fitted a curve of a=0.15.

Figure 34:
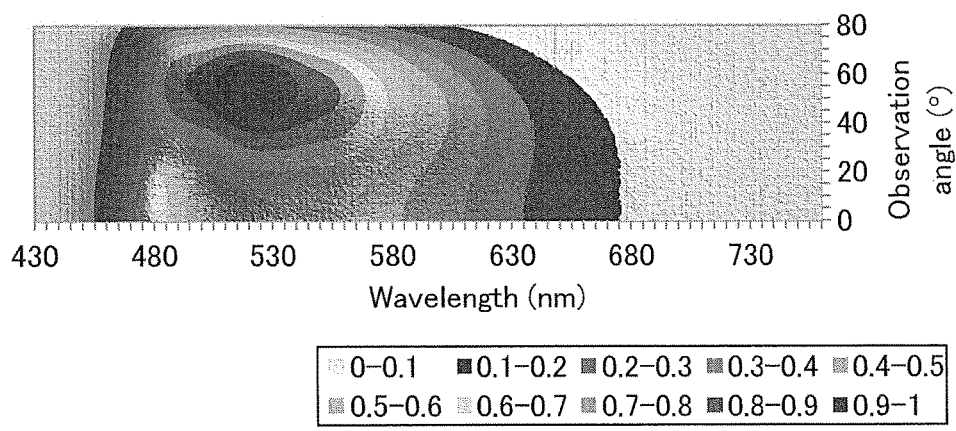
FIG. 34 is a 2D contour map showing the measured angle dependence of the EL emission spectrum of Light-emitting Element 4-1.
Figure 35:
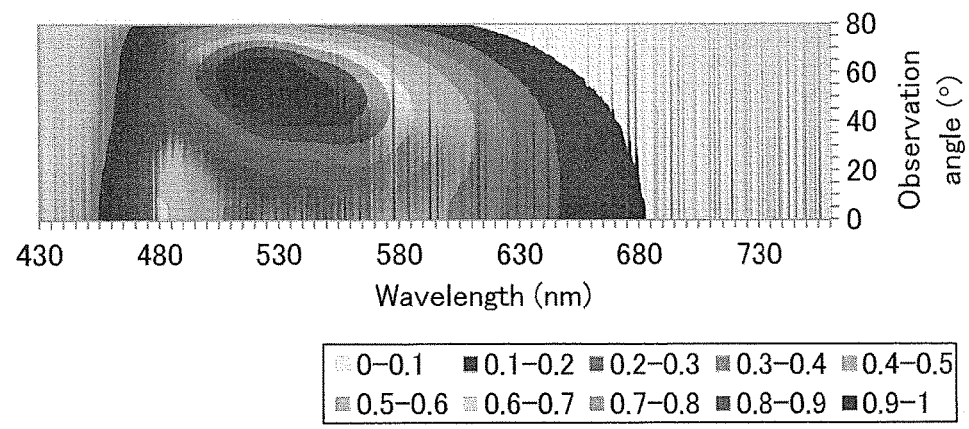
FIG. 35 is a 2D contour map obtained by calculation of Light-emitting Element 4-1.

FIG. 34 is a 2D contour map obtained by measuring the angle dependence of the EL emission spectrum of Light-emitting Element 4-1. FIG. 35 is a 2D contour map obtained by calculation. FIG. 34 and FIG. 35 show that these 2D contour maps match well. This indicates that the orientation of the light-emitting materials in Light-emitting Elements 4 and 4-1 was accurately obtained in both the experiment and the calculation.

The parameter a is ⅓≈0.33 in the case where the transition dipole is oriented in a random direction, and the parameter a is 0 in the case where the transition dipole is completely parallel to the substrate. The light extraction efficiency in the case of a=0 is 1.5 times the light extraction efficiency in the case of a=⅓≈0.33. In view of this, the light-emitting element of this example in which a=0.15 has light extraction efficiency that is 1.28 times the light extraction efficiency of the light-emitting element with a random orientation.

Light-emitting Elements 4 and 4-1 are formed using the same material for their light-emitting layers by the same method; thus, it can be said that, thanks to [Ir(mpptz-diBuCNp)$_3$] in the light-emitting layer, Light-emitting Element 4 has, like Light-emitting Element 4-1, an orientation of a=0.15. Light-emitting Element 4 has a very high external quantum efficiency of 30%. It is found that a light-emitting element with high emission efficiency can be obtained by setting a to less than or equal to 0.2.

The quantum yield of the film was 80% on average in the case of excitation light at 350 nm; the film was formed by co-evaporation of PCCP, 4,6mCzP2Pm, and [Ir(mpptz-diBuCNp)$_3$] at a weight ratio of 0.6:0.4:0.125 (=PCCP: 4,6mCzP2Pm: [Ir(mpptz-diBuCNp)$_3$]) to a thickness of 50 nm. That is, the light-emitting layer of this example has a parameter a of 0.2 or less and a phosphorescent quantum yield of 80% or higher; thus, this layer satisfies theoretical conditions under which the external quantum efficiency can be higher than or equal to 30%.

Example 5

In this example, results of calculating the parameter a of a light-emitting element (Light-emitting Element 5) of one embodiment of the present invention with high efficiency are described in detail. For the above purpose, a light-emitting element (Light-emitting Element 5-1) for measurement which includes a light-emitting layer having the same structure as that of Light-emitting Element 5 and in which the luminance in the front direction is reduced as much as possible was also fabricated.

First, a fabrication method and the structure of the light-emitting element of one embodiment of the present invention are described. Organic compounds used in the light-emitting element of one embodiment of the present invention are given below.

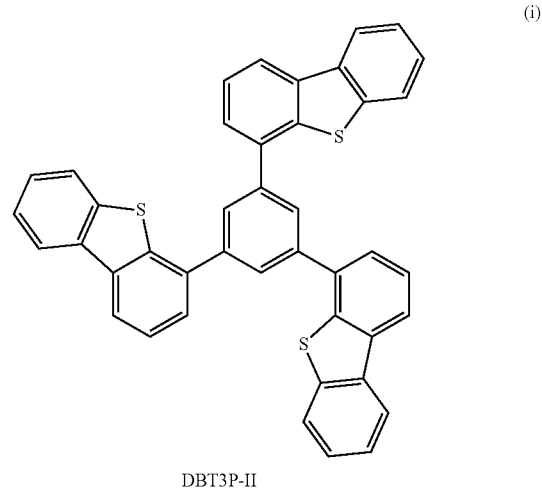

DBT3P-II

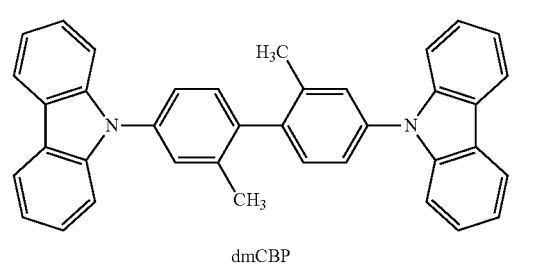

dmCBP

-continued

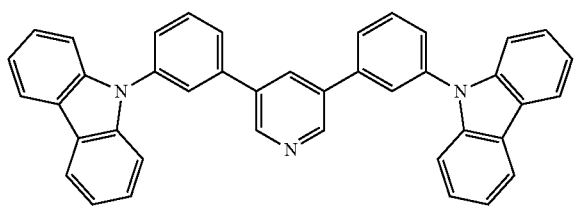

3,5DCzPPy

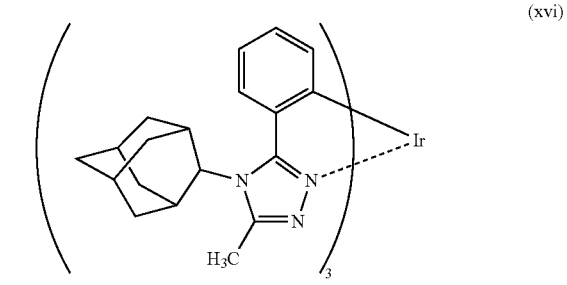

[Ir(Mptz-Adm2)₃]

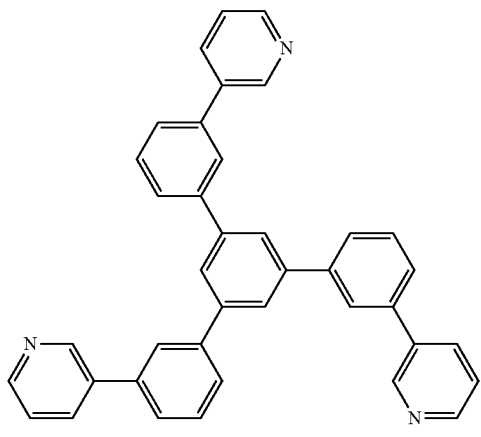

TmPyPB

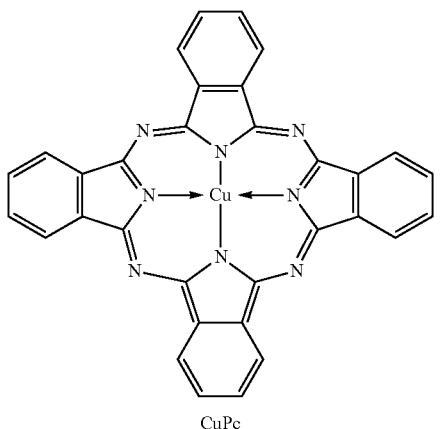

CuPc (Fabrication Method of Light-Emitting Element 5)

First, a film of indium tin oxide containing silicon oxide (ITSO) was formed over a glass substrate by a sputtering method, so that the first electrode 101 was formed. The thickness of the first electrode 101 was 70 nm and the electrode area was 2 mm×2 mm.

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 4,4',4"-(benzene-1,3,5-triyl)tri(dibenzothiophene) (abbreviation: DBT3P-II) represented by Structural Formula (i) and molybdenum(VI) oxide were deposited by co-evaporation to a thickness of 20 nm at a weight ratio of 2:1 (=DBT3P-II: molybdenum oxide) by an evaporation method using resistance heating, so that the hole-injection layer 111 was formed.

Next, 4,4'-bis(9-carbazole)-2,2'-dimethylbiphenyl (abbreviation: dmCBP) represented by Structural Formula (xiv) was deposited by evaporation to a thickness of 20 nm on the hole-injection layer 111 to form the hole-transport layer 112.

Then, 3,5-bis[3-(9H-carbazol-9-yl)phenyl]pyridine (abbreviation: 35DCzPPy) represented by Structural Formula (xv) and tris{2-[4-(2-adamantyl)-3-methyl-4H-1,2,4-triazol-5-yl-N]phenyl-κC}iridium(III) (abbreviation: [Ir(Mptz-Adm2)₃]) represented by Structural Formula (xvi) were deposited by co-evaporation to a thickness of 30 nm at a weight ratio of 1:0.06 (=35DCzPPy: [Ir(Mptz-Adm2)₃]), whereby the light-emitting layer 113 was formed.

After that, on the light-emitting layer 113, 1,3,5-tris[3-(3-pyridyl)phenyl]benzene (abbreviation: TmPyPB) represented by Structural Formula (xvii) was deposited by evaporation to a thickness of 25 nm to form the electron-transport layer 114.

After the formation of the electron-transport layer 114, lithium oxide (Li₂O) was deposited by evaporation to a thickness of 0.1 nm to form the electron-injection layer 115. Then, aluminum was deposited by evaporation to a thickness of 200 nm to form the second electrode 102. Through the above-described steps, Light-emitting Element 5 of this example was fabricated.

(Fabrication Method of Light-Emitting Element 5-1)

Light-emitting element 5-1 was fabricated in the following manner. After the electron-injection layer 115 of Light-emitting Element 5 was formed, copper phthalocyanine (abbreviation: CuPc) represented by Structural Formula (vi) was deposited by evaporation to a thickness of 2 nm, and then, DBT3P-II and molybdenum(VI) oxide were deposited by co-evaporation at a weight ratio of 2:1 (=DBT3P-II: molybdenum oxide) to a thickness of 60 nm. In such a manner, a layer for adjusting the thickness was formed.

The element structures of Light-emitting Elements 5 and 5-1 are shown in the following table.

TABLE 9

| | hole-injection layer | hole-transport layer | light-emitting layer | electron-transport layer | electron-injection layer | layer for adjusting the thickness | |
|---|---|---|---|---|---|---|---|
| | 20 nm | 20 nm | 30 nm | 25 nm | 0.1 nm | 2 nm | 60 nm |
| Element 5 | DBT3P-II:MoOx (4:2) | dmCBP | 35DCzPPy: [Ir(Mptz-Adm2)₃] (1:0.06) | TmPyPB | Li₂O | — | — |
| Element 5-1 | | | | | | CuPc | DBT3P-II:MoOx (4:2) |

Light-emitting elements 5 and 5-1 were each sealed using a glass substrate in a glove box containing a nitrogen atmosphere so as not to be exposed to the air (specifically, a sealant was applied to surround the element and UV treatment and heat treatment at 80° C. for 1 hour were performed at the time of sealing). Then, the initial characteristics of Light-emitting Elements 5 and 5-1 were measured. Note that the measurement was carried out in an atmosphere kept at 25° C.

Figure 36:
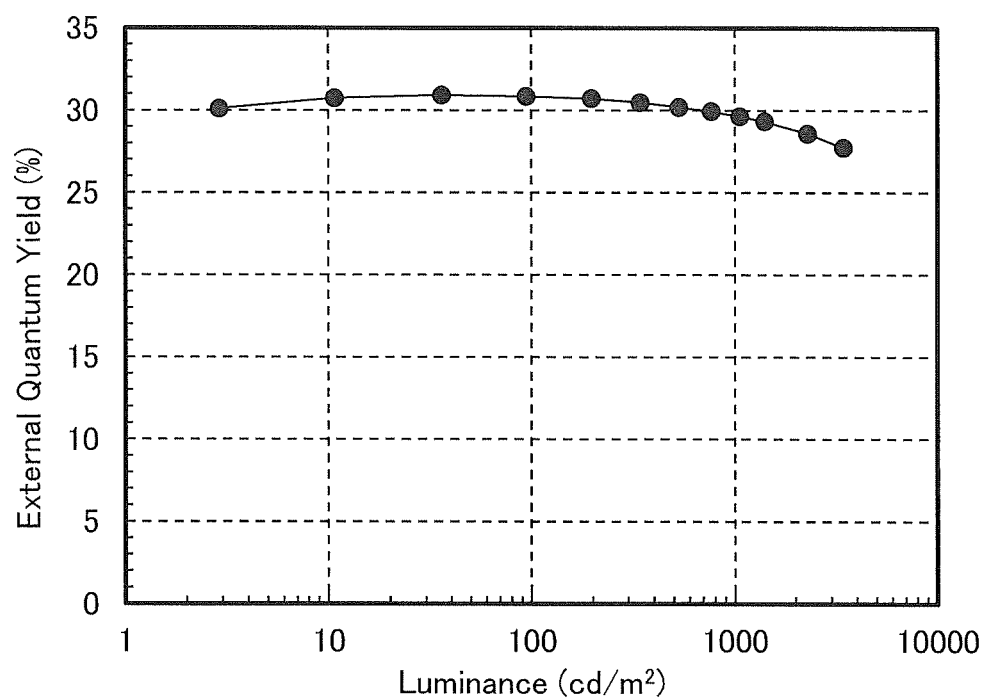
FIG. 36 shows the external quantum efficiency-luminance characteristics of Light-emitting Element 5.

FIG. 36 shows the external quantum efficiency-luminance characteristics of Light-emitting Element 5. Table 10 shows the main characteristics of Light-emitting Elements 5 and 5-1 at a luminance of about 1000 cd/m².

TABLE 10

| | Voltage (V) | Current (mA) | Current density (mA/cm²) | chromaticity x | chromaticity y | Current Efficiency (cd/A) | External Quantum Efficiency (%) |
|---|---|---|---|---|---|---|---|
| Element 5 | 3.9 | 0.10 | 2.5 | 0.15 | 0.19 | 42 | 25 |
| Element 5-1 | 6.2 | 0.68 | 17 | 0.32 | 0.48 | 6.1 | 2.0 |

As shown in Table 10, Light-emitting Element 5 has a very high efficiency, e.g., an external quantum efficiency of 25%. The light-emitting material used in Light-emitting Element 5, [Ir(Mptz-Adm2)₃], has an emission quantum yield ($\phi$) of 0.94. Assuming that the carrier balance ($\gamma$) is 1 and the proportion of generated excitons ($\alpha$) is 1, the light extraction efficiency ($\chi$) is calculated to 26.6%.

Light-emitting Element 5-1 includes the layer for adjusting the thickness in addition to the components of Light-emitting Element 5. By adjusting the optical path length, light that travels in the front direction is attenuated, so that a representing the orientation state can be easily obtained. A difference between the structure and the fabrication method of Light-emitting Element 5 and those of Light-emitting Element 5-1 lies only in the layer for adjusting the thickness; thus, the orientation states of light-emitting substances in the light-emitting layers are assumed to be the same.

The orientation state of a light-emitting material in the light-emitting layer was examined with the use of Light-emitting Element 5-1. First, the angle dependence of the shape of the EL emission spectrum was measured by measuring the EL spectrum in steps of 10° in such a manner that, as shown in FIG. 20, the substrate provided with Light-emitting Element 5-1 was inclined to a detector (a photonic multichannel analyzer PMA-12, produced by Hamamatsu Photonics K.K.) from θ=0° to 80°. In this measurement, a linear polarizer (Glan-Taylor prism) was disposed between Light-emitting Element 5-1 and the detector to be perpendicular to the substrate surface in order to remove an S polarization from light emitted from Light-emitting Element 5-1, so that the spectrum of only a P polarization was measured.

Figure 37:
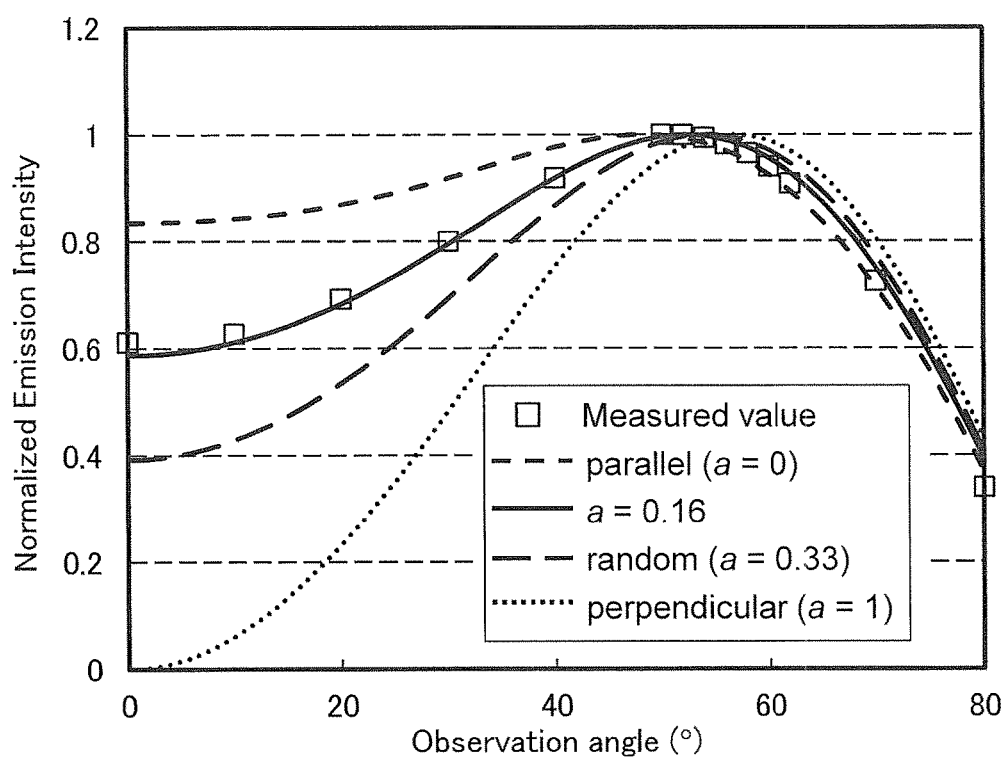
FIG. 37 is a graph showing the measured and calculated integrated intensity of the EL emission spectrum depending on the angle (θ) of the detector of Light-emitting Element 5-1.

FIG. 37 is a graph in which the vertical axis represents the integrated intensity of the EL emission spectrum from 400 nm to 800 nm depending on the angle (θ) and the horizontal axis represents the angle (θ) of the detector. In FIG. 37, a curve plotted by open squares represents the measured values, and a solid curve and a dashed curve represent the calculation results obtained by setfos which is an organic device simulator. The calculation was performed by inputting the thickness of each layer in the element, the measured values of the refractive index and the extinction efficiency, the measured value of the emission spectrum of a dopant, the position and the width of a light-emitting region, and the orientation parameter a. Among them, the thickness of each layer, the refractive index, and the extinction efficiency were measured with the use of a spectroscopic ellipsometer (M-2000U, produced by J.A. Woollam Japan Corp.). For the measurement, a film was used which was formed of the light-emitting material over a quartz substrate by a vacuum evaporation method to a thickness of 150 nm. The emission spectrum of the dopant was measured using a fluorescence spectrophotometer (FS920, produced by Hamamatsu Photonics K.K.). For the measurement, a film was used which was formed by co-evaporation of 35DCzPPy and [Ir(Mptz-Adm2)₃] using a vacuum evaporation method at a weight ratio of 1:0.06 (=35DCzPPy: [Ir(Mptz-Adm2)₃]) over a quartz substrate to a thickness of 50 nm. In the calculation by setfos, further, the light-emitting region was set. The light-emitting region was assumed to spread such that the recombination probability was attenuated exponentially in the cathode direction with the interface between the hole-transport layer and the light-emitting layer as a top, specifically, the recombination probability was attenuated to 1/e at a thickness of 5 nm. Thus, the angle dependence of the integrated intensity of the emission spectrum corresponding to each parameter a can be calculated. In Light-emitting Element 5-1, the measured value well fitted a curve of a=0.16.

The parameter a is ⅓≈0.33 in the case where the transition dipole is oriented in a random direction, and the parameter a is 0 in the case where the transition dipole is completely parallel to the substrate. The light extraction efficiency in the case of a=0 is 1.5 times the light extraction efficiency in the case of a=⅓≈0.33. In view of this, the light-emitting element of this example in which a=0.16 has light extraction efficiency that is 1.26 times the light extraction efficiency of the light-emitting element with a random orientation.

Light-emitting Elements 5 and 5-1 are formed using the same material for their light-emitting layers by the same method; thus, it can be said that, thanks to [Ir(Mptz-Adm2)$_3$] in the light-emitting layer, Light-emitting Element 5 has, like Light-emitting Element 5-1, an orientation of a=0.16. Light-emitting Element 5 has a very high external quantum efficiency of 25%. It is found that a light-emitting element with high emission efficiency can be obtained by setting a to less than or equal to 0.2.

Example 6

In this example, results of calculating the parameter a of a light-emitting element (Light-emitting Element 6) of one embodiment of the present invention with high efficiency are described in detail. For the above purpose, a light-emitting element (Light-emitting Element 6-1) for measurement which includes a light-emitting layer having the same structure as that of Light-emitting Element 6 and in which the luminance in the front direction is reduced as much as possible was also fabricated. FIG. 18 illustrates the structure of the light-emitting element.

First, a fabrication method and the structure of the light-emitting element of one embodiment of the present invention are described. Organic compounds used in the light-emitting element of one embodiment of the present invention are given below.

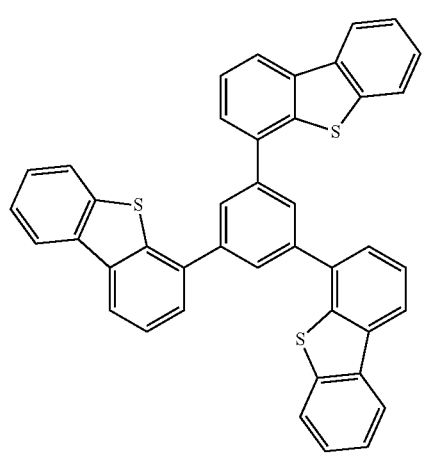

DBT3P-II (i)

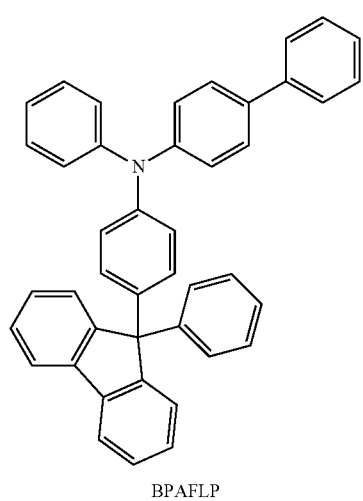

BPAFLP (ii)

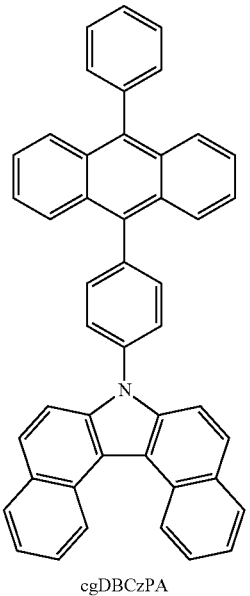

cgDBCzPA (iii)

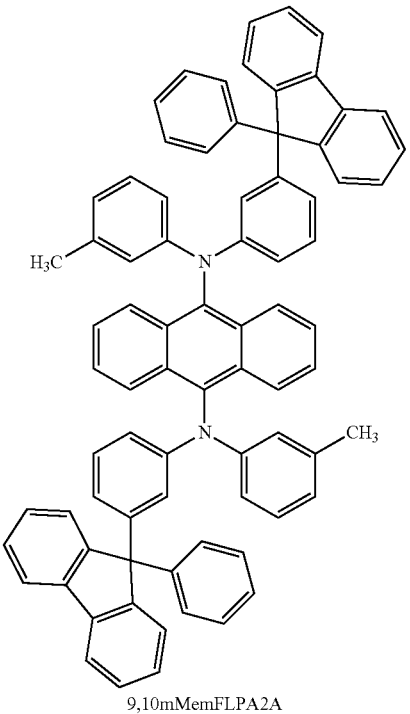

9,10mMemFLPA2A (xviii)

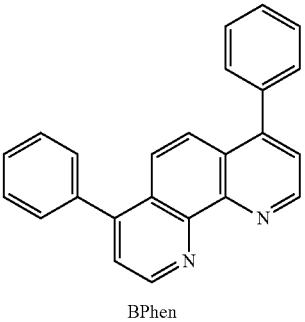

BPhen (v)

-continued

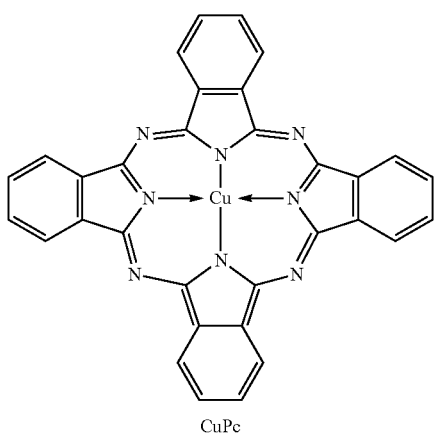

CuPc (vi)

(Fabrication Method of Light-Emitting Element 6)

First, a film of indium tin oxide containing silicon oxide (ITSO) was formed over a glass substrate by a sputtering method, so that the first electrode 101 was formed. The thickness of the first electrode 101 was 70 nm and the electrode area was 2 mm×2 mm.

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 4,4',4''-(benzene-1,3,5-triyl)tri(dibenzothiophene) (abbreviation: DBT3P-II) represented by Structural Formula (i) and molybdenum(VI) oxide were deposited by co-evaporation to a thickness of 40 nm at a weight ratio of 4:2 (=DBT3P-II: molybdenum oxide) by an evaporation method using resistance heating, so that the hole-injection layer 111 was formed.

Next, 4-phenyl-4'-(9-phenylfluoren-9-yl)triphenylamine (abbreviation: BPAFLP) represented by Structural Formula (ii) was deposited by evaporation to a thickness of 30 nm on the hole-injection layer 111 to form the hole-transport layer 112.

Next, the light-emitting layer 113 was formed by co-evaporation of 7-[4-(10-phenyl-9-anthryl)phenyl]-7H-dibenzo[c,g]carbazole (abbreviation: cgDBCzPA) represented by Structural Formula (iii) and N,N'-bis(3-methylphenyl)-N,N'-bis[3-(9-phenyl-9H-fluoren-9-yl)phenyl]-anthracene-9,10-diamine (abbreviation: 9,10mMemFLPA2A) represented by Structural Formula (xviii) at a weight ratio of 1:0.1 (=cgDBCzPA: 9,10mMemFLPA2A) to a thickness of 35 nm.

Then, on the light-emitting layer 113, bathophenanthroline (abbreviation: BPhen) represented by Structural Formula (v) was deposited by evaporation to a thickness of 15 nm to form the electron-transport layer 114.

After the formation of the electron-transport layer 114, lithium oxide ($Li_2O$) was deposited by evaporation to a thickness of 0.1 nm to form the electron-injection layer 115. Then, aluminum was deposited by evaporation to a thickness of 200 nm to form the second electrode 102. Through the above-described steps, Light-emitting Element 6 of this example was fabricated.

(Fabrication Method of Light-Emitting Element 6-1)

Light-emitting element 6-1 was fabricated in the following manner. After the electron-injection layer 115 of Light-emitting Element 6 was formed, copper phthalocyanine (abbreviation: CuPc) represented by Structural Formula (vi) was deposited by evaporation to a thickness of 2 nm to form the electron-relay layer 118, and then, DBT3P-II and molybdenum(VI) oxide were deposited by co-evaporation at a weight ratio of 2:1 (=DBT3P-II: molybdenum oxide) to a thickness of 80 nm to form the p-type layer 117. In such a manner, a layer for adjusting the thickness was formed.

The element structures of Light-emitting Elements 6 and 6-1 are shown in the following table.

TABLE 11

| | hole-injection layer | hole-transport layer | light-emitting layer | electron-transport layer | electron-injection layer | layer for adjusting the thickness | |
|---|---|---|---|---|---|---|---|
| | 40 nm | 30 nm | 35 nm | 15 nm | 0.1 nm | 2 nm | 80 nm |
| Element 6 | DBT3P-II:MoOx (4:2) | BPAFLP | cgDBCzPA: 9,10mMemFLPA2A (1:0.1) | BPhen | $Li_2O$ | — | — |
| Element 6-1 | | | | | | CuPc | DBT3P-II:MoOx (4:2) |

Light-emitting Elements 6 and 6-1 were each sealed using a glass substrate in a glove box containing a nitrogen atmosphere so as not to be exposed to the air (specifically, a sealant was applied to surround the element and UV treatment and heat treatment at 80° C. for 1 hour were performed at the time of sealing). Then, the initial characteristics of Light-emitting Elements 6 and 6-1 were measured. Note that the measurement was carried out in an atmosphere kept at 25° C.

Figure 38:
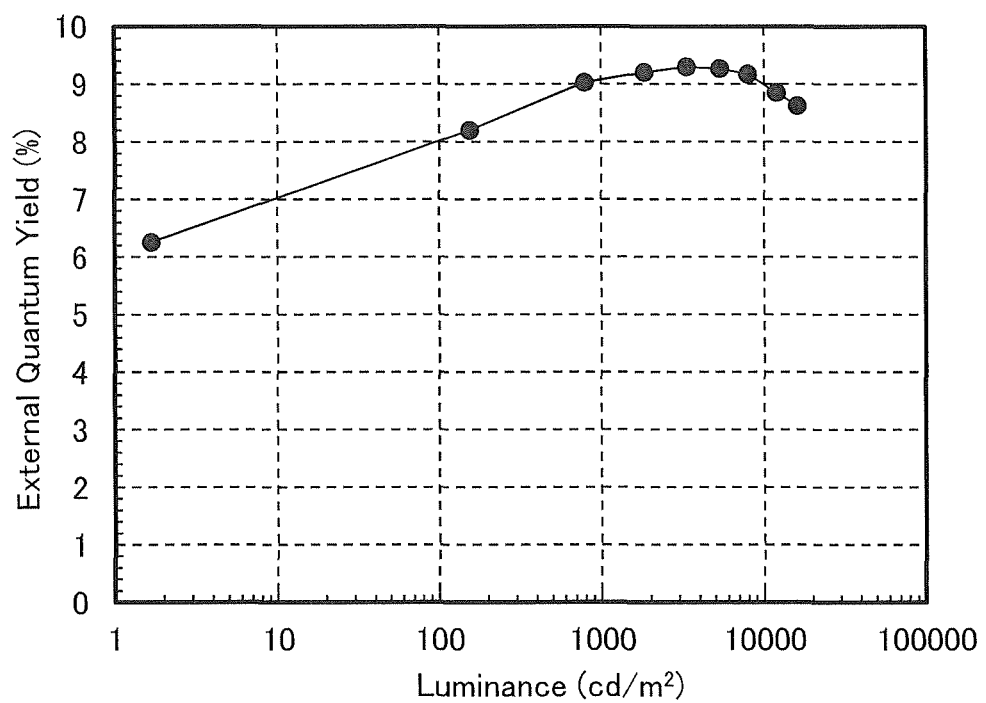
FIG. 38 shows the external quantum efficiency-luminance characteristics of Light-emitting Element 6.

FIG. 38 shows the external quantum efficiency-luminance characteristics of Light-emitting Element 6. Table 12 shows the main characteristics of Light-emitting Elements 6 and 6-1 at a luminance of about 1000 cd/m².

TABLE 12

|  | Voltage (V) | Current (mA) | Current density (mA/cm$^2$) | chromaticity x | y | Current Efficiency (cd/A) | External Quantum Efficiency (%) |
|---|---|---|---|---|---|---|---|
| Element 6 | 3.0 | 0.09 | 2.4 | 0.29 | 0.65 | 34 | 8.3 |
| Element 6-1 | 4.8 | 3.40 | 85 | 0.33 | 0.46 | 1.2 | 0.5 |

As shown in Table 12, Light-emitting Element 6 has a very high efficiency, e.g., an external quantum efficiency of 8.3%. The light-emitting material used in Light-emitting Element 6, 9,10mMemFLPA2A, has an emission quantum yield (φ) of 0.90. Assuming that the carrier balance (γ) is 1 and the proportion of generated excitons (α) is 0.25, the light extraction efficiency (χ) is calculated to 36.9%, which is much higher than a general theoretical light extraction efficiency of 20% to 30%.

Light-emitting Element 6-1 includes the layer for adjusting the thickness in addition to the components of Light-emitting Element 6. By adjusting the optical path length, light that travels in the front direction is attenuated, so that a representing the orientation state can be easily obtained. A difference between the structure and the fabrication method of Light-emitting Element 6 and those of Light-emitting Element 6-1 lies only in the layer for adjusting the thickness; thus, the orientation states of light-emitting substances in the light-emitting layers are assumed to be the same.

The orientation state of a light-emitting material in the light-emitting layer was examined with the use of Light-emitting Element 6-1. First, the angle dependence of the shape of the EL emission spectrum was measured by measuring the EL spectrum in steps of 1° in such a manner that, as shown in FIG. 20, the substrate provided with Light-emitting Element 6-1 was inclined to a detector (a photonic multichannel analyzer PMA-12, produced by Hamamatsu Photonics K.K.) from θ=0° to 80°. In this measurement, a linear polarizer (Glan-Taylor prism) was disposed between Light-emitting Element 6-1 and the detector to be perpendicular to the substrate surface in order to remove an S polarization from light emitted from Light-emitting Element 6-1, so that the spectrum of only a P polarization was measured.

Figure 39:
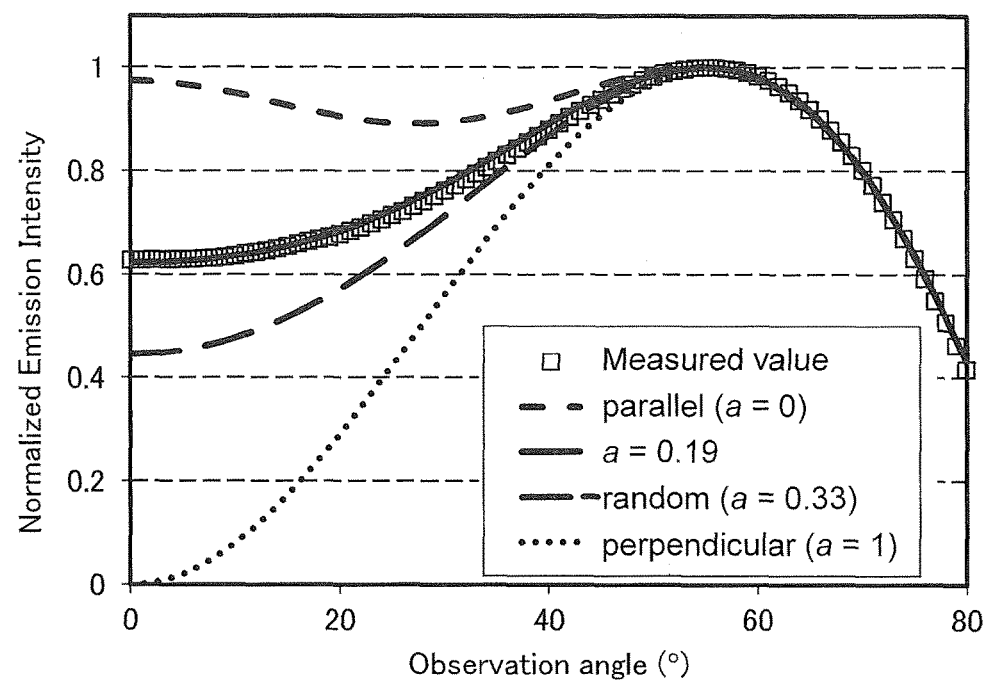
FIG. 39 is a graph showing the measured and calculated integrated intensity of the EL emission spectrum depending on the angle (θ) of the detector of Light-emitting Element 6-1.

FIG. 39 is a graph in which the vertical axis represents the integrated intensity of the EL emission spectrum from 470 nm to 750 nm depending on the angle (θ) and the horizontal axis represents the angle (θ) of the detector. In FIG. 39, a curve plotted by open squares represents the measured values, and a solid curve and a dashed curve represent the calculation results obtained by setfos which is an organic device simulator. The calculation was performed by inputting the thickness of each layer in the element, the measured values of the refractive index and the extinction efficiency, the measured value of the emission spectrum of a dopant, the position and the width of a light-emitting region, and the orientation parameter a. Among them, the thickness of each layer, the refractive index, and the extinction efficiency were measured with the use of a spectroscopic ellipsometer (M-2000U, produced by J.A. Woollam Japan Corp.). For the measurement, a film was used which was formed of the light-emitting material over a quartz substrate by a vacuum evaporation method to a thickness of 150 nm. The emission spectrum of the dopant was measured using a fluorescence spectrophotometer (FS920, produced by Hamamatsu Photonics K.K.). For the measurement, a film was used which was formed by co-evaporation of cgDBCzPA and 9,10mMemFLPA2A using a vacuum evaporation method at a weight ratio of 1:0.1 (=cgDBCzPA: 9,10mMemFLPA2A) over a quartz substrate to a thickness of 50 nm. In the calculation by setfos, further, the light-emitting region was set. The light-emitting region was assumed to spread such that the recombination probability was attenuated in accordance with the Gaussian distribution with a point which is approximately 33 nm from the interface between the hole-transport layer and the light-emitting layer as a top, specifically, the distance between inflection points of an assumed Gaussian function was 12.5 nm. Thus, the angle dependence of the integrated intensity of the emission spectrum corresponding to each parameter a can be calculated. In Light-emitting Element 6-1, the measured value well fitted a curve of a=0.19.

Figure 40:
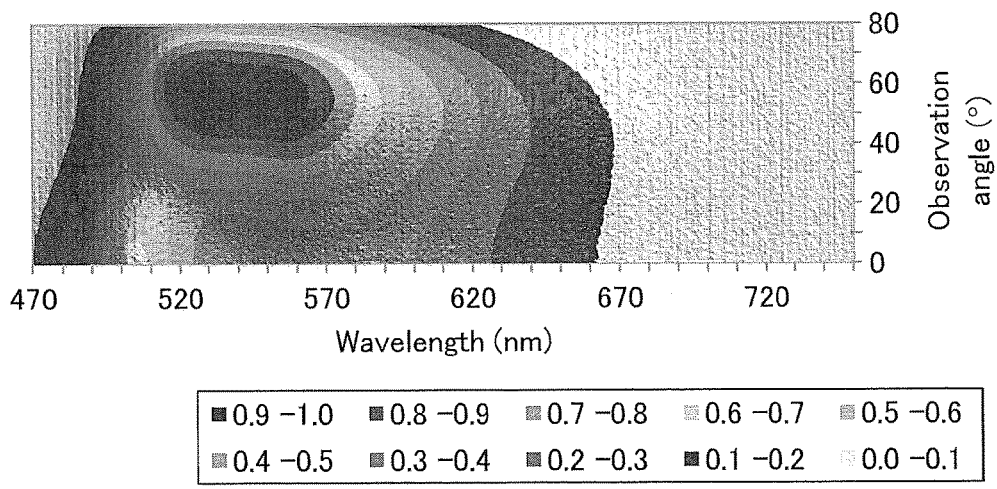
FIG. 40 is a 2D contour map showing the measured angle dependence of the EL emission spectrum of Light-emitting Element 6-1.
Figure 41:
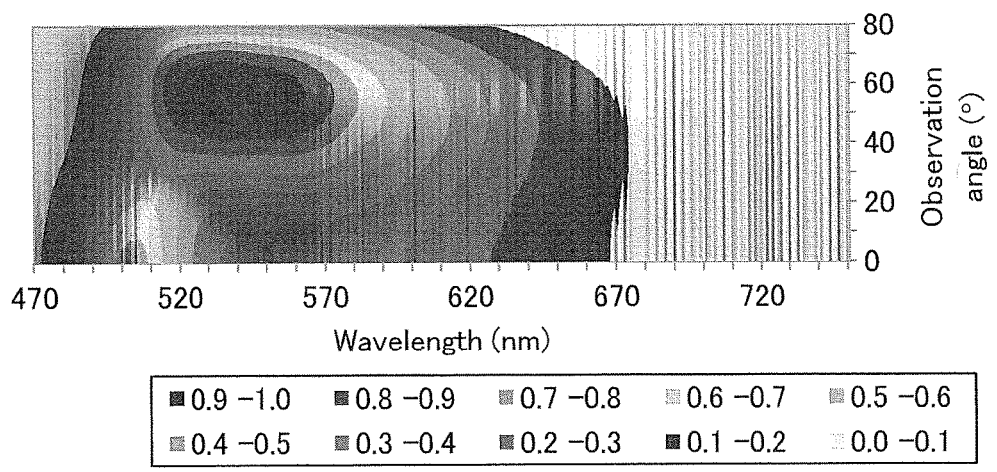
FIG. 41 is a 2D contour map obtained by calculation of Light-emitting Element 6-1.

FIG. 40 is a 2D contour map obtained by measuring the angle dependence of the EL emission spectrum of Light-emitting Element 6-1. FIG. 41 is a 2D contour map obtained by calculation. FIG. 40 and FIG. 41 show that these 2D contour maps match well. This indicates that the orientation of the light-emitting materials in Light-emitting Elements 6 and 6-1 was accurately obtained in both the experiment and the calculation.

The parameter a is ⅓≈0.33 in the case where the transition dipole is oriented in a random direction, and the parameter a is 0 in the case where the transition dipole is completely parallel to the substrate. The light extraction efficiency in the case of a=0 is 1.5 times the light extraction efficiency in the case of a=⅓≈0.33. In view of this, the light-emitting element of this example in which a=0.19 has light extraction efficiency that is 1.22 times the light extraction efficiency of the light-emitting element with a random orientation. That is, the light-emitting element of one embodiment of the present invention has an emission efficiency that is 1.22 times the emission efficiency of the light-emitting element with a random orientation.

Light-emitting Elements 6 and 6-1 are formed using the same material for their light-emitting layers by the same method; thus, it can be said that Light-emitting Element 6 has, like Light-emitting Element 6-1, an orientation of a=0.19. Light-emitting Element 6 has a very high external quantum efficiency of 8.3%. It is found that a light-emitting element with high emission efficiency can be obtained by setting a to less than or equal to 0.2.

Example 7

In this example, results of calculating the parameter a of a light-emitting element (Light-emitting Element 7) of one embodiment of the present invention with high efficiency are described in detail. For the above purpose, a light-emitting element (Light-emitting Element 7-1) for measurement which includes a light-emitting layer having the same structure as that of Light-emitting Element 7 and in which the luminance in the front direction is reduced as much as possible was also fabricated. FIG. 18 illustrates the structure of the light-emitting element.

First, a fabrication method and the structure of the light-emitting element of one embodiment of the present invention are described. Organic compounds used in the light-emitting element of one embodiment of the present invention are given below.

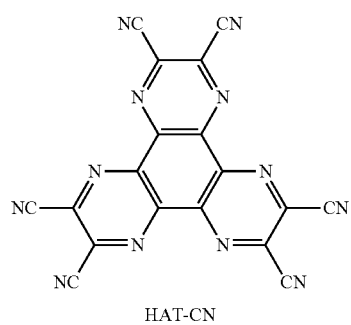

HAT-CN (xix)

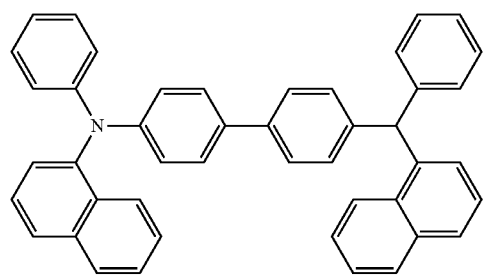

NPB (xx)

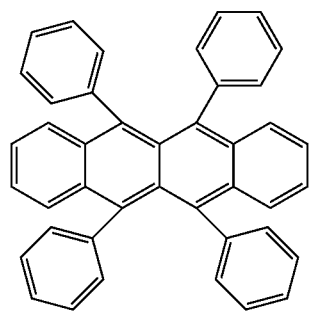

Rubrene (xxi)

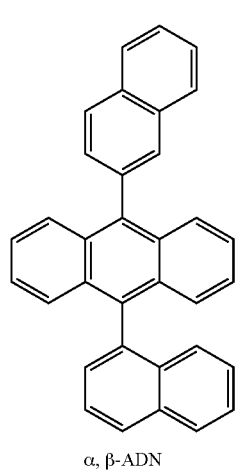

α, β-ADN (xxii)

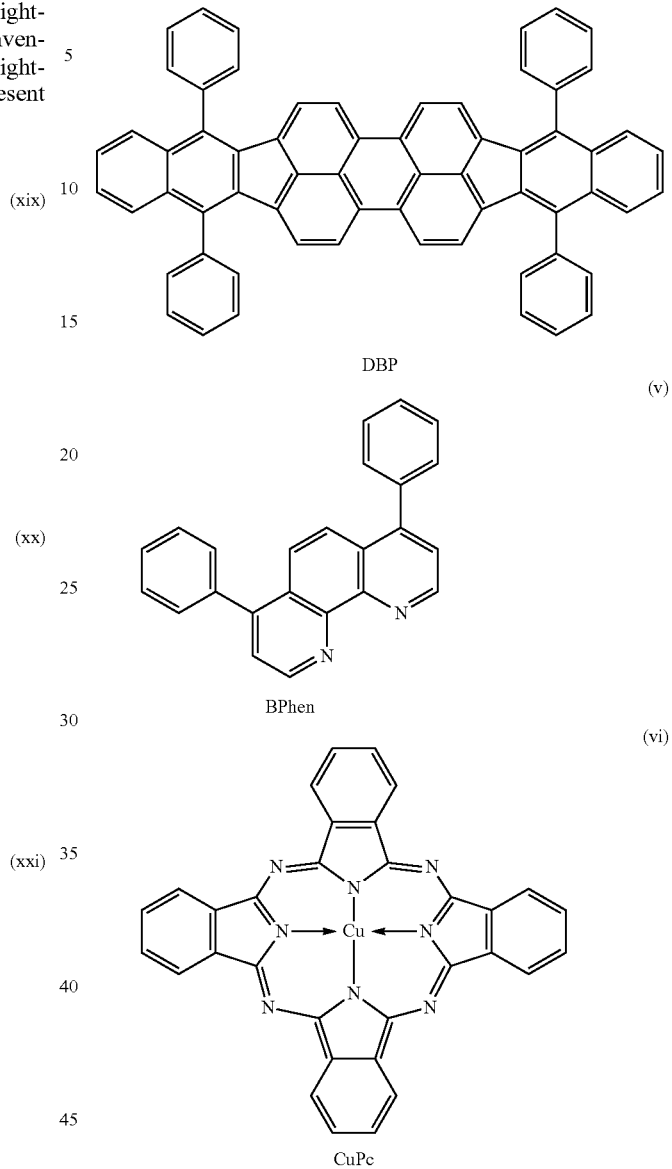

DBP (xxiii)

BPhen (v)

CuPc (vi)

(Fabrication Method of Light-Emitting Element 7)

First, a film of indium tin oxide containing silicon oxide (ITSO) was formed over a glass substrate by a sputtering method, so that the first electrode 101 was formed. The thickness of the first electrode 101 was 70 nm and the electrode area was 2 mm×2 mm.

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, 2,3,6,7,10,11-hexacyano-1,4,5,8,9,12-hexaazatriphenylene (abbreviation: HAT-CN) represented by Structural Formula (xix) was deposited by evaporation to a thickness of 10 nm on the first electrode 101 by an evaporation method using resistance heating, whereby the hole-injection layer 111 was formed.

Next, 4,4'-bis[N-(1-naphthyl)-N-phenylamino]biphenyl (abbreviation: NPB) represented by Structural Formula (xx) was deposited by evaporation to a thickness of 80 nm on the hole-injection layer 111 to form the hole-transport layer 112.

Next, the light-emitting layer 113 was formed by co-evaporation of rubrene represented by Structural Formula (xxi), 9-(1-naphthyl)-10-(2-naphthyl)anthracene (abbreviation: α,β-ADN) represented by Structural Formula (xxii), and 5,10,15,20-tetraphenylbisbenzo[5,6]indeno[1,2,3-cd:1',2',3'-lm]perylene (abbreviation: DBP) represented by Structural Formula (xxiii) at a weight ratio of 0.8:0.2:0.005 (=rubrene: α,β-ADN: DBP) to a thickness of 30 nm.

Then, on the light-emitting layer 113, bathophenanthroline (abbreviation: BPhen) represented by Structural Formula (v) was deposited by evaporation to a thickness of 20 nm to form the electron-transport layer 114.

After the formation of the electron-transport layer 114, lithium oxide ($Li_2O$) was deposited by evaporation to a thickness of 0.1 nm to form the electron-injection layer 115. Then, aluminum was deposited by evaporation to a thickness of 200 nm to form the second electrode 102. Through the above-described steps, Light-emitting Element 7 of this example was fabricated.

(Fabrication Method of Light-Emitting Element 7-1)

Light-emitting element 7-1 was fabricated in the following manner. After the electron-injection layer 115 of Light-emitting Element 7 was formed, copper phthalocyanine (abbreviation: CuPc) represented by Structural Formula (vi) was deposited by evaporation to a thickness of 2 nm to form the electron-relay layer 118, and then, DBT3P-II and molybdenum(VI) oxide were deposited by co-evaporation at a weight ratio of 2:1 (=DBT3P-II: molybdenum oxide) to a thickness of 85 nm to form the p-type layer 117. In such a manner, a layer for adjusting the thickness was formed.

The element structures of Light-emitting Elements 7 and 7-1 are shown in the following table.

Light-emitting Elements 7 and 7-1 were each sealed using a glass substrate in a glove box containing a nitrogen atmosphere so as not to be exposed to the air (specifically, a sealant was applied to surround the element and UV treatment and heat treatment at 80° C. for 1 hour were performed at the time of sealing). Then, the initial characteristics of Light-emitting Elements 7 and 7-1 were measured. Note that the measurement was carried out in an atmosphere kept at 25° C.

Figure 42:
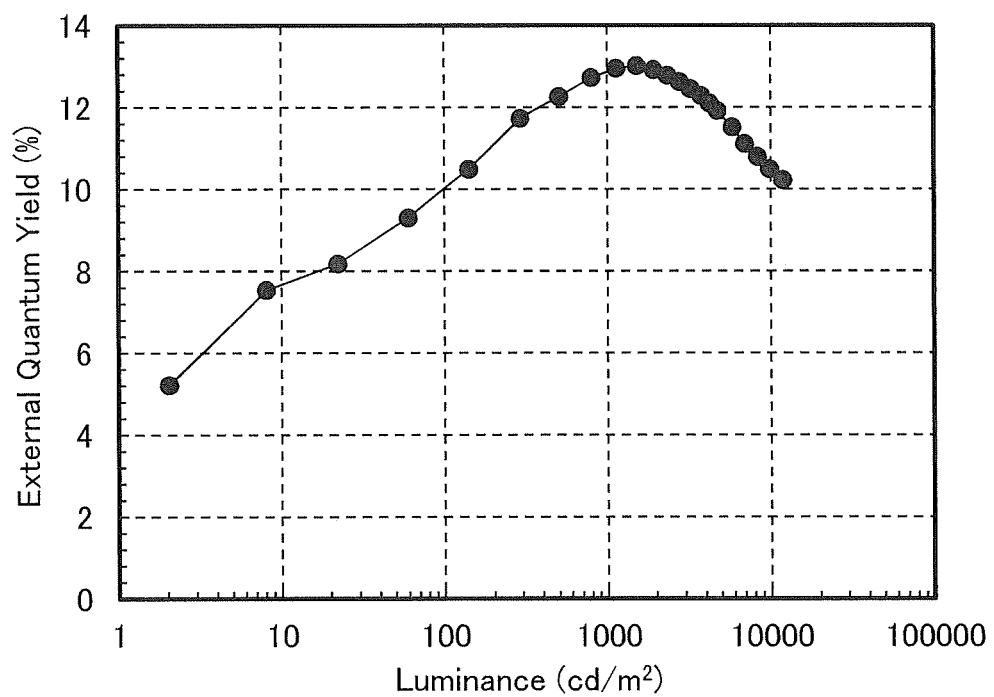
FIG. 42 shows the external quantum efficiency-luminance characteristics of Light-emitting Element 7.

FIG. 42 shows the external quantum efficiency-luminance characteristics of Light-emitting Element 7. Table 14 shows the main characteristics of Light-emitting Elements 7 and 7-1 at a luminance of about 1000 $cd/m^2$.

TABLE 14

| | Voltage (V) | Current (mA) | Current density ($mA/cm^2$) | chromaticity x | chromaticity y | Current Efficiency (cd/A) | External Quantum Efficiency (%) |
|---|---|---|---|---|---|---|---|
| Element 7 | 3.2 | 0.32 | 8.0 | 0.68 | 0.32 | 14 | 11 |
| Element 7-1 | 6.6 | 15.06 | 377 | 0.67 | 0.33 | 0.2 | 0.7 |

As shown in Table 14, Light-emitting Element 7 has a very high efficiency, e.g., an external quantum efficiency of 11%. The light-emitting material used in Light-emitting Element 7, DBP, has an emission quantum yield (φ) of 0.72. Assuming that the carrier balance (γ) is 1 and the proportion of generated excitons (α) is 0.25, the light extraction efficiency (χ) is calculated to 61.1%, which is much higher than a general theoretical light extraction efficiency of 20% to 30%. Measurement results of transient EL emission indicate that TTA also occurred in this element. The proportion of generated excitons was practically higher than 0.25 owing to TTA.

Light-emitting Element 7-1 includes the layer for adjusting the thickness in addition to the components of Light-emitting Element 7. By adjusting the optical path length, light that travels in the front direction is attenuated, so that a representing the orientation state can be easily obtained. A difference between the structure and the fabrication method of Light-emitting Element 7 and those of Light-emitting Element 7-1 lies only in the layer for adjusting the thickness; thus, the orientation states of light-emitting substances in the light-emitting layers are assumed to be the same.

The orientation state of a light-emitting material in the light-emitting layer was examined with the use of Light-emitting Element 7-1. First, the angle dependence of the shape of the EL emission spectrum was measured by measuring the EL spectrum in steps of 1° in such a manner that, as shown in FIG. 20, the substrate provided with Light-emitting Element 7-1 was inclined to a detector (a photonic multichannel analyzer PMA-12, produced by Hamamatsu

TABLE 13

| | hole-injection layer | hole-transport layer | light-emitting layer | electron-transport layer | electron-injection layer | layer for adjusting the thickness | |
|---|---|---|---|---|---|---|---|
| | 10 nm | 80 nm | 30 nm | 30 nm | 20 nm | 0.1 nm | 2 nm | 85 nm |
| Element 7 | HAT-CN | NPB | Rubrene: α,β-ADN:DBP (0.8:0.2:0.005) | α,β-ADN | BPhen | $Li_2O$ | — | — |
| Element 7-1 | | | | | | | CuPc | DBT3P-II:MoOx (4:2) |

Photonics K.K.) from θ=0° to 80°. In this measurement, a linear polarizer (Glan-Taylor prism) was disposed between Light-emitting Element 7-1 and the detector to be perpendicular to the substrate surface in order to remove an S polarization from light emitted from Light-emitting Element 7-1, so that the spectrum of only a P polarization was measured.

Figure 43:
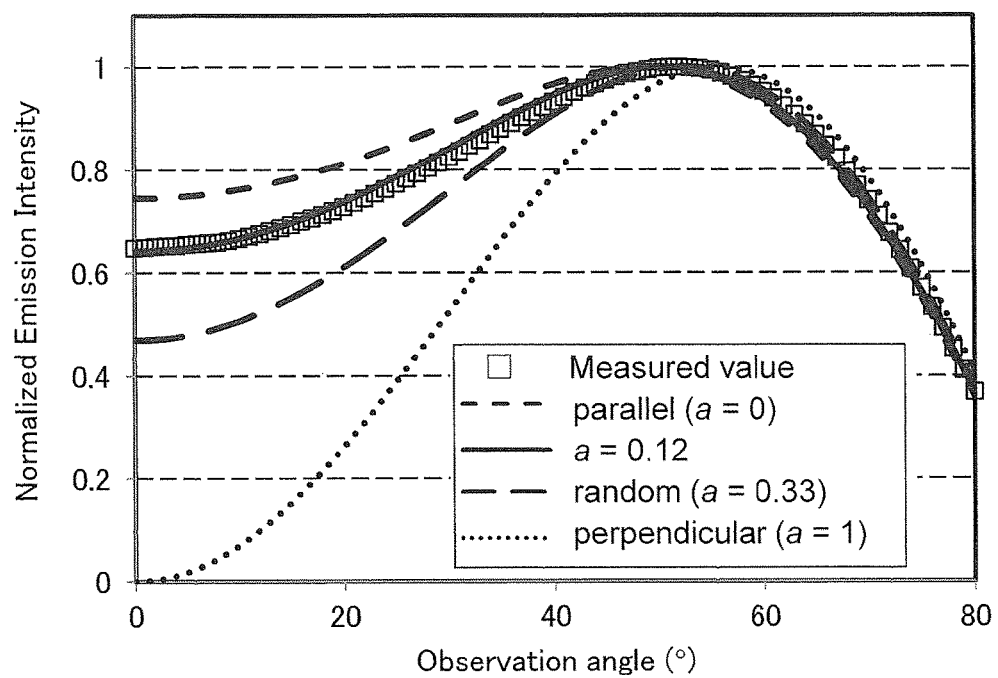
FIG. 43 is a graph showing the measured and calculated integrated intensity of the EL emission spectrum depending on the angle (θ) of the detector of Light-emitting Element 7-1.

FIG. 43 is a graph in which the vertical axis represents the integrated intensity of the EL emission spectrum from 570 nm to 900 nm depending on the angle (θ) and the horizontal axis represents the angle (θ) of the detector. In FIG. 43, a curve plotted by open squares represents the measured values, and a solid curve and a dashed curve represent the calculation results obtained by setfos which is an organic device simulator. The calculation was performed by inputting the thickness of each layer in the element, the measured values of the refractive index and the extinction efficiency, the measured value of the emission spectrum of a dopant, the position and the width of a light-emitting region, and the orientation parameter a. Among them, the thickness of each layer, the refractive index, and the extinction efficiency were measured with the use of a spectroscopic ellipsometer (M-2000U, produced by J.A. Woollam Japan Corp.). For the measurement, a film was used which was formed of the light-emitting material over a quartz substrate by a vacuum evaporation method to a thickness of 150 nm. The emission spectrum of the dopant was measured using a fluorescence spectrophotometer (FS920, produced by Hamamatsu Photonics K.K.). For the measurement, a film was used which was formed by co-evaporation of rubrene, α,β-ADN, and DBP using a vacuum evaporation method at a weight ratio of 0.8:0.2:0.005 (=rubrene: α,β-ADN: DBP) over a quartz substrate to a thickness of 50 nm. In the calculation by setfos, further, the light-emitting region was set. The light-emitting region was assumed to spread such that the recombination probability was attenuated in accordance with the Gaussian distribution with a point which is approximately 6 nm from the interface between the hole-transport layer and the light-emitting layer as a top, specifically, the distance between inflection points of an assumed Gaussian function was 25 nm. Thus, the angle dependence of the integrated intensity of the emission spectrum corresponding to each parameter a can be calculated. In Light-emitting Element 7-1, the measured value well fitted a curve of a=0.12.

Figure 44:
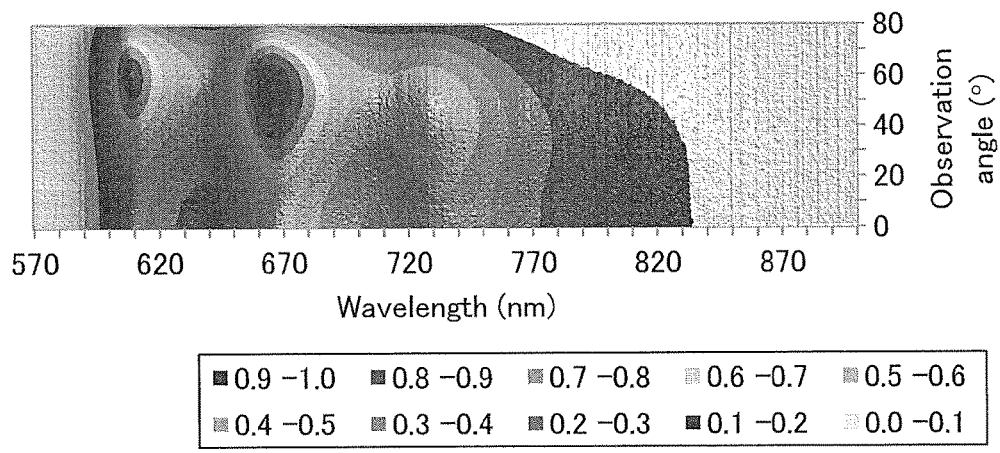
FIG. 44 is a 2D contour map showing the measured angle dependence of the EL emission spectrum of Light-emitting Element 7-1.
Figure 45:
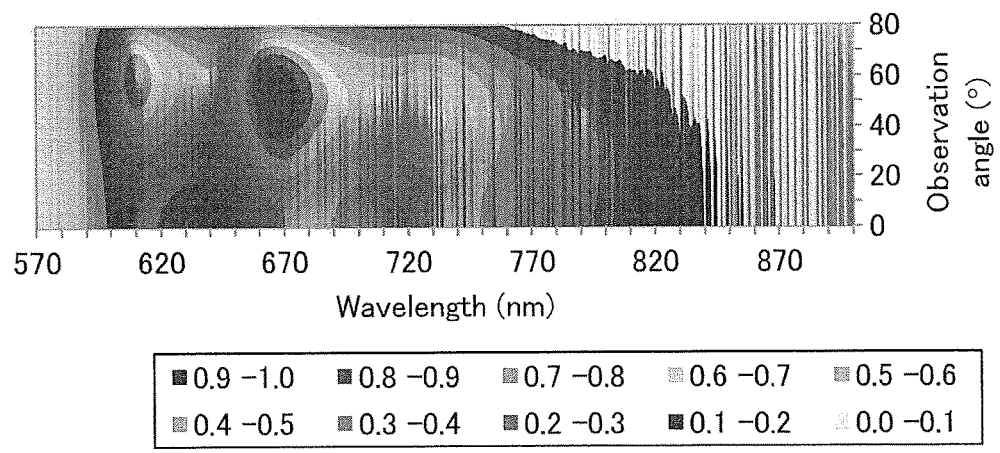
FIG. 45 is a 2D contour map obtained by calculation of Light-emitting Element 7-1.

FIG. 44 is a 2D contour map obtained by measuring the angle dependence of the EL emission spectrum of Light-emitting Element 7-1. FIG. 45 is a 2D contour map obtained by calculation. FIG. 44 and FIG. 45 show that these 2D contour maps match well. This indicates that the orientation of the light-emitting materials in Light-emitting Elements 7 and 7-1 was accurately obtained in both the experiment and the calculation.

The parameter a is ⅓≈0.33 in the case where the transition dipole is oriented in a random direction, and the parameter a is 0 in the case where the transition dipole is completely parallel to the substrate. The light extraction efficiency in the case of a=0 is 1.5 times the light extraction efficiency in the case of a=⅓≈0.33. In view of this, the light-emitting element of this example in which a=0.12 has light extraction efficiency that is 1.32 times the light extraction efficiency of the light-emitting element with a random orientation. That is, the light-emitting element of one embodiment of the present invention has an emission efficiency that is 1.32 times the emission efficiency of the light-emitting element with a random orientation.

Light-emitting Elements 7 and 7-1 are formed using the same material for their light-emitting layers by the same method; thus, it can be said that Light-emitting Element 7 has, like Light-emitting Element 7-1, an orientation of a=0.12. Light-emitting Element 7 has a very high external quantum efficiency of 11%. It is found that a light-emitting element with high emission efficiency can be obtained by setting a to less or equal to 0.2. Measurement results of transient EL emission indicate that TTA also occurred in this element.

Example 8

In this example, results of calculating the parameter a of a light-emitting element (Light-emitting Element 8) of one embodiment of the present invention with high efficiency are described in detail. For the above purpose, a light-emitting element (Light-emitting Element 8-1) for measurement which includes a light-emitting layer having the same structure as that of Light-emitting Element 8 and in which the luminance in the front direction is reduced as much as possible was also fabricated.

First, a fabrication method and the structure of the light-emitting element of one embodiment of the present invention are described. Organic compounds used in the light-emitting element of one embodiment of the present invention are given below.

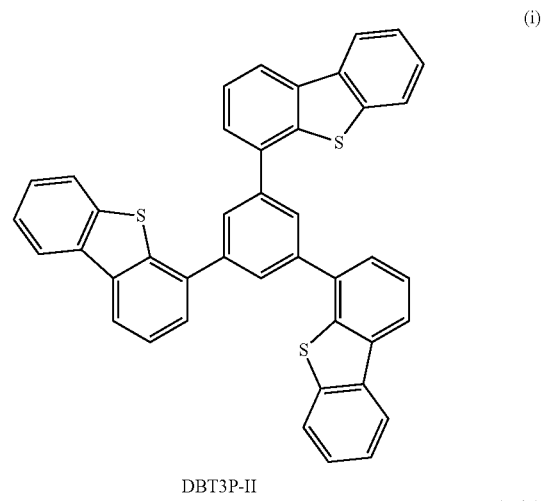

DBT3P-II

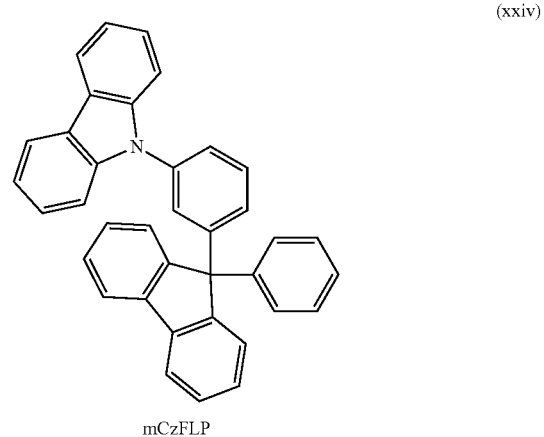

mCzFLP

-continued

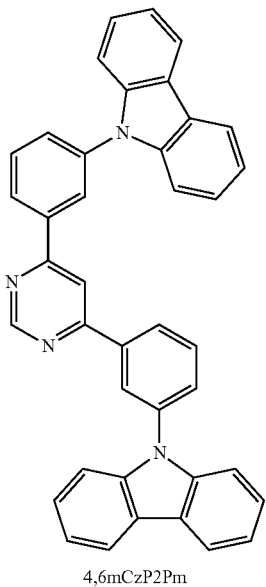

4,6mCzP2Pm (xii)

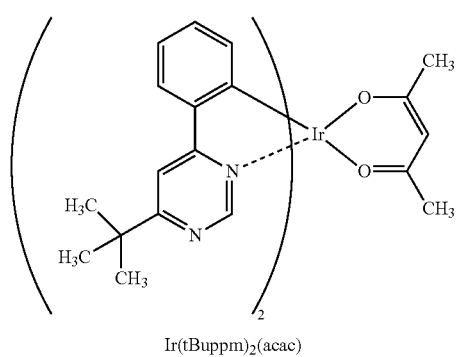

Ir(tBuppm)₂(acac) (xxv)

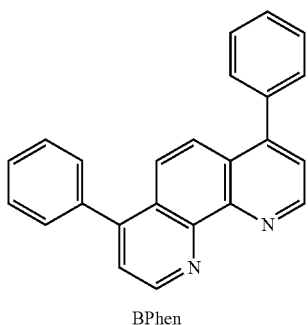

BPhen (v)

-continued

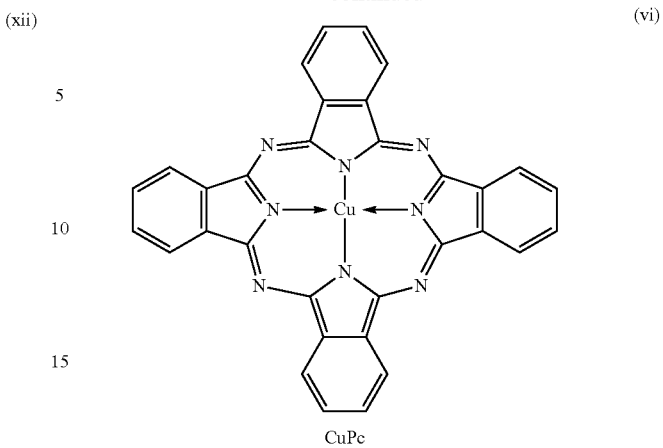

CuPc (vi)

(Fabrication Method of Light-Emitting Element 8)

First, a film of indium tin oxide containing silicon oxide (ITSO) was formed over a glass substrate by a sputtering method, so that the first electrode 101 was formed. The thickness of the first electrode 101 was 70 nm and the electrode area was 2 mm×2 mm.

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 4,4',4''-(benzene-1,3,5-triyl) tri(dibenzothiophene) (abbreviation: DBT3P-II) represented by Structural Formula (i) and molybdenum(VI) oxide were deposited by co-evaporation to a thickness of 50 nm at a weight ratio of 4:2 (=DBT3P-II: molybdenum oxide) by an evaporation method using resistance heating, so that the hole-injection layer 111 was formed.

Then, 9-[3-(9-phenyl-9H-fluoren-9-yl)phenyl]-9H-carbazole (abbreviation: mCzFLP) represented by Structural Formula (xxiv) was deposited by evaporation to a thickness of 20 nm on the hole-injection layer 111 to form the hole-transport layer 112.

Then, the light-emitting layer 113 was formed in the following manner: 4,6-bis[3-(9H-carbazol-9-yl)phenyl]pyrimidine (abbreviation: 4,6mCzP2Pm) represented by Structural Formula (xii) and bis[2-(6-tert-butyl-4-pyrimidinyl-κN³)phenyl-κC](2,4-pentanedionato-κ²O,O')iridium(III) (abbreviation: [Ir(tBuppm)₂(acac)]) represented by Structural Formula (xxv) were deposited by co-evaporation at a weight ratio of 1:0.05 (=4,6mCzP2Pm: [Ir(tBuppm)₂(acac)]) to a thickness of 40 nm.

Then, on the light-emitting layer 113, 4,6mCzP2Pm was deposited by evaporation to a thickness of 15 nm, and bathophenanthroline (abbreviation: BPhen) represented by Structural Formula (v) was deposited by evaporation to a thickness of 10 nm to form the electron-transport layer 114.

After the formation of the electron-transport layer 114, lithium oxide (Li$_2$O) was deposited by evaporation to a thickness of 0.1 nm to form the electron-injection layer 115. Then, aluminum was deposited by evaporation to a thickness of 200 nm to form the second electrode 102. Through the above-described steps, Light-emitting Element 8 of this example was fabricated.

(Fabrication Method of Light-Emitting Element 8-1)

Light-emitting element 8-1 was fabricated in the following manner. After the electron-injection layer 115 of Light-emitting Element 8 was formed, copper phthalocyanine (abbreviation: CuPc) represented by Structural Formula (vi) was deposited by evaporation to a thickness of 2 nm, and then, DBT3P-II and molybdenum(VI) oxide were deposited by co-evaporation at a weight ratio of 2:1 (=DBT3P-II: molybdenum oxide) to a thickness of 80 nm. In such a manner, a layer for adjusting the thickness was formed.

The element structures of Light-emitting Elements 8 and 8-1 are shown in the following table.

TABLE 15

|  | hole-injection layer | hole-transport layer | light-emitting layer | electron-transport layer | electron-injection layer | layer for adjusting the thickness | |
| --- | --- | --- | --- | --- | --- | --- | --- |
|  | 50 nm | 20 nm | 40 nm | 15 nm | 10 nm | 0.1 nm | 2 nm | 80 nm |
| Element 8 | DBT3P-II:MoOx (4:2) | mCzFLP | 4,6mCzP2Pm: [Ir(tBuppm)$_2$(acac)] (1:0.05) | 4,6CzP2Pm | BPhen | Li$_2$O | — | — |
| Element 8-1 |  |  |  |  |  |  | CuPc | DBT3P-II:MoOx (4:2) |

Light-emitting Elements 8 and 8-1 were each sealed using a glass substrate in a glove box containing a nitrogen atmosphere so as not to be exposed to the air (specifically, a sealant was applied to surround the element and UV treatment and heat treatment at 80° C. for 1 hour were performed at the time of sealing). Then, the initial characteristics of Light-emitting Elements 8 and 8-1 were measured. Note that the measurement was carried out in an atmosphere kept at 25° C.

Figure 46:
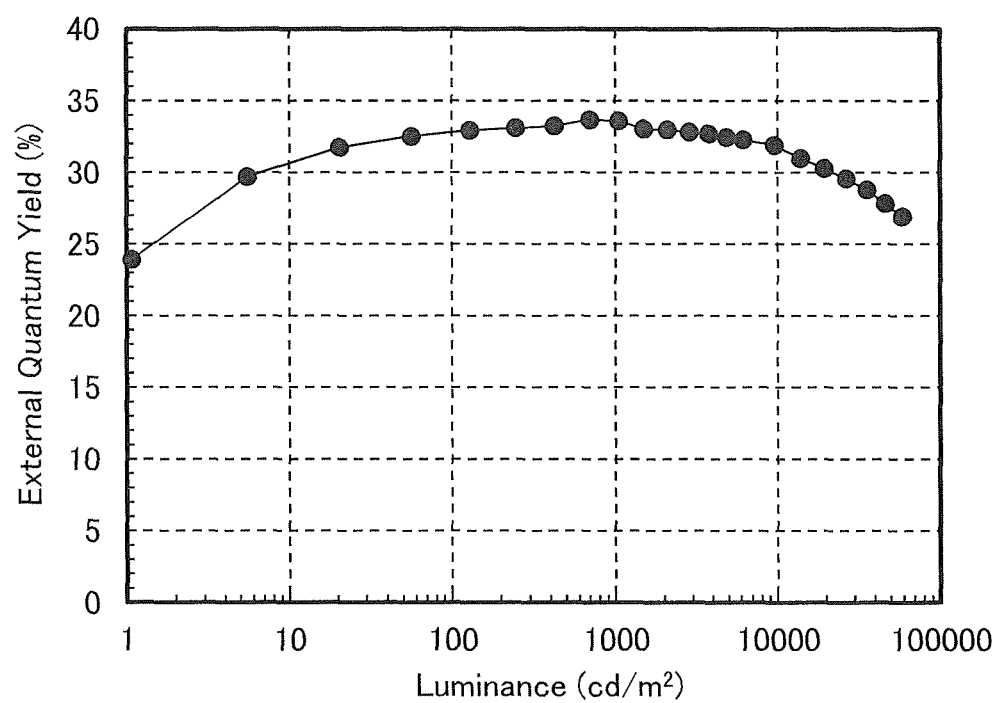
FIG. 46 shows the external quantum efficiency-luminance characteristics of Light-emitting Element 8.

FIG. 46 shows the external quantum efficiency-luminance characteristics of Light-emitting Element 8. Table 16 shows the main characteristics of Light-emitting Elements 8 and 8-1 at a luminance of about 1000 cd/m$^2$.

TABLE 16

|  | Voltage (V) | Current (mA) | Current density (mA/cm$^2$) | chromaticity x | chromaticity y | Current Efficiency (cd/A) | External Quantum Efficiency (%) |
| --- | --- | --- | --- | --- | --- | --- | --- |
| Element 8 | 3.4 | 0.03 | 0.8 | 0.40 | 0.59 | 128 | 31 |
| Element 8-1 | 5.6 | 1.06 | 27 | 0.43 | 0.53 | 3.7 | 1.7 |

As shown in Table 16, Light-emitting Element 8 has a very high efficiency, e.g., an external quantum efficiency of 31%. The light-emitting material used in Light-emitting Element 8, [Ir(tBuppm)$_2$(acac)], has an emission quantum yield (φ) of 0.91. Assuming that the carrier balance (γ) is 1 and the proportion of generated excitons (α) is 1, the light extraction efficiency (χ) is calculated to 34.1%, which is much higher than a general theoretical light extraction efficiency of 20% to 30%.

Light-emitting Element 8-1 includes the layer for adjusting the thickness in addition to the components of Light-emitting Element 8. By adjusting the optical path length, light that travels in the front direction is attenuated, so that a representing the orientation state can be easily obtained. A difference between the structure and the fabrication method of Light-emitting Element 8 and those of Light-emitting Element 8-1 lies only in the layer for adjusting the thickness; thus, the orientation states of light-emitting substances in the light-emitting layers are assumed to be the same.

The orientation state of a light-emitting material in the light-emitting layer was examined with the use of Light-emitting Element 8-1. First, the angle dependence of the shape of the EL emission spectrum was measured by measuring the EL spectrum in steps of 1° in such a manner that, as shown in FIG. 20, the substrate provided with Light-emitting Element 8-1 was inclined to a detector (a photonic multichannel analyzer PMA-12, produced by Hamamatsu Photonics K.K.) from θ=0° to 80°. In this measurement, a linear polarizer (Glan-Taylor prism) was disposed between Light-emitting Element 8-1 and the detector to be perpendicular to the substrate surface in order to remove an S polarization from light emitted from Light-emitting Element 8-1, so that the spectrum of only a P polarization was measured.

Figure 47:
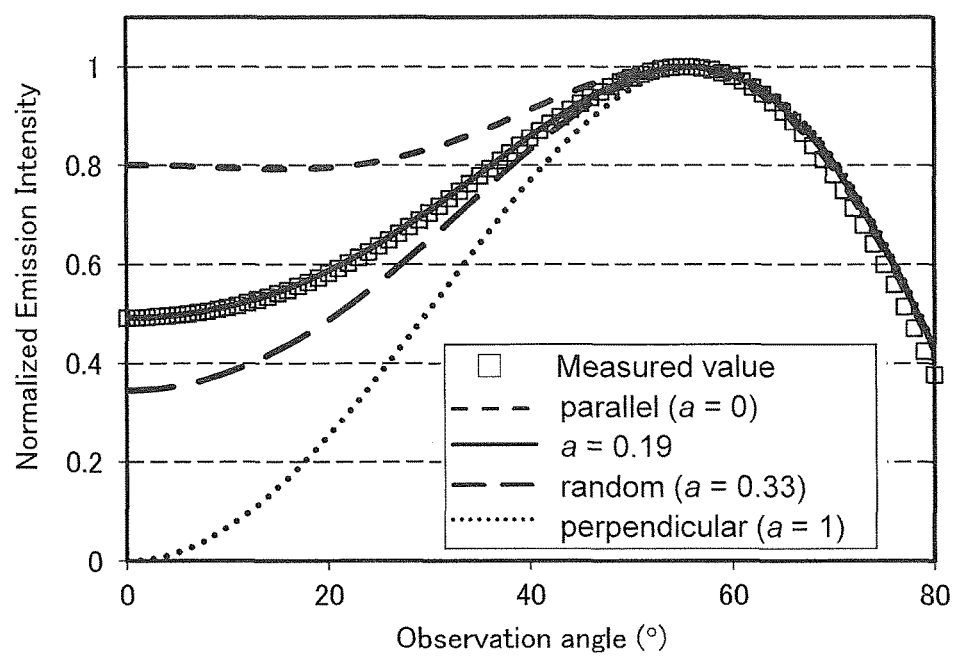
FIG. 47 is a graph showing the measured and calculated integrated intensity of the EL emission spectrum depending on the angle (θ) of the detector of Light-emitting Element 8-1.

FIG. 47 is a graph in which the vertical axis represents the integrated intensity of the EL emission spectrum from 480 nm to 800 nm depending on the angle (θ) and the horizontal axis represents the angle (θ) of the detector. In FIG. 47, a curve plotted by open squares represents the measured values, and a solid curve and a dashed curve represent the calculation results obtained by setfos which is an organic device simulator. The calculation was performed by inputting the thickness of each layer in the element, the measured values of the refractive index and the extinction efficiency, the measured value of the emission spectrum of a dopant, the position and the width of a light-emitting region, and the orientation parameter a. Among them, the thickness of each layer, the refractive index, and the extinction efficiency were measured with the use of a spectroscopic ellipsometer (M-2000U, produced by J.A. Woollam Japan Corp.). For the measurement, a film was used which was formed of the light-emitting material over a quartz substrate by a vacuum evaporation method to a thickness of 150 nm. The emission spectrum of the dopant was measured using a fluorescence spectrophotometer (FS920, produced by Hamamatsu Photonics K.K.). For the measurement, a film was used which was formed by co-evaporation of 4,6mCzP2Pm and [Ir(tBuppm)$_2$(acac)] using a vacuum evaporation method at a weight ratio of 1:0.05 (=4,6mCzP2Pm: [Ir(tBuppm)$_2$(acac)]) over a quartz substrate to a thickness of 40 nm. In the calculation by setfos, further, the light-emitting region was set. The light-emitting region was assumed to spread such that the recombination probability was attenuated in accordance with the Gaussian distribution with the interface between the hole-transport layer and the light-emitting layer as a top, specifically, the distance between inflection points of an assumed Gaussian function was 11.5 nm. Thus, the angle dependence of the integrated intensity of the emission spectrum corresponding to each parameter a can be calculated. In Light-emitting Element 8-1, the measured value well fitted a curve of a=0.19.

Figure 48:
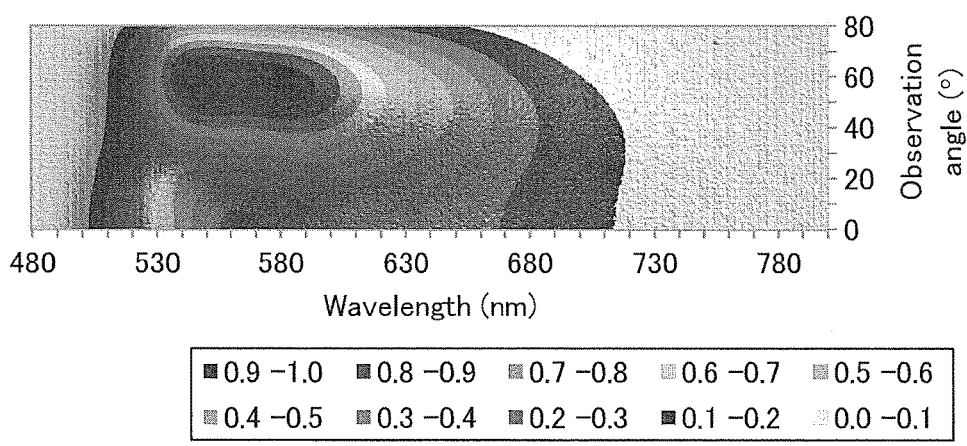
FIG. 48 is a 2D contour map showing the measured angle dependence of the EL emission spectrum of Light-emitting Element 8-1.
Figure 49:
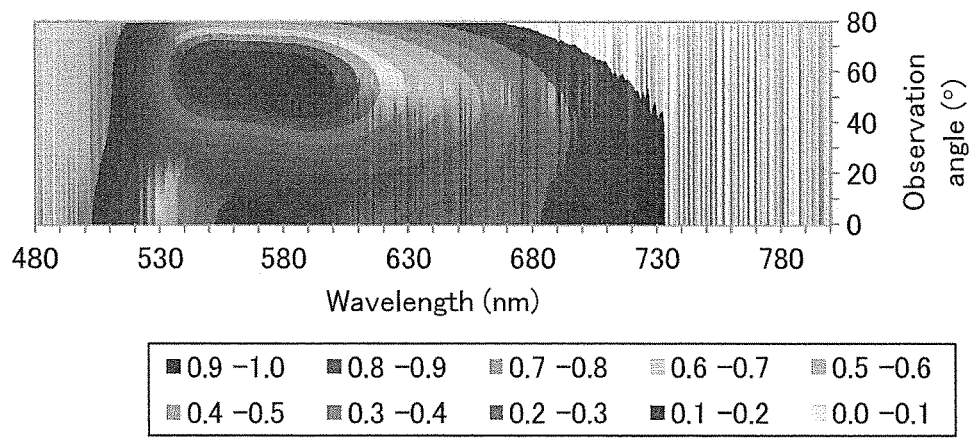
FIG. 49 is a 2D contour map obtained by calculation of Light-emitting Element 8-1.

FIG. 48 is a 2D contour map obtained by measuring the angle dependence of the EL emission spectrum of Light-emitting Element 8-1. FIG. 49 is a 2D contour map obtained by calculation. FIG. 48 and FIG. 49 show that these 2D contour maps match well. This indicates that the orientation of the light-emitting materials in Light-emitting Elements 8 and 8-1 was accurately obtained in both the experiment and the calculation.

The parameter a is ⅓≈0.33 in the case where the transition dipole is oriented in a random direction, and the parameter a is 0 in the case where the transition dipole is completely parallel to the substrate. The light extraction efficiency in the case of a=0 is 1.5 times the light extraction efficiency in the case of a=⅓≈0.33. In view of this, the light-emitting element of this example in which a=0.19 has light extraction efficiency that is 1.22 times the light extraction efficiency of the light-emitting element with a random orientation.

Light-emitting Elements 8 and 8-1 are formed using the same material for their light-emitting layers by the same method; thus, it can be said that Light-emitting Element 8 has, like Light-emitting Element 8-1, an orientation of a=0.19. Light-emitting Element 8 has a very high external quantum efficiency of 31%. It is found that a light-emitting element with high emission efficiency can be obtained by setting a to less than or equal to 0.2.

This application is based on Japanese Patent Application Serial No. 2016-101789 filed with Japan Patent Office on May 20, 2016, and Japanese Patent Application Serial No. 2016-122964 filed with Japan Patent Office on Jun. 21, 2016, the entire contents of which are hereby incorporated by reference.

What is claimed is:

1. A light-emitting element comprising:
a first electrode;
an EL layer over the first electrode, the EL layer comprising:
a light-emitting layer comprising a first substance and a second substance; and
a second electrode over the EL layer,
wherein an amount of the first substance is larger than an amount of the second substance in the light-emitting layer,
wherein each molecule of the second substance in the light-emitting layer has an average transition dipole moment,
wherein the second substance in the light-emitting layer has molecular orientation parameter a,
wherein the molecular orientation parameter a is a proportion of TMv component in the whole average transition dipole moments,
wherein the TMv component is a vector component in a direction perpendicular to the first electrode among the whole average transition dipole moments, and
wherein the molecular orientation parameter a is greater than 0 and less than or equal to 0.2.

2. The light-emitting element according to claim 1, wherein molecules of the second substance in the light-emitting layer are oriented.

3. The light-emitting element according to claim 1, wherein the light-emitting layer is deposited by a vacuum evaporation method under an atmosphere which has a higher volume ratio of a partial pressure of carbon dioxide to the total pressure than the air.

4. The light-emitting element according to claim 1,
wherein the light-emitting layer is deposited by a vacuum evaporation method under an atmosphere which has a first percentage of a partial pressure of carbon dioxide with respect to the total pressure, and
wherein the first percentage is 0.1% or higher and 10% or less.

5. The light-emitting element according to claim 1,
wherein the light-emitting layer further comprises a third substance, and
wherein the first substance and the third substance is configured to form an exciplex.

6. The light-emitting element according to claim 1, wherein the second substance is a fluorescent substance.

7. The light-emitting element according to claim 1, wherein the second substance has a condensed aromatic hydrocarbon skeleton.

8. The light-emitting element according to claim 6, wherein an external quantum efficiency of the light-emitting element is higher than or equal to 10%.

9. The light-emitting element according to claim 1, wherein light emission from the light-emitting element comprises a delayed fluorescent component.

10. The light-emitting element according to claim 1, wherein the molecular orientation parameter a is greater than 0 and less than or equal to 0.15.

11. A light-emitting device comprising:
the light-emitting element according to claim 1; and
at least one of a transistor and a substrate.

12. An electronic device comprising:
the light-emitting device according to claim 11; and
at least one of a sensor, an operation button, a speaker and a microphone.

13. A lighting device comprising:
the light-emitting device according to claim 11; and
a housing.

14. A light-emitting element comprising:
a first electrode;
an EL layer over the first electrode, the EL layer comprising:
a light-emitting layer comprising a first substance and a second substance; and
a second electrode over the EL layer,
wherein an amount of the first substance is larger than an amount of the second substance in the light-emitting layer,
wherein the second substance is an iridium complex,
wherein each molecule of the second substance in the light-emitting layer has an average transition dipole moment,
wherein the second substance in the light-emitting layer has molecular orientation parameter a, wherein the molecular orientation parameter a is a proportion of TMv component in the whole average transition dipole moments, wherein the TMv component is a vector component in a direction perpendicular to the first electrode among the whole average transition dipole moments, and wherein the molecular orientation parameter a is greater than 0 and less than or equal to 0.2.

15. The light-emitting element according to claim 14, wherein the iridium complex comprises an azole skeleton.

16. The light-emitting element according to claim 15, wherein the azole skeleton is a triazole skeleton.

17. The light-emitting element according to claim 14,
wherein the light-emitting layer further comprises a third substance, and
wherein the first substance and the third substance is configured to form an exciplex.

18. The light-emitting element according to claim 14, wherein the light-emitting layer is deposited by a vacuum evaporation method under an atmosphere which has a higher volume ratio of a partial pressure of carbon dioxide to the total pressure than the air.

19. The light-emitting element according to claim 14,
wherein the light-emitting layer is deposited by a vacuum evaporation method under an atmosphere which has a first percentage of a partial pressure of carbon dioxide with respect to the total pressure, and
wherein the first percentage is 0.1% or higher and 10% or less.

20. The light-emitting element according to claim 14, wherein the molecular orientation parameter a is greater than 0 and less than or equal to 0.15.

* * * * *